(12) United States Patent
Kubo et al.

(10) Patent No.: US 8,039,687 B2
(45) Date of Patent: Oct. 18, 2011

(54) METHOD FOR SCREENING GENOMIC DNA FRAGMENTS

(75) Inventors: Tomoaki Kubo, Iwata (JP); Toshihiko Komari, Iwata (JP); Satoru Usami, Iwata (JP); Yoshimitsu Takakura, Iwata (JP); Yukoh Hiei, Iwata (JP); Yuji Ishida, Iwata (JP)

(73) Assignee: Japan Tobacco Inc., Tokyo (JP)

( * ) Notice: Subject to any disclaimer, the term of this patent is extended or adjusted under 35 U.S.C. 154(b) by 721 days.

(21) Appl. No.: 10/576,693

(22) PCT Filed: Oct. 22, 2004

(86) PCT No.: PCT/JP2004/015743
§ 371 (c)(1),
(2), (4) Date: Jan. 26, 2007

(87) PCT Pub. No.: WO2005/040374
PCT Pub. Date: May 6, 2005

(65) Prior Publication Data
US 2008/0301832 A1  Dec. 4, 2008

(30) Foreign Application Priority Data
Oct. 24, 2003  (JP) .................................. 2003-364682

(51) Int. Cl.
| C12N 15/82 | (2006.01) |
| C12N 15/10 | (2006.01) |
| C12N 15/29 | (2006.01) |
| C12N 15/55 | (2006.01) |
| C12N 15/70 | (2006.01) |
| C12N 15/84 | (2006.01) |

(52) U.S. Cl. ....... 800/278; 800/279; 800/290; 435/91.1; 435/91.2; 435/91.32; 435/199; 435/252.33; 435/468; 435/469; 435/470

(58) Field of Classification Search ........................ None
See application file for complete search history.

(56) References Cited

U.S. PATENT DOCUMENTS

| 5,977,439 A * | 11/1999 | Hamilton ...................... 800/294 |
| 6,165,780 A | 12/2000 | Kawasaki |
| 6,521,408 B1 | 2/2003 | Kawasaki |
| 6,794,190 B2 | 9/2004 | Kawasaki |
| 7,045,679 B1 | 5/2006 | Wilson |
| 2003/0003585 A1 | 1/2003 | Kawasaki |

FOREIGN PATENT DOCUMENTS

| JP | 10-155485 A | 6/1998 |
| WO | WO 03/018808 A | 3/2001 |
| WO | WO-01/85909 A2 | 11/2001 |

OTHER PUBLICATIONS

Lazo et al. A DNA transformation-competant arabidopsis genomic library in Agrobacterium. (1991) Bio/Technology; vol. 9; pp. 963-967.*
Hamilton et al. The Plant Journal 18(2): 223-229 (Apr. 1999).*
Tigchelaar et al. HortScience 13(5): 508-513 (Oct. 1978).*
Valveekens et al. Proc. Natl. Acad. Sci. USA 85(15): 5536-5540 (Aug. 1998).*
Haugn et al. Molecular and General Genetics 204(3): 430-434 (Sep. 1986).*
Olszewski et al. Nucleic Acids Research 16(22): 10765-10782 (1988).*
Frary et al. Plant Cell Reports 16(3-4): 235-240 (Dec. 1996).*
Maram Girgi et al., Molecular Breeding, 10(4): 243-252, 2002.
T.A. Campbell, "Investigation of variations in NBS motifs in alfalfa (*Medicago sativa*), *M. edgeworthii*, and *M. ruthenica*," Canadian Journal of Plant Science, 83(2):371-375, 2003.
Meenu Kesarwani et al., The Journal of Biological Chemistry, 275(10):7230-7238, 2000.
Regina Preisig-Muller et al., Plant Molecular Biology, 29(2):221-229, 1999.
Ott, et al., Mol Gen Genet, (1990), vol. 223, pp. 169-179.
Shi, et al., Plant Science, (2003), vol. 165, pp. 879-885.
He, et al., Gene, (2003), vol. 321, pp. 113-121.
Jordan, et al., Trends in Plant Science, (2002), vol. 7(9), pp. 392-398.
Dairi, et al., Mol Gen Genet, (2000), vol. 262, pp. 957-964.
Klee, et al., Mol Gen Genet, (1987), vol. 210, pp. 282-287.
Genetics and Exploitation of Heterosis in Crops, (1999), p. 173, Coors and Pandey, Madison, WI, USA.
Fu, et al., PNAS, (2002), vol. 99, pp. 9573-9578.
Song, et al., PNAS, (2003), vol. 100(15), pp. 9055-9060.
Schwartz, D., Theor Appl Genet, (1973), vol. 43, pp. 117-120.
Hollick, et al., Genetics, (1998), vol. 150, pp. 891-897.
Stuber, C., Plant Breeding Reviews, (1994), vol. 12, pp. 227-251.
Li, et al., Plant Breeding Reviews, (2000), vol. 17, pp. 15-47,112-115, & 120-123.
Liu, et al., PNAS, (1999), vol. 96, pp. 6535-6540.
Ku, et al., Nature Biotechnol, (1999), vol. 17, pp. 76-80.
Shibata, et al., Trends Plant Science, (2000), vol. 5, pp. 354-357.
Plant Gene Engineering, 2nd Edition, Science Press, Aug. 30, 2002, p. 147.
Kawasaki et al., Bio Science Industry, vol. 55, No. 7, 1997, pp. 487-489, 1997.

* cited by examiner

*Primary Examiner* — David T Fox
(74) *Attorney, Agent, or Firm* — Birch, Stewart, Kolasch, and Birch, LLP

(57) ABSTRACT

The present invention provides a method for selecting genomic DNA fragments which are useful for providing a plant with an agriculturally advantageous improvement. The method of the present invention comprises the steps of: 1) preparing genomic DNA from a plant, which is then cloned into a cloning vector to form a genomic DNA library; 2) introducing a genomic fragment from each of the genomic clones constituting the genomic DNA library separately into a plant to produce transgenic plants; 3) cultivating the transgenic plants or progeny thereof to select a plant exhibiting an agriculturally advantageous phenotypic variation; and 4) selecting the genomic DNA fragment, which was introduced in step (2) into the plant selected in step (3), as a purposed genomic DNA fragment.

31 Claims, 10 Drawing Sheets
(5 of 10 Drawing Sheet(s) Filed in Color)

Fig. 4: Results of testing of blast resistance

Fig. 5    Extension of leaves of various varieties and lines under stress

Fig. 6 : Effect of introducing genomic DNA fragments on the growth of tobacco cullus Growth of rice cultivated after treatment with teosinte genomic DNA fragments; plant bodies at day 45 after transplantation; the arrow indicates the control individual; the introduced genomic fragments are, from left to right:

M044G07, M043C09, M042F06, M043A11, M042H08, M043B10, M044E12, Control, M042E11, M043A08

Fig. 8: Sites of PCR amplification on a genomic DNA fragment of *Oryza rufipogon*
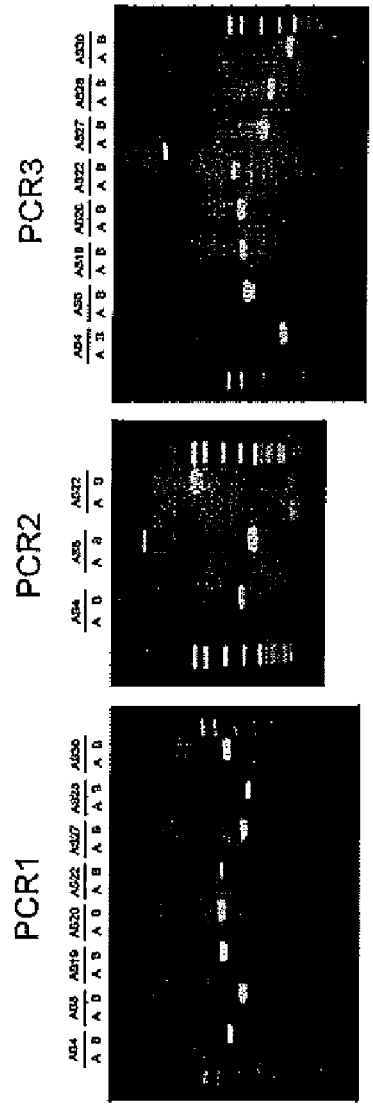
A: pSB200
B: plasmid having the indicated fragment inserted into pSB200
Fig. 9 : Results of PCR analysis

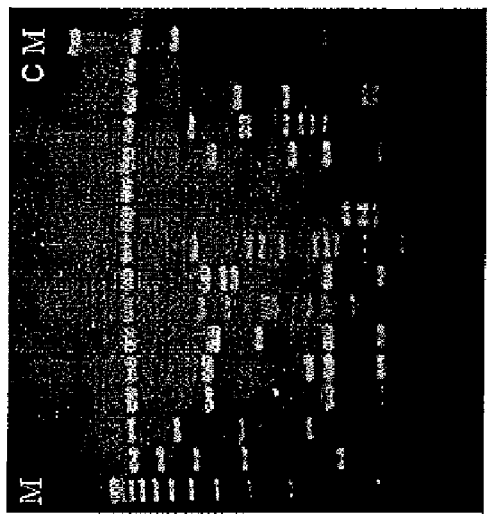
Fig. 10  From left to right:
lane 1 (M): 1 kb ladder
lanes 2-14: AS88, 90, 95-102, 104-106
C: vector control
M2: λ/HindIII size marker

Fig. 11: Vector size determination by electrophoresis
1 : G001A03 (original)
2 : G001A03DEST
3 : G001A03bar
M : 1kb ladder

METHOD FOR SCREENING GENOMIC DNA FRAGMENTS

This application is a 371 of PCT/JP04/15743 filed 22 Oct. 2004.

TECHNICAL FIELD

This invention relates to a method for efficient screening of genomic DNA fragments capable of providing plants with an agriculturally advantageous phenotypic variation.

BACKGROUND ART

With a view to breeding agriculturally advantageous new plant varieties, cross breeding in which two plants are crossed and progeny is selected, mutation breeding in which mutation is induced in a plant, and other methods have conventionally been practiced. Recently, with the progress of biotechnology, genetically modified plants have been bred by introducing a useful gene and causing its function to be expressed.

Breeding a New Variety by Introducing an Individual Gene

In order to breed a new variety by genetic engineering, it is usually required at a first step to isolate a gene and analyze its function. Recent years have seen a dramatic increase in molecular biological findings about plant genes and the genomic DNA sequences of many species have been determined with many partial—as well as full-length cDNA clones being isolated and determined for their sequences. However, many of the heretofore cloned putative gene functions are simply based on the information that the nucleotide sequences of genetic coding regions or the amino acid sequences deduced therefrom of the proteins are similar to the sequences of already discovered enzyme genes and the like and in order to verify the function of a particular gene, one must make sure that the expression of the gene and its phenotype agree in a transformant. As a result, considerable time and labor is required to unravel the functions of individual genes and little progress has been made in this aspect. An attempt is being made to verify the functions of a gene by isolating a full-length cDNA clone, linking it to a suitable promoter and terminator and transforming it. As an improved version of this attempt, a technique has been developed that comprises introducing a library of full-length cDNAs into a plant and making an exhaustive analysis of functions of the genes (WO 03/018808A). However, in those approaches, the promoter is not what is inherently associated with the gene and introns as well as other gene expression regulating functions have been removed, so it is not expected for the genes to be expressed to exhibit the inherent functions. As a further problem, splicing of some genes is shown to be alternative (Jordan et al. Trends in Plant Sciences 7:392-398, 2002), so the cDNA clones obtained may have lost their inherent functions. As a matter of fact, the phenotypic variations observed in such transgenic plants do not have much utility for the purpose of breeding a new variety.

In recent years, techniques in bioinformatics are employed to deduce coding region that is translated into the protein, and promoter, intron and other regions of a gene. Modes of gene expression are investigated by the microarray technology using DNA fragments. A number of function-deficient variants have been prepared by the gene knockout technique and are used in function analysis of genes. In addition, transformants having enhanced gene expression are prepared by activation tagging and used in function analysis of genes. To unravel the interrelationship between proteins encoded by genes, two-hybrid system is employed.

In the deduction of gene function by bioinformatics, the finding obtained from the relation between the function and structure of a known protein and the sequence of the gene encoding it are often employed to search for the yet to be known function of a gene. However, recent studies have shown that there are many cDNAs that are not translated into proteins, or which permit transcription of a mRNA-like RNA but not produce a protein. There are also many genes that function as low-molecular weight RNAs after transcription. Therefore, in the bioinformatics techniques proposed to date, there are many genes on genomic DNA that present difficulty in unraveling their functions. Therefore, deducing gene functions is not easy even if such latest techniques are fully exploited.

As noted above, analysis of gene functions is not easy even today. And even if a gene function is specified, it is difficult for the above-mentioned methods involving the transformation of individual genes to breed a new variety that is improved in traits whose expression will be improved in so-called heterosis or in quantitative traits.

In order to capture a gene in a certain organism that brings about a known phenotype possessed by said organism, an attempt is being widely made that comprises constructing genomic libraries from said organism, introducing the libraries with a plasmid into a microorganism such as yeast or bacterium to prepare transformed cells, selecting a particular transformed cell on the basis of the information known for said known phenotype, for example, information such as the transcript of said gene, and employing the selected transformant to clone the desired-gene (shotgun cloning) (Dairi et al. Mol Gen Genet 262:957-964, 2000).

In one application of shotgun cloning, a plant genomic library was transformed by introducing it into a plant, rather than a microorganism (Klee et al. Mol Gen Genet 210:282-287, 1987). In this experiment, a genomic library was constructed from an *Arabidopsis* transformant prepared by introducing a kanamycin resistance gene from a microorganism. Petunia leaf discs were infected with mixed strains of *Agrobacterium* containing the genomic clones in order to select kanamycin resistant petunia cells, namely, petunia cells harboring the kanamycin resistance gene derived from the *Arabidopsis* transformant. As a result, it was shown that the microorganism derived kanamycin resistance gene in the *Arabidopsis* genome could be captured after introduction into petunia by transformation.

Further disclosed in connection with *Arabidopsis* was a case in which a genomic library was constructed from a mutant showing chlorosulfuron resistance due to mutation in the acetohydroxy acid synthase (AHAS) gene and three genomic clones harboring the mutant AHAS gene were isolated and introduced into tobacco, producing chlorosulfuron resistant transformants (Olszewski et al. Nucleic Acid Res. 16:10765-10782, 1988).

These studies disclose techniques in which genomic libraries are used to transform plant cells and the gene cloning is performed. However, they have not succeeded in capturing any unknown gene of the donor plants of the genomic libraries, nor in improving the plants by the introduction of the unknown genes. Given those techniques, it is still difficult to breed a new variety that is improved in agriculturally useful traits, particularly in traits whose expression will be improved in so-called heterosis or in quantitative traits.

Heterosis

Heterosis is a phenomenon in which the $F_1$ generation of a cross between inbred lines is superior to the parental lines. In heterosis, various trait improvements are recognized, such as higher vigor of the entire plant, larger plant and organs, higher yield, rapid growth, greater resistance to diseases and pests, greater resistance to various environmental stresses including drought, high temperature and cold temperature, increase or decrease in a specified component, and increase or decrease in a specified enzyme activity, and many of these traits are extremely advantageous in agriculture. A heterosis based breeding method that has been employed from old times in order to improve cultivated plants is $F_1$ hybrid breeding in which different parents are crossed to create a new variety and this has made great contribution to breeding superior varieties of many crops including maize. However, $F_1$ hybrid breeding requires a large number of steps such as development and improvement of the breeding population, the development of inbred lines, examination of general combining ability, examination of specific combining ability, and the selection of $F_1$ variety. In addition, each of these steps requires a lot of time and labor. What is more, while heterosis often produces great efficacy in the crossing of genetically distant parents, in the case where the relation between the parents is remote, crossing often does not produce fertility, thus limiting the range of species that can be crossed.

The molecular mechanism for heterosis is yet to be unraveled. Even the latest textbook on thremmatology states as follows: "the causal factors (in heterosis) at the physiological, biochemical, and molecular levels are today almost as obscure as they were at the time of the conference on heterosis held in 1952" (Genetics and Exploitation of Heterosis in Crops, p. 173, ed. Coors and Pandey, 1999, American Society of Agronomy, Inc. and Crop Science Society of America, Inc., Madison, Wis., U.S.A.)

Interesting reports on heterosis in maize were recently made. They are Fu and Dooner, Proc. Natl. Acad Sci USA 99:9573-9578, 2002 and Song and Messing, Proc Natl Acad Sci USA 100:9055-9060, 2003. In both reports, the authors investigated intervarietal differences in nucleotide sequence noting specific loci in maize, and consequently showed that the intervarietal differences were considerably greater than in self-fertilizing crops such as rice.

These findings are interesting because they show that in cross-fertilizing crops such as maize which tend to develop heterosis, the sequences of genomic DNA have greater intervarietal differences than in self-fertilizing crops; yet, it cannot be said they have reasonably unraveled the molecular mechanism for heterosis.

Thus, no insight has yet been gained into the mechanism for heterosis at the molecular level. However, at the level of classical genetics, it has been suggested that the following various genetic interactions are involved in heterosis.

A) Dominance Effect

Traits for which heterosis is observed are governed by a large number of loci in various linkage groups, and in each locus, an allele advantageous for survival and productivity is often considered to be dominant whereas a disadvantageous allele is recessive. Since there are many loci in linkage, it is almost impossible to obtain a plant line in which advantageous alleles are homozygous for all of such loci. However, $F_1$ plants can possess all the advantageous alleles from the parents so that heterosis is induced.

B) Over-Dominance Effect

In a large number of loci, the case where two alleles are heterozygous is sometimes more advantageous in survival and productivity than the case where the locus is homozygous, and the sum of such effects brings about heterosis.

If over-dominance effect exists in a locus having particularly great effect, one can observe heterosis due to the over-dominance effect of that single locus. This phenomenon is called single-gene heterosis or single-locus heterosis. Although not contributing to any particular phenotype in the original plant, this is a gene or locus that brings about a useful phenotypic variation by the interaction between genes in another plant. Known examples of genes or loci that exhibit such property are the alcohol dehydrogenase gene in maize (Schwartz, Theor Appl Genet 43:117-120, 1973) and the purple plant locus in maize (Hollick and Chandler, Genetics 150:891-897, 1998).

C) Interaction of Non-Allelic Genes

Traits advantageous for survival and productivity are sometimes brought about in $F_1$ hybrids as synergism between different genes. The sum of the effects of a large number of genes exhibiting such property brings about heterosis. The interaction between non-alleles is also called epistasis.

D) Interaction Between Nuclear Genes and Cytoplasmic Genes

Through the interaction between nuclear genes and cytoplasmic genes, traits advantageous for survival and productivity are sometimes expressed in $F_1$ hybrids.

The various types of interaction between multiple genes is considered to induce heterosis. Stuber (Plant Breeding Reviews 12:227-251, 1994) reviews a large number of references that show examples of the involvement of those types of interaction of genes and emphasizes that heterosis is governed by a large number of genetic factors. Li and Yuan (Plant Breeding Reviews 17:15-158, 2000) also consider that heterosis is caused by the combination of the above-mentioned various effects.

Thus, heterosis is governed by a large number of genetic factors, so it has been difficult for the prior art technology to breed a new variety that is further improved in traits whose expression is known to be higher in heterosis.

Quantitative Traits

Traits that can be improved in expression by heterosis are often "quantitative traits", and it is not easy to genetically analyze quantitative trait loci (QTL) which govern heterosis. Nevertheless, with the recent advances in molecular biological techniques, it has become possible to perform genetic analysis of QTL using DNA markers. As a matter of fact, there are cases for successful identification of chromosomal sites containing QTL that govern certain quantitative traits. In addition, studies are being made to clone agriculturally useful genes by molecular biological techniques using genetic maps.

In some organisms, many molecular markers have been identified on chromosomes to help construct genetic maps based on the linkage analysis of the markers. Their physical relative positions have also become clear by linking long cloned genomic DNAs.

In organisms for which genetic maps have been constructed, attempts to unravel the physical positions of genes that govern those traits and isolate such genes have been made by linkage analysis of traits that exhibit specified phenotypes and their markers, and subsequent chromosome walking. As a matter of fact, several genes have been isolated by this technique (map-based cloning).

However, in standard QTL analysis, a QTL-containing site can only be identified in an approximate manner and only DNA fragments theoretically harboring a large number of genes can be identified as QTL-containing DNA fragments. It is not easy to identify such fragments as those capable of being cloned or as those that can be introduced into a plant by transformation. In addition, the task of constructing a detailed genetic map, specifying a gene of interest on the basis of the map information and cloning the gene requires a considerable amount of time and labor. In fact, there are only few cases in which DNA fragments that could increase quantitative traits were cloned on the basis of QTL analysis.

Constructing Genomic DNA Libraries and the Technology of Transformation with Genomic Fragments The technology of constructing libraries of plant genomic fragments is known. Using transformation vectors that can be used to transform plants in the process is also known. For example, vectors are known that can be used for cloning large (40-80 kb) DNA fragments and which permit gene transfer into plants (Liu et al. Proc. Natl. Acad. Sci. USA 96:6535-6540, 1999). Experimental attempts have also been made to introduce plant genomic fragments as individual clones into higher plants. However, no one has ever made an attempt in such a way that a large number of genomic fragments that constitute a genomic DNA library are individually introduced into plants when the functions of these fragments are unknown.

It is also known that the use of a genomic clone sometimes results in a higher gene expression than when the corresponding cDNA clone is used. As a matter of fact, when a genomic fragment harboring a certain gene (maize phosphoenolpyruvate carboxylase) was introduced into a plant (rice), an extremely high-level expression of the foreign gene was observed (Ku et al. Nature Biotechnol. 17:76-80, 1999). Other reports relate to experiments in which three 40-80 kb genomic clones from *Arabidopsis* were individually transferred back into *Arabidopsis* (Liu et al. Proc Natl Acad Sci US 96:6535-6540, 1999; Shibata and Liu Trends in Plant Sci 5:354-357, 2000). Two of the clones were introduced into an *Arabidopsis* line that had lost gravitropism due to mutation at the locus contained in those clones and the recovery of the normal gravitropic response was confirmed.

The above findings suggest that genes in organisms, in particular, genes in multi-cell organisms are controlled with regard to their expression level in a complex way by temporal and spatial distributions of the genes in the organisms and environmental conditions such as external stimuli; in other words, the importance of a particular gene is determined by the time and extent of its expression as well as by the tissue and cell in which it is expressed, and the timing of its expression. Thus, in order to unravel gene functions including these sophisticated gene regulations, the promoter, intron, enhancer, structural gene, splicing site and all other extensive gene expression regulating factors that are contained in the genomic fragment of the particular gene must be clarified. However, this task requires a considerable amount of labor and time, making it difficult to unravel the interaction between many genetic factors Patent Document
 1: WO 03/018808 A
Non-Patent Document
1: Jordan et al. Trends in Plant Sciences 17:392-398, 2002
2: Dairi et al. Mol Gen Genet 262: 957-964, 2000
3: Klee et al. Mol Gen Genet 210:282-287, 1987
4: Olszewski et al. Nucleic Acid Res. 16:10765-10782, 1988
5: Genetics and Exploitation of Heterosis in Crops, p. 173, ed. Coors and Pandey, 1999, American Society of Agronomy, Inc. and Crop Science Society of America, Inc., Madison, Wis., U.S.A.
6: Fu and Dooner, Proc. Natl. Acad Sci USA 99:9573-9578, 2002
7: Song and Messing, Proc Natl Acad Sci USA 100:9055-9060, 2003
8: Schwartz, Theor Appl Genet. 43:117-120, 1973
9: Hollick and Chandler, Genetics 150:891-897, 1998
10: Stuber, Plant Breeding Reviews 12:227-251, 1994
11: Li and Yuan, Plant Breeding Reviews 17:15-158, 2000
12: Liu et al. Proc Natl Acad Sci USA 96:6535-6540, 1999
13: Ku et al. Nature Biotechnol. 17:76-80, 1999
14: Shibata and Liu Trends in Plant Sci 5:354-357, 2000

DISCLOSURE OF THE INVENTION

Problems to be Solved by the Invention

The present invention provides a method by which a large number of genomic DNA fragments capable of providing plants with an agriculturally advantageous phenotypic variation are efficiently screened and prepared as cloned DNA fragments.

The present invention also provides a method by which genomic DNA fragments that improve the expression of a trait whose expression is improved by more than one genetic factor are screened and prepared with high efficiency.

The present invention also provides a method for efficiently screening and preparing a large number of genomic DNA fragments, that can improve traits that are expressed in heterosis or quantitative traits, as cloned DNA fragments.

The present invention also provides a method for efficiently screening and preparing genomic DNA fragments capable of providing plants with a potentially agriculturally advantageous phenotypic variation, wherein the method does not require the great number of steps that are unavoidable in conventional techniques such as $F_1$ hybrid breeding, as exemplified by breeding and improving the breeding population, breeding of a inbred line, performance test on general combining ability, performance test on specific combining ability and the selection of $F_1$ variety and each of which requires a great length of time.

The present invention also provides a method for efficiently screening and preparing genomic DNA fragments capable of providing plants with a potentially agriculturally advantageous phenotypic variation by selecting superior individuals solely on the basis of the phenotype of the recipient plant into which the genomic DNA fragments have been introduced even if there is little information available about the mechanism of trait expression or about the individual of genes expressing the trait.

The present invention also provides a method for efficiently screening and preparing genomic DNA fragments enabling expression of a trait similar to that of an improved trait which occurs in heterosis (hereunder referred to as "heterosis-like expression") not only in plant varieties of the same species but also in plant varieties of different species.

The present invention also provides a method for efficiently screening and preparing a large number of genomic DNA fragments enabling heterosis-like expression in a short period without requiring a great amount of time and labor.

The present invention also provides a process for producing a plant having a potentially agriculturally advantageous phenotypic variation by transforming a plant with a genomic DNA fragment capable of providing it with a potentially agriculturally advantageous phenotypic variation or a genomic DNA fragment capable of inducing heterosis-like expression, both being prepared by the method of the present invention, as well as the plant produced by that process.

The present invention also provides a method for breeding a plant having a potentially agriculturally advantageous phenotypic variation by using as a marker either all or part of genomic DNA fragment capable of providing a plant with a potentially agriculturally advantageous phenotypic variation or genomic DNA fragment capable of inducing heterosis-like expression, both being prepared by the method of the present invention, as well as the plant produced by that method.

DESCRIPTION OF TERMS

In the present specification, "an agriculturally advantageous phenotypic variation" is "a phenotypic variation which causes a quantitative increase or decrease of a plant or a part of a plant, or an increase or decrease in growth rate of a plant or a part of a plant, in particular, in a cultivated plant species and/or an ornamental plant species under conditions of cultivation that are normal or favorable to the plant or under conditions which are somewhat stressful to the plant". The conditions that are stressful include the salinity of the growing site, high temperature, cold temperature, drought, diseases, pests, etc.

This is because such phenotypic variation gives rise to the trait of high yield if fruit, foliage, etc. increase under normal conditions of cultivation, while if the plant does not die under conditions where stress as from diseases and pests is imposed and its fruit, foliage, etc. increase as compared to the control plant, the phenotypic variation means resistance to the stress as from diseases and pests. The constituents of the plant, the enzymes contained in the plant, etc. are of course encompassed by the term "part of the plant". A decrease in the size of the entire plant or a part of the plant is often agriculturally beneficiary since dwarf plants are bred actively and cultivated widely.

Therefore, the concept of "a phenotypic variation which causes a quantitative increase or decrease of a plant or a part of a plant or an increase or decrease in growth rate of a plant or a part of a plant under certain conditions of cultivation" encompasses agriculturally advantageous phenotypic variations including, for example, higher vigor of the entire plant, larger plant and organs, higher yield, rapid growth, greater resistance to diseases and pests, greater resistance to various environmental stresses including drought, high temperature and cold temperature, increase or decrease in a specific component, increase or decrease in a specific enzymatic activity, and dwarfing, and so on.

In addition, the production of disease-free seedlings using tissue culture technology is also an important technology in agriculture, so it goes without saying that an improvement in the growth of cells in tissue culture is also an agriculturally advantageous phenotypic variation.

In the present invention, the term "screening or selection" shall also include the case where, after being subjected to a certain process of selection, the number of individual plants in a given population becomes zero, namely the case where the population proves to include no plant that complies with the criterion for selection. This is because, after such a selection, one can avoid inputting further labor and resources to the investigation of that population by knowing that a given population does not include any plants that comply with the criterion for selection.

Means for Solving the Problems

The present invention provides a method for screening genomic DNA fragments capable of providing plants with a potentially agriculturally advantageous phenotypic variation by the following steps (1) to (4) and optionally step (5).

(1) First, genomic DNA fragments are isolated from a plant by a conventional method, subjected to partial restrictive degradation and, after size fractionation, a genomic DNA library is constructed in the usual manner.

The plant as a donor of genomic DNA fragments is not limited in any particular way and preferred examples are plants that can produce heterosis by crossing with the plant as a recipient of the genomic DNA fragments. For example, if the recipient plant is Japonica rice, *Oryza rufigopon*, which is a wild rice, and Indica rice are preferred. If the recipient plant is a variety of maize, another variety of maize and teosinte, a wild species, are preferred examples of the donor plant. Generally, a greater extent of heterosis is observed in plants of more distant relationship. Heretofore, distant relationship impedes crossing, so it has been impossible to use heterosis from the combination with a plant of distant relationship; on the other hand, in the method of the present invention, genomic DNA fragments from a donor plant that cannot be used for crossing can easily be used, so even plants of distant relationship can be used as preferred donor plants.

Various vectors can be used as cloning vectors in constructing genomic libraries. Preferably, vectors that can be directly used in transformation of the recipient plant may be employed. For example, in order to transform rice, tobacco, *Arabidopsis*, etc. pSB200 and pCLD04541 (Tao and Zhang Nucleic Acid Res 26:4901-4909, 1998) may be used, and to transform maize, pSB25UNpHm may be used.

In the case of single-locus heterosis, the DNA fragments to be cloned may be of a sizes sufficient to contain at least one gene; however, in order to include the individual genes present in the genome and the regions required for regulating their expression, sizes of at least 1 kb are preferred, with sizes of at least 10 kb being more preferred, at least 20 kb being particularly preferred, and 30-40 kb being most preferred. Whichever the case, there is no particular upper limit on the size of the DNA fragments as long as they can be introduced into cloning vectors. Methods of partial restrictive degradation for obtaining such DNA fragments are known. The total number of clones that constitute a genomic DNA library, namely, the size of the library is preferably large enough to include as many genes in the plant genome as possible. Various enzymes may be used to effect partial restrictive degradation. For performing less deviated degradation, the use of 4-base recognizing restriction enzymes, such as, MboI and TaqI, is desirable. Methods for determining appropriate conditions for degradation are known and detailed disclosures may be found in Molecular Cloning, A Laboratory Manual, Third Edition, Cold Spring Harbor Laboratory Press, Cold Spring Harbor, N.Y., 2001.

Theoretically, the total number of clones for ensuring that a given genomic fragment is contained in a genomic DNA library of interest with a certain probability is calculated by the following formula:

$$N=\ln(1-P)/\ln(1-f)$$

(where
P is the probability that the given genomic fragment is contained in the genomic DNA library of interest;
f is the ratio of "the average length of the genomic fragments contained in the clones" to "the genome size of the original plant";
N is the total number of the genomic clones).

For example, in the case of a rice genomic DNA library, if the probability that a given genomic fragment is contained in the genomic DNA library is 70% and the average fragment length of the genomic DNA library is 40 kb, the formula goes like this:

$$N=\ln(1-0.7)/\ln[1-(40\times10^3/430\times10^6)]=1.3\times10^4$$

Hence, 13,000 clones are required.

The above calculation is simply intended to illustrate the significance of handling a large number of clones and it is in no way intended to show that a similar number of genomic clones must invariably be handled. Hence, it is possible that a smaller number of clones are investigated and yet at least one of the fragments under search may be found in those clones with considerably high probability, if more than one genomic DNA fragments in the genomic DNA library can provide plants with a potentially agriculturally advantageous phenotypic variation.

If the size of genomic fragments contained in individual clones is large, a smaller number of genomic fragments need to be investigated to acquire the fragments under search. On the other hand, if the genomic fragment size is small, subsequent handling steps such as cloning are easy to perform and the efficiency of transfer into the plant through transformation is also high. Factors such as the genome size of the plant to be handled and the scale of the experiment are determined after comprehensive review.

When handling a plant of larger genome size, one may advantageously use a technique that involves excluding methylated DNA fragments to increase the probability of DNA fragments containing expressible genes. Plants of larger genome size are believed to contain many unwanted DNAs that do not function as a gene and it is said that such DNAs are often methylated. Methods for biochemically removing methylated DNAs are known and removal of methylated DNAs is also possible if cloning is performed using *E. coli* having an ability to remove methylated DNAs (WO 00/50587).

After constructing the genomic DNA library, part of the clones that constitute the library are incorporated into *E. coli* for cultivation. The number of colonies that appear (in the case of a plasmid or cosmid vector) or plaques (in the case of a phage vector) is counted and on the basis of their counts, the total number of clones in the library is estimated. In addition, DNA is prepared from part of the colonies or phages that appeared, and the size of the cloned DNA fragments is measured to estimate the average fragment length.

(2) Genomic DNA that is contained in each of the clones that constitute the library is individually introduced into a plant.

If vectors that can be directly used in transformation of plants, such as pSB200, pCLD04541 and pSB25UNpHm, are employed, the individual clones may directly be subjected to an experiment of transformation. Otherwise, all or part of the DNA fragments contained in each clone may be transferred to a transformation vector before an experiment of transformation.

The donor plant to be used in transformation may be of a different species from the plant from which the genomic DNA is derived; alternatively, it may be a different variety of the same species or the same variety of the same species. Preferred examples of plants cover a substantially unlimited wide range including cereal plants such as rice, barley, wheat and maize, plants for producing luxuries such as coffee, cocoa, tea and tobacco, vegetables, fruits and ornamental plants such as flowers.

Transformation may be effected by any existing methods. Known examples are biological transfer such as *Agrobacterium*-mediated method, physical transfer such as microinjection, electroporation, particle bombardment, silicon carbide method and air injection, and chemical transfer such as polyethylene glycol method. By transformation, the genomic DNA is incorporated into the genome of the recipient plant.

According to the present invention, it has been found that it is not just one genomic DNA fragment that is obtained from a single plant genomic library and which can induce heterosis-like expression. Hence, in order to select a greater number of genomic fragments, it is desirable that as many genomic fragments as possible are individually introduced into a plant. In the screening method of the present invention, a certain preliminary step of selection may be included; however, in order to eliminate any deviation to occur in the chosen candidate fragments, it is desirable that the genomic DNA fragments to be introduced into the plant are not subjected to such a preliminary selection step before they are introduced into the plant.

Note that in the present invention, there is no need to have information about the genomic DNA fragments to be introduced, in particular, the phenotype with which said genomic DNA fragments are associated in the original plant. This is because it is not until the phenotype of the transgenic plant is selected that a useful genomic DNA fragment is specified.

Referring to each of the genomic clones to be introduced into the plant, at least part of them are amplified and/or stored. Storage may be performed by conventional methods in the form of purified DNA or bacterium (e.g. *E. coli*), yeast, etc. that contain the genomic clones.

(3) The transgenic plant into which the genomic fragments have been introduced are regenerated to a complete plant and cultivated.

The regenerated transgenic plants and their progeny plants are evaluated for various agriculturally advantageous traits including, for example, the vigor of the overall plant, the size and weight of the plant and individual organs, yield, growth rate, resistance to diseases and pests, resistance to various environmental stresses including drought, high temperature and cold temperature, increase or decrease in a specified component, and increase or decrease in a specified enzyme activity. Vigor means the activity of the plant taken as a whole or its ability to grow healthily.

In the present invention, the traits to be evaluated are independent of the characteristics of the plant which is a donor of the genomic DNA fragments and the genomic DNA fragments that are introduced and there is no limitation at all as long as they are agriculturally useful traits. Preferred are quantitative traits and traits that can be improved by heterosis, and more preferred are traits which prove agriculturally useful when the donor plant is regarded as the object to be bred.

After the evaluation test, those plants which are found to have exhibited a phenotypic variation compared with the plant into which none of the genomic fragments were introduced are selected. For example, one can select plants that show higher vigor of the overall plant, larger and heavier plant and individual organs, higher yield, rapid growth, greater resistance to diseases and pests, greater resistance to various environmental stresses including drought, high temperature and cold temperature, increase or decrease in a specified component, increase or decrease in a specified enzyme activity, etc. as compared with the plant into which none of the genomic fragments were introduced. The phenotypic variations to be selected for each trait are not limited to one direction. Consider, for example, the trait of dwarfness; it is an important agricultural trait that serves as a goal of breeding various crops, so as for the size of the plant and individual organs, plants that have become smaller than the plant into which none of the genomic fragments were introduced can be selected. This is also true with other traits.

Many of these traits are so-called quantitative traits and are greatly affected not only by genetic factors but also by environmental factors. Even in the case of the plant into which genomic fragments were not introduced, values of measurement show a distribution with some dispersion due, for example, to environmental factors. According to the present invention, in a population of plants into which genomic DNA fragments were randomly introduced, the distribution of measured values is expected to become broader if there exist genomic DNA fragments that bring about a phenotypic variation. By selecting the plants that present the values of measurement located at one or both ends of the distribution, one can obtain a smaller population including plants that contain genomic DNA fragments that bring about a phenotypic variation.

The thus obtained plant or each of the plants in a smaller population may be subjected to the evaluation of progeny plants and, further, to a repeated investigation of various traits, thereby evaluating the characteristics of the trait or traits that were found to have been expressed as a phenotypic variation, the mode of inheritance and the correlation with other traits; in addition, detailed evaluation can be made from the viewpoints of molecular biology, genetics, biochemistry and plant physiology. After various evaluations, the plant or plants may be agriculturally used as a novel variety. If a plant showing greater superiority in traits is obtained from those plants, the genomic DNA fragment introduced into that plant may be chosen as more valuable genomic DNA fragment.

In that case, the introduced genomic DNA fragment can be easily analyzed and acquired by conventional cloning methods.

(4) As mentioned before, the genomic DNA fragment introduced into the selected plant is separately stored as a genomic clone and the required amount can be produced by amplification in *E. coli* using a cloning vector or by biochemical amplification methods such as PCR and LAMP. Using such an amplified genomic DNA fragment, determination of the nucleotide sequence, analysis of the contained genes, intron and other genetic elements, etc. can be performed in detail. Since the genomic fragment can be introduced into any plants using known transformation techniques, the fragment can be utilized in variety improvement of a plant of dissimilar species from the plant of origin of the genomic DNA fragment, in improvement of a different variety of a plant of the same species, and in the breeding of the same variety of a plant of the same species.

(5) If necessary, all or part of the thus selected genomic DNA fragment may be re-introduced into a plant of the same or dissimilar species and subjected to similar evaluations, thereby effecting a step of secondary screening. In this case, transformation may be performed using the same cloning vector as employed in step (2) or by using a different cloning vector. If a different cloning vector is employed, the genomic DNA fragments selected in step (4) will be subcloned into the vector. The restriction sites to be used for cloning in the cloning vector differ from one cloning vector to another, so depending on what restriction enzymes are to be used, it is sometimes appropriate to perform subcloning of only part of the genomic DNA fragment selected in step (4). Further, the size of DNA fragments that can be cloned varies with the cloning vector or the method of cloning and for this reason, too, it is sometimes appropriate to perform subcloning of only part of the genomic DNA fragment. One of the advantages that result from using only part of the DNA fragment to perform the step of secondary screening is that if the transformation using only certain part of the DNA fragment shows that the result is the same as what was obtained by using all of the DNA fragment, it becomes clear that a certain part of the genomic DNA fragment selected in step (4) is unwanted. The transgenic plants obtained by the secondary transformation and their progeny plants are evaluated for various agriculturally advantageous traits including, for example, the vigor of the overall plant, the size and weight of the plant and individual organs, yield, growth rate, resistance to diseases and pests, resistance to various environmental stresses including drought, high temperature and cold temperature, increase or decrease in a specified component, and increase or decrease in a specified enzyme activity.

After the evaluation test, the genomic DNA fragments that gave rise to plants which exhibited a phenotypic variation compared with the plant into which none of the genomic fragments were introduced can create a preferred phenotypic variation in plants irrespective of the conditions for cultivation in the step of primary screening, the plant species, etc. and can be selected as a particularly preferred genomic DNA fragment. Again, as in the step of primary screening, one can select in the steps of secondary and subsequent screenings those plants which show higher vigor of the overall plant, larger and heavier plant and individual organs, higher yield, rapid growth, greater resistance to diseases and pests, greater resistance to various environmental stresses including drought, high temperature and cold temperature, increase or decrease in a specified component, increase or decrease in a specified enzyme activity, etc. as compared with the plant into which none of the genomic fragments were introduced.

The selected plants may be subjected to the evaluation of progeny plants and, further, to a repeated investigation of various traits, thereby evaluating the characteristics of the trait or traits that were found to have been expressed as a phenotypic variation, the mode of inheritance and the correlation with other traits. After various evaluations, the plants may be agriculturally used as a novel variety.

Secondary screening provides a genomic DNA fragment that has been verified to be capable of providing a plant with an agriculturally advantageous phenotypic variation even if it is introduced again into the plant, as well as a genomic DNA fragment that has been also verified to be capable of providing another plant with an agriculturally advantageous phenotypic variation. Hence, more valuable genomic DNA fragments will be chosen than when only the primary screening is applied.

This step of selection can be repeated as many times as one likes, to yield even more valuable genomic DNA fragments.

The transcripts of the genes contained in the selected genomic DNA fragment and cDNAs derived from the fragments may be analyzed and the characteristics of the genes deduced from the nucleotide sequences of the genomic DNA fragment may be analyzed in detail and comprehensively, as a result of which one can obtain findings that are useful in deducing the genetic functions contained in the genomic DNA fragment and unraveling the mechanism of inducing heterosis.

While the foregoing description of the present invention centers on the method of screening genomic DNA fragments, it also provides the thus selected genomic DNA fragments which are capable of providing plants with an agriculturally advantageous phenotypic variation, as well as a plant conferred with the agriculturally advantageous phenotypic variation by transformation with said genomic DNA fragment. Various methods are already known for introducing a specified DNA fragment into plant cells or a plant tissue, forming calli from the cells or tissue, cultivating the calli and causing them to regenerate into a complete plant. See, for example, Hiei et al. Plant J. 6:271-282, 1994. In some plants, the plant may be regenerated from transgenic cells without passing through noticeable callus formation and the present invention is also effective in that case. The regenerated plant may be fixed as a variety in accordance with the method described in Maruta et al. Molecular Breeding 8:273-284, 2001.

The present invention also relates to a method of using the genomic DNA fragment of the invention as a marker in the improvement of a plant variety. In other words, a plant having the genomic DNA fragment of the invention can be used to enhance the efficiency of improvement of a plant variety. The use of the plant for the improvement of a plant variety may be embodied in such a way that said plant serves as a donor plant introducing the genomic DNA fragment of the invention into another plant or as a parental plant for performing variety improvement through breeding by crossing. For instance, a plant known to have the genomic DNA fragment of the invention may be crossed with a plant variety to be improved and a genomic DNA preparation is prepared from the individual progeny plant; and subsequent steps of selecting an individual progeny plant that contains the genomic DNA fragment of the invention in said genomic DNA preparation and using a specific sequence information in the genomic DNA fragment to employ it as a marker are known procedures, as typically described in Komori et al. Euphytica 129:241-247, 2003. Speaking further of use as a marker, the whole genomic DNA fragment may be employed as a marker or, alternatively, if part of said genomic DNA fragment contains a characteristic sequence, the sequence of that part may be used as a marker.

The genomic DNA fragments according to the present invention include isolated, biologically active DNA and RNA that hybridize under low or high stringency conditions to the nucleotide sequences of the genomic fragments obtained by the methods disclosed in the present specification. Conditions for hybridization under high stringency may be exemplified by the following which are described in Molecular Cloning, etc.: hybridization in 0.5 M sodium phosphate (pH 7.2), 1 mM EDTA, 7% SDS and 1% BSA at 65° C., followed by washing in 40 mM sodium phosphate buffer (pH 7.2), 1 mM EDTA, 5% SDS and 0.5% BSA at 65° C., then washing in 40 mM sodium phosphate buffer (pH 7.2), 1 mM EDTA and 1% SDS at 65° C. Conditions for hybridization under moderate stringency may be exemplified by the following: hybridization in 0.5 M sodium phosphate (pH 7.2), 1 mM EDTA, 7% SDS and 1% BSA at 55° C., followed by two washings in 40 mM sodium phosphate buffer (pH 7.2), 1 mM EDTA, 5% SDS and 0.5% BSA at 55° C. for 15 minutes, then two washings in 40 mM sodium phosphate buffer (pH 7.2), 1 mM EDTA and 1% SDS at 55° C. for 15 minutes. Alternatively, as described in Molecular Cloning, hybridization in 30% deionized formamide, 0.6 M NaCl, 40 mM sodium phosphate (pH 7.4), 2.5 mM EDTA and 1% SDS at 42° C. may be followed by two washings in 2×SSC and 0.1% SDS at room temperature for 10 minutes and one-hour washing in the same buffer at 55° C. These, however, are not the sole conditions that can be adopted in the present invention.

ADVANTAGEOUS EFFECT OF THE INVENTION

In the methods of the present invention for screening genomic DNA fragments, it is possible to search for DNA fragments involved in heterosis by a new approach that requires no previous unraveling of the functions of plant genes, while such unraveling has been necessary in conventional methods for genome analysis as exemplified by a comparison with known nucleotide sequences and production of the cDNA function.

In the methods of the present invention for screening genomic DNA fragments, DNA fragments associated with agriculturally useful traits are searched for by a new approach that does not need any information about the genomic DNA fragments to be introduced, in particular, the phenotype with which said genomic DNA fragments are associated in the original plant.

In the methods of the present invention for screening genomic DNA fragments, there is no limit on the traits to be selected and choice can be made from a wide range of agriculturally useful traits.

In the methods of the present invention for screening genomic DNA fragments, genomic DNA fragments are selected by the phenotype of the recipient plant, so the genomic DNA fragments that are chosen can be directly used in the breeding of the recipient plant.

In the methods of the present invention for screening genomic DNA fragments, genomic DNA fragments that induce an effect similar to heterosis can be obtained as DNA fragments that are cloned and which can be easily introduced into a plant by transformation, so the great amount of time and labor that has been required in the use of heterosis in classical methods of plant breeding can be dispensed with.

In the methods of the present invention for screening genomic DNA fragments, unlike the use of heterosis in classical methods of plant breeding, a genomic fragment from one variety is introduced into another variety, so the reproductive barriers between the parental varieties do not take effect and the combination of plants that have impeded the conventional $F_1$ hybrid breeding becomes practicable. Hence, the DNA fragments of the present invention can be easily introduced by transformation into various plants for use in breeding, irrespective of whether they are of the same or different species than the plant from which the DNA fragments originate; as a result, the advantages of heterosis can be utilized in a short period with high efficiency.

Furthermore, unlike QTL analysis, the methods of the present invention for screening genomic DNA fragments have no need to search for loci that are involved in agricultural traits, so genomic DNA fragments that increase or decrease quantitative traits can be selected efficiently without requiring a considerable amount of time and labor.

As a further advantage, the genomic DNA fragments of the present invention are capable of inducing heterosis-like expression, so if they are used as a marker in conventional methods of breeding by crossing, the selection efficiency on the progeny of crossing can be significantly increased.

BRIEF DESCRIPTION OF THE DRAWINGS

The patent or application file contains at least one drawing executed in color. Copies of this patent or patent application publication with color drawing(s) will be provided by the office upon request and payment of the necessary fee.

FIG. 8 shows sites of PCR amplification on a genomic DNA fragment of *Oryza rufipogon*.

FIG. 9 is a set of photographs showing some examples of PCR amplification as performed on a genomic DNA fragment of *Oryza rufipogon*.

FIG. 10 is a photograph showing electrophoretic patterns of restriction enzyme-cleaved fragments from a genomic DNA fragment of *Oryza rufipogon*.

FIG. 11 is a photograph showing electrophoretic patterns of restriction enzyme-cleaved fragments from a transformation vector containing a genomic DNA fragment of *Oryza rufipogon*.

EXAMPLES

Figure 1:
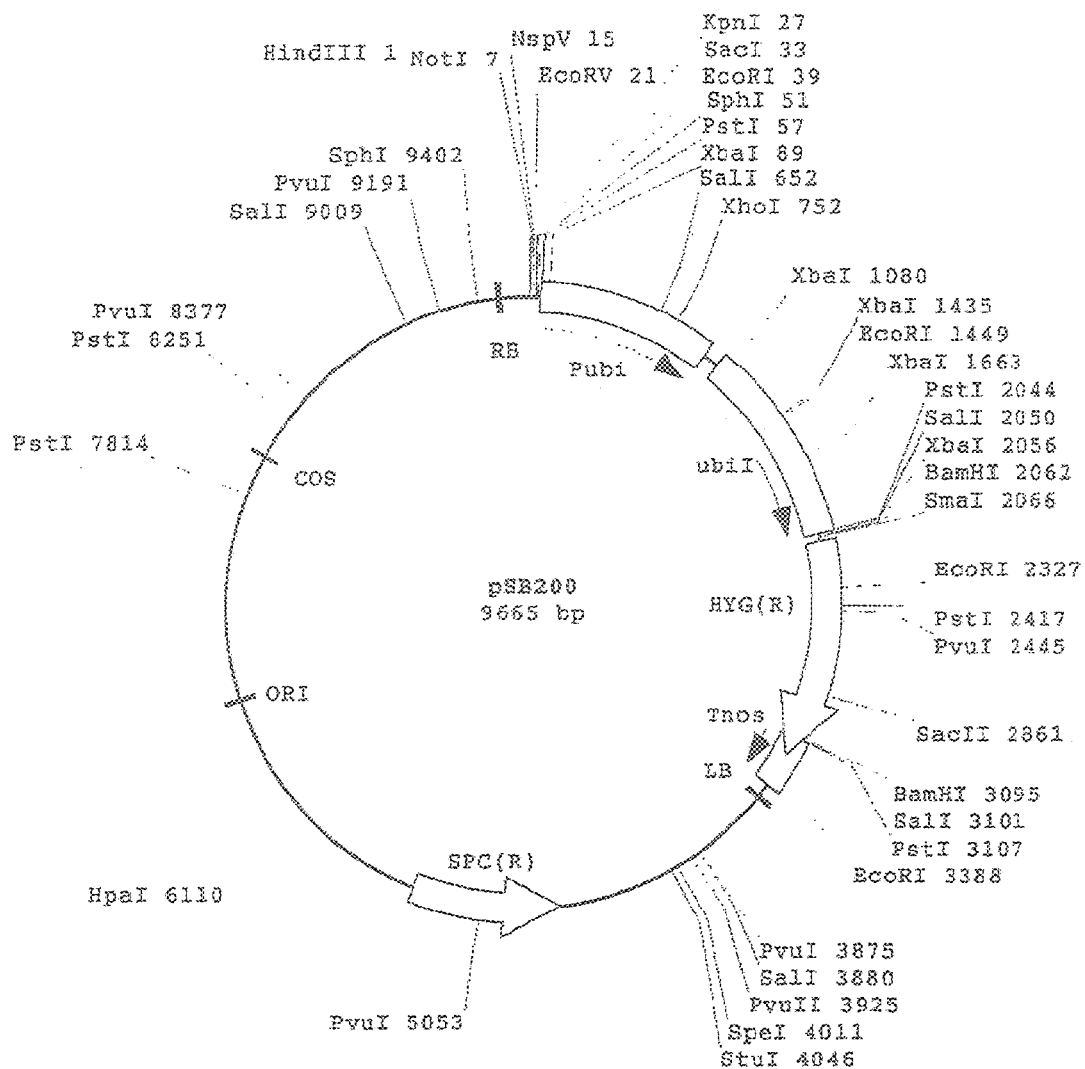
FIG. 1 is a genetic map of cloning vector pSB200.
Figure 2:
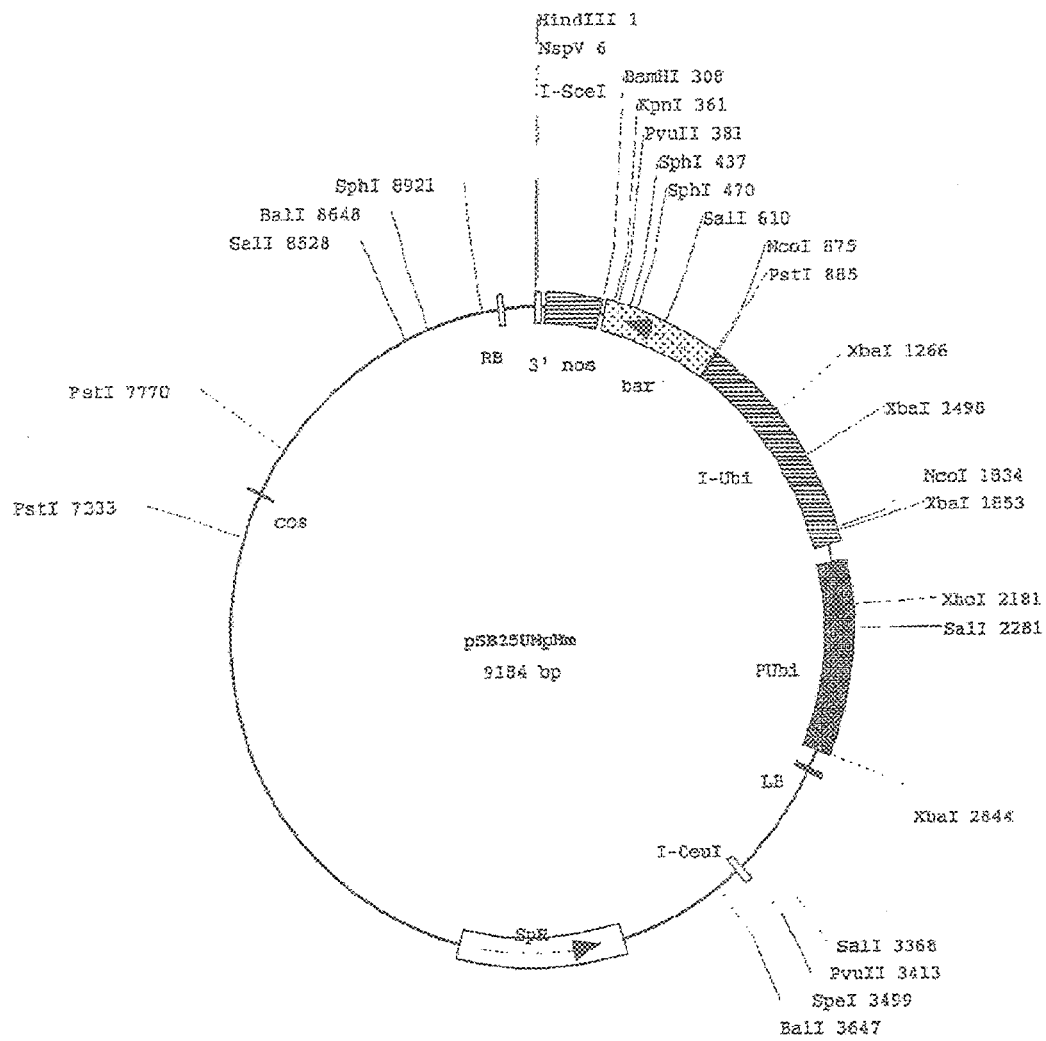
FIG. 2 is a genetic map of cloning vector pSB25UNpHm.

In the following examples, details of experimental procedures are, unless otherwise indicated, described in Current Protocols in Molecular Biology, John Wiley & Sons, Inc. (Supplements up to No. 59, July 2002, are included) or Molecular Cloning, A Laboratory Manual, Third Edition, Cold Spring Harbor Laboratory Press, Cold Spring Harbor, N.Y., 2001.

Example 1

Extraction of Genomic DNA from *Oryza rufipogon* and Construction of Genomic DNA Library Seeds of *Oryza rufipogon*, an allied species of rice, were obtained from National Institute of Agrobiological Sciences and planted for cultivation in a greenhouse. From leaves of the plants, genomic DNA was extracted in the usual manner. The extracted genomic DNA was subjected to partial restrictive degradation with restriction enzyme TaqI and, thereafter, fractions of 30 kb to 50 kb were prepared by sucrose density gradient centrifugation. Using those fractions, cloning was made at the site of cleavage in cosmid vector pSB200 by Nsp(7524)V (hereunder sometimes designated simply as NspV) to construct a genomic DNA library.

The vector pSB200 was a cloning vector constructed from the pSB11 described in Komari et al. (Plant J. 10:165-174, 1996). To be specific, a maize ubiquitin promoter was connected before a hygromycin resistance gene and the 3' terminal signal of NOS gene. A Nsp(7524)V cleavage site was added to the construct, which was then inserted into pSB11 thereby to construct pSB200. Using pSB200, one can construct a genomic DNA library having an average fragment length of about 40 kb. Speaking further of pSB200, it is also a transformation vector for higher plants and can be used for gene transfer into various plants with the hygromycin resistance gene used as a selection marker.

Most of the DNA fragments cloned in the library had sizes from about 30 kb to about 50 kb and the total number of clones was about 80,000. The *E. coli* strains used were DH5α and GeneHogs.

Example 2

Transformation of Japonica Rice with the Clones Constituting the *Oryza rufipogon* Derived Genomic DNA Library The clones constituting the genomic DNA library derived from *Oryza rufipogon* were individually transferred into the *Agrobacterium* strain LBA4404(pSB1) (Komari et al. 1996). The method used for transfer was triparental mating (Ditta et al. Proc Natl Acad. Sci. U.S.A. 77:7347-7351, 1980). The resulting *Agrobacterium* carrying the clones were individually introduced into rice (variety: Yukihikari). The method of transformation was in accordance with Hiei et al. (1994) and based on inoculation of immature embryos with *Agrobacterium*. The immature embryos of the variety Yukihikari were obtained from plants cultivated in a greenhouse after sowing grains of unpolished rice marketed for food, or from their progeny plants cultivated in the greenhouse.

As a result, transgenic plants were obtained into which a total of 5310 genomic DNA fragments from the *Oryza rufipogon* derived genomic DNA library had been individually introduced. For each genomic DNA fragment, 1-5 individuals of independent transformant plants were obtained. Hereinafter, the transgenic plants of the current generation will be referred to as T0 generation plants and their progeny as T1 generation, T2 generation and so on, according to the general rule.

If these results are substituted into the formula set forth above, $5310 = \ln(1-P)/\ln[1-(40 \times 10^3/430 \times 10^6)]$ and, hence $P=0.39$. Therefore, the probability that a given *Oryza rufipogon* derived genomic DNA fragment is contained in those 5310 genomic DNA fragments is 39%.

Example 3

Figure 3:
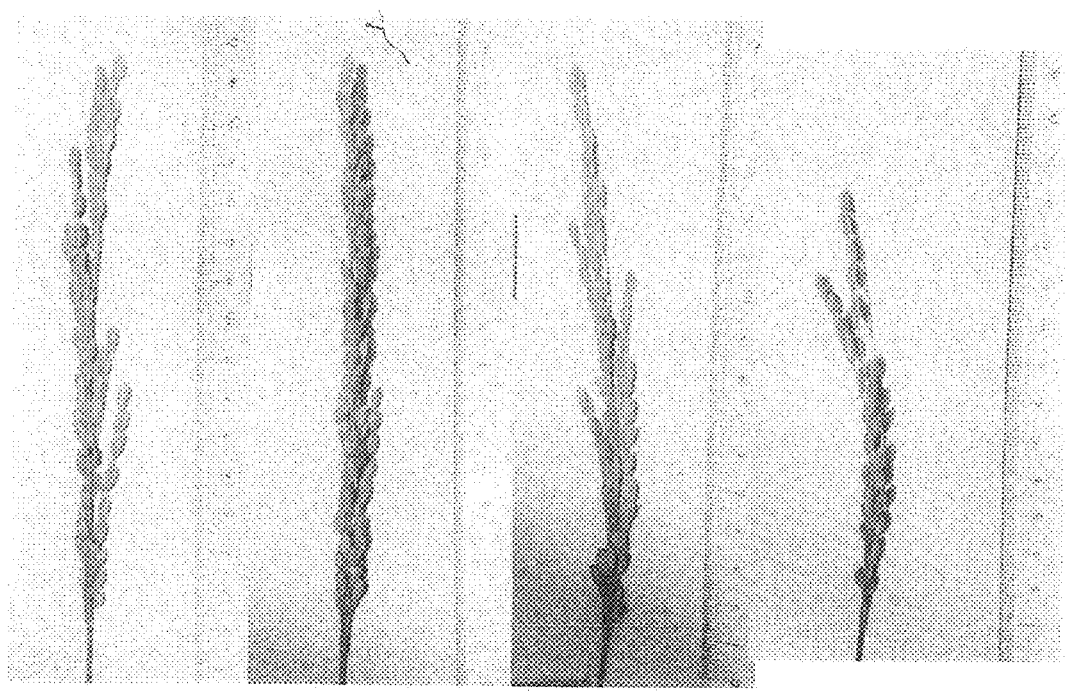
FIG. 3 is a set of photographs showing some transgenic plant specimens selected on the basis of the external observation of panicle size, the number of grains in one panicle and the vigor of the plant, as compared with a control plant (generation: T0, number of screened lines: 5310).

Evaluation of Japonica Rice Transformed with the Genomic DNA Fragments from the *Oryza rufipogon* Derived Genomic DNA Library and Selection of Plants that Exhibited Phenotypic Variation The transgenic plants were cultivated in a greenhouse and the respective individuals were investigated for the vigor of the plant taken as a whole, plant length, relative growth rate, number of panicles, shoot weight, panicle weight, panicle length, number of fertile grains, and yield. In the present specification, relative growth rate refers to the amount of daily growth per unit plant length and is determined by the formula: ((plant length at the day the investigation was completed minus plant length at the day the investigation was started)/the period of investigation in days)/plant length at the day the investigation was started. After the investigation, the plants that were found to have exhibited a phenotypic variation in any trait as compared with the control plant were selected. Tables 1 to 6 and FIG. 3 show the selected plant specimens and the names conferred to the genomic DNA fragments that were introduced. In those specimens, more than one of the transformants into which the same genomic fragment had been introduced showed a similar phenotypic variation and hence were selected. For each genomic fragment, the average of the measured values for the selected plants is listed. The plants that were selected on the basis of the external observation of the vigor of the plant taken as a whole also had, in many cases, exhibited a variation in a certain numeric value of measurement. Each of the specimens shown below was selected on the basis of the vigor of the plant taken as a whole and a certain numeric value of measurement.

In the following cases, the distribution of measured values for the control plant was fit to a normal distribution. The control plant was rice (Yukihikari) that was transformed with GUS gene. In accordance with the normal distribution and on the hypothesis that the introduced fragments were not effective, the probability that a line showing the values of measurement for the selected transgenic plant lines would appear was calculated. In each case, the probability of appearance among the screened lines was extremely small and the expected value for the appearance of those selected lines was by far smaller than 1.0. Therefore, the hypothesis for the non-effectiveness of the introduced fragments was rejected and it was statistically demonstrated that the selected lines showed a significant phenotypic variation.

TABLE 1

Transgenic plant specimens selected on the basis of plant length and the overall vigor of the plant at day 14 after transplantation, as compared with the control plant (generation: T0, number of screened lines: 846)

|  | Genomic DNA fragemt introduced | Number of individuals investigated | Average of measured values | Probability* | Remarks |
|---|---|---|---|---|---|
| Selected transgenic plant | A029B04 (SEQ ID NO: 1 SEQ ID NO: 2) | 5 | 38.8 | 0.000007 | Average for independent transgenic plants |
| Selected transgenic plant | A028C04 (SEQ ID NO: 3 SEQ ID NO: 4) | 4 | 39 | 0.00003 | |
| Control plant | | 311 | 28.2 | | SD: 7.58 |

*Probability for the occurrence of the line of interest on the hypothesis for non-effectiveness of introduced fragments

TABLE 2

Transgenic plant specimens selected on the basis of plant length and the overall vigor of the plant at day 21 after transplantation, as compared with the control plant (generation: T0, number of screened lines: 931)

|  | Genomic DNA fragment introduced | Number of individuals investigated | Average of measured values | Probability* | Remarks |
|---|---|---|---|---|---|
| Selected transgenic plant | A029B04 (SEQID NO: 1 SEQ ID NO: 2) | 5 | 50.6 | 0.0003 | Average for independent transgenic plants |
| Selected transgenic plant | A028C04 (SEQ ID NO: 3 SEQ ID NO: 4) | 4 | 52 | 0.0003 | |
| Selected transgenic plant | A048F12 (SEQ ID NO: 5 SEQ ID NO: 6) | 5 | 51.8 | 0.0008 | |
| Control plant | | 336 | 42.7 | | SD: 8.58 |

*Probability for the occurrence of the line of interest on the hypothesis for non-effectiveness of introduced fragments

TABLE 3

Transgenic plant specimens selected on the basis of relative growth rate and the overall vigor of the plant from day 14 to day 21 after transplantation, as compared with the control plant (generation: T0, number of screened lines: 841

|  | Genomic DNA fragment introduced | Number of individuals investigated | Average of measured values (cm) | Probability* | Remark |
|---|---|---|---|---|---|
| Selected transgenic plant | A049A01 (SEQ ID NO: 7 SEQ ID NO: 8) | 1 | 0.224 | 0.00002 | Average for independent transgenic plants |
| Selected transgenic plant | A046A06 (SEQ ID NO: 9 SEQ ID NO: 10) | 3 | 0.136 | 0.00006 | |
| Selected transgenic plant | A045B09 (SEQ ID NO: 11 SEQ ID NO: 12) | 3 | 0.141 | 0.00007 | |
| Control plant | | 306 | 0.076 | | SD: 0.036 |

*Probability for the occurrence of the line of interest on the hypothesis for non-effectiveness of introduced fragments

TABLE 4

Transgenic plant specimens selected on the basis of shoot weight and the overall vigor of the plant in the stage of maturity, as compared with the control plant (generation: T0, number of screened lines: 1464)

| | Genomic DNA fragment introduced | Number of individuals investigated | Average of measured values (g) | Probability* | Remark |
|---|---|---|---|---|---|
| Selected transgenic plant | A049A07 (SEQ ID NO: 13 SEQ ID NO: 14) | 5 | 6.24 | 0.0000005 | Average for independent transgenic plants |
| Selected transgenic plant | A040D06 (SEQ ID NO: 15 SEQ ID NO: 16) | 5 | 6.4 | 0.0000002 | |
| Selected transgenic plant | A048F12 (SEQ ID NO: 5 SEQ ID NO: 6) | 5 | 6.33 | 0.0000007 | |
| Control plant | | 558 | 3.56 | | SD: 1.78 |

*Probability for the occurrence of the line of interest on the hypothesis for non-effectiveness of introduced fragments

TABLE 5

Transgenic plant specimens selected on the basis of ear weight and the overall vigor of the plant at day 14 after transplantation, as compared with the control plant (generation: T0, number of screened lines: 1464

| | Genomic DNA fragment introduced | Number of individuals investigated | Average of measured values (g) | Probability* | Remark |
|---|---|---|---|---|---|
| Selected transgenic plant | A036A03 (SEQ ID NO: 17 SEQ ID NO: 18) | 5 | 0.98 | 0.00005 | Average for independent transgenic plants |
| Selected transgenic plant | A051E08 (SEQ ID NO: 19 SEQ ID NO: 20) | 3 | 1.17 | 0.00001 | |
| Selected transgenic plant | A023D09 (SEQ ID NO: 21 SEQ ID NO: 22) | 2 | 1.31 | 0.00009 | |
| Control plant | | 558 | 0.55 | | SD: 0.30 |

*Probability for the occurrence of the line of interest on the hypothesis for non-effectiveness of introduced fragments

TABLE 6

Transgenic plant specimens selected on the basis of ear length and the overall vigor of the plant, as compared with the control plant (generation: T0, number of screened lines: 1464)

| | Genomic DNA fragment introduced | Number of individuals investigated | Average of measured values (cm) | Probability* | Remark |
|---|---|---|---|---|---|
| Selected transgenic plant | A030B02 (SEQ ID NO: 23 SEQ ID NO: 24) | 5 | 14.4 | 0.00005 | Average for independent transgenic plants |
| Selected transgenic plant | A043F04 (SEQ ID NO: 25 SEQ ID NO: 26) | 5 | 13.5 | 0.00005 | |
| Selected transgenic plant | A049E02 (SEQ ID NO: 27 SEQ ID NO: 28) | 2 | 15.9 | 0.00009 | |
| Control plant | | 557 | 12.3 | | SD: 1.85 |

*Probability for the occurrence of the line of interest on the hypothesis for non-effectiveness of introduced fragments The plants as the progeny of the transgenic plants were also cultivated and evaluated as described above. In the T1 generation, the individuals containing the introduced genomic DNA fragments were anticipated to segregate from the individuals containing no such fragments according to Mendel's first law, so investigation was made to check for the presence or absence of an introduced fragment by polymerase chain reaction (PCR).

Tables 7 to 9 that follow show the selected plant specimens and the names conferred to the genomic DNA fragments that were introduced. In those specimens, the plants that were the progeny derived from the same transgenic plant and in which the presence of an introduced fragment was verified by PCR all showed a similar phenotypic variation. The plants in which no introduced fragment was detected by PCR all failed to show a comparable phenotypic variation. Each of the specimens shown below was selected on the basis of the vigor of the plant taken as a whole and a certain numeric value of measurement.

In the following cases, the distribution of measured values for the control plant was fit to a normal distribution. The control plant was yet to be transformed Yukihikari. In accordance with the normal distribution and on the hypothesis that the introduced fragments were not effective, the probability that a line showing the values of measurement for the selected transgenic plant lines would appear was calculated. In each case, the probability of appearance among the lines to be selected was extremely small and the expected value for the appearance of those selected lines was by far smaller than 1.0. Therefore, the hypothesis for the non-effectiveness of the introduced fragments was rejected and it was statistically demonstrated that the selected lines showed a significant phenotypic variation.

TABLE 7

Transgenic plant specimens selected on the basis of plant length and the overall vigor of the plant at day 14 after transplantation, as compared with the control plant (generation: T1, number of screened lines: 114)

|  | Genomic DNA fragment introduced | Number of individuals investigated | Average of measured values (cm) | Porbability* | Remark |
| --- | --- | --- | --- | --- | --- |
| Selected transgenic plant | A010C09 (SEQ ID NO: 27 SEQ ID NO: 28) | 7 | 61.7 | 0.001 | By PCR, all individuals were verified to have incorporated a fragment |
| Selected transgenic plant | A011C02 (SEQ ID NO: 31 SEQ ID NO: 32) | 7 | 62.5 | 0.0001 | |
| Selected transgenic plant | A010B03 (SEQ ID NO: 33 SEQ ID NO: 34) | 5 | 60.4 | 0.002 | |
| Control plant | | 84 | 58.5 | | SD: 3.5 |

*Probability for the occurrence of the line of interest on the hypothesis for non-effectiveness of introduced fragments

TABLE 8

Transgenic plant specimens selected on the basis of plant length and the overall vigor of the plant at day 21 after transplantation, as compared with the control plant (generation: T1, number of screened lines: 114)

|  | Genomic DNA fragment introduced | Number of individuals investigated | Average of measured values (cm) | Probability* | Remark |
| --- | --- | --- | --- | --- | --- |
| Selected transgenic plant | A010C09 (SEQ ID NO: 29 SEQ ID NO: 30) | 7 | 69 | 0.001 | By PCR, all individuals were verified to have incorporated a fragment |
| Selected transgenic plant | A011C02 (SEQ ID NO: 31 SEQ ID NO: 32) | 6 | 71 | 0.000008 | |
| Selected transgenic plant | A010B03 (SEQ ID NO: 33 SEQ ID NO: 34) | 5 | 71 | 0.000006 | |
| Selected transgenic plant | A009F06 (SEQ ID NO: 35 SEQ ID NO: 36) | 7 | 70.6 | 0.00003 | |
| Selected transgenic plant | A009E11 (SEQ ID NO: 37 SEQ ID NO: 38) | 5 | 70.4 | 0.00003 | |
| Control | | 84 | 66.1 | | SD: 3.4 |

*Probability for the occurrence of the line of interest on the hypothesis for non-effectiveness of introduced fragments

TABLE 9

Transgenic plant specimens selected on the basis of relative growth rate and the overall vigor of the plant from day 14 to day 21 after transplantation, as compared with the control plant (generation: T1, number of screened lines: 114)

|  | Genomic DNA fragment introduced | Number of individuals investigated | Average of measured values (cm) | Probability* | Remark |
| --- | --- | --- | --- | --- | --- |
| Selected transgenic plant | A010B03 (SEQ ID NO: 33 SEQ ID NO: 34) | 7 | 0.032 | 0.00002 | By PCR, all individuals were verified to have incorporated |
| Selected transgenic | A008B02 (SEQ ID NO: 39 | 7 | 0.024 | 0.002 | |

TABLE 9-continued

Transgenic plant specimens selected on the basis of relative growth rate and the overall vigor of the plant from day 14 to day 21 after transplantation, as compared with the control plant (generation: T1, number of screened lines: 114)

| | Genomic DNA fragment introduced | Number of individuals investigated | Average of measured values (cm) | Probability* | Remark |
|---|---|---|---|---|---|
| plant | SEQ ID NO: 40) | | | | a fragment |
| Control plant | | 84 | 0.018 | | SD: 0.007 |

*Probability for the occurrence of the line of interest on the hypothesis for non-effectiveness of introduced fragments Example 4

Screening of Transgenic Plants on the Basis of Evaluation of Disease Resistance

The T1 generation plants of transgenic lines that were created in Example 2 were evaluated for blast resistance in comparison with two control plants, untransformed Yukihikari and Koshihikari, and the plants that were found to have a phenotypic variation in a blast resistance related trait were selected. In addition, the genomic DNA fragments introduced into those plants were selected as genomic DNA fragments capable of providing plants with a potentially agriculturally advantageous phenotypic variation.

Each line was sown in a closed-system greenhouse and seedlings at day 12 after sowing were transplanted for cultivation in a growth chamber, KOITOTRON (KOITO MFG. CO., LTD.) Nine individuals of each control variety and 5-9 individuals per transgenic line were inoculated with *Magnaporthe grisea*, a rice blast causing pathogen, and the degree of the disease was, evaluated to select resistant lines.

Inoculum was prepared in the following way. A colony of *Magnaporthe grisea* strain TSU-01 was inoculated to an oatmeal-agar medium (Difco) containing 10 g/l of sucrose and cultivated at 26° C. in the dark for 3 weeks. For conidium formation, sterile distilled water (10 ml) was added to the plate and after cutting hyphae with a sterilized painting brush, cultivation was continued at 25° C. for 3 days under illumination. Eight milliliters of an LB liquid medium (Difco) diluted to one half the initial concentration with sterile distilled water was put into the plate and conidia were suspended with a sterile painting brush. After filtering the suspension through dual-layered gauze, the concentration of conidia was adjusted to about $2 \times 10^6$ conidia/ml. Immediately before inoculation, Silwet L-77 was added to the inoculum to give a final concentration of 0.01%.

Inoculation was performed by applying the inoculum, with a painting brush, to the topmost expanded leaves of the plant at day 19 after transplantation. Immediately after the application, the inoculated leaves were passed through plastic tubes, each of which was plugged with cotton swab at both top and bottom openings which was then fully wetted with distilled water. Cultivation was performed for one week, with light on for 14 hours at 25° C. during the day and at 20° C. during the night. In the process, the cotton swab at the openings of each tube were wetted with distilled water once a day. The inoculated leaves were cut off and the number and area of lesions were assessed by the following criteria for the degree of the disease: 0 (no symptom) to 3 (lesion spread to cover most of the leaves).

In susceptible variety "Koshihikari", a large number of lesions formed on many leaves. The degree of the disease was 1.5 on average. Compared to "Koshihikari", moderately blast resistant "Yukihikari" had formed fewer lesions and the degree of the disease was 0.8 on average.

Figure 4:
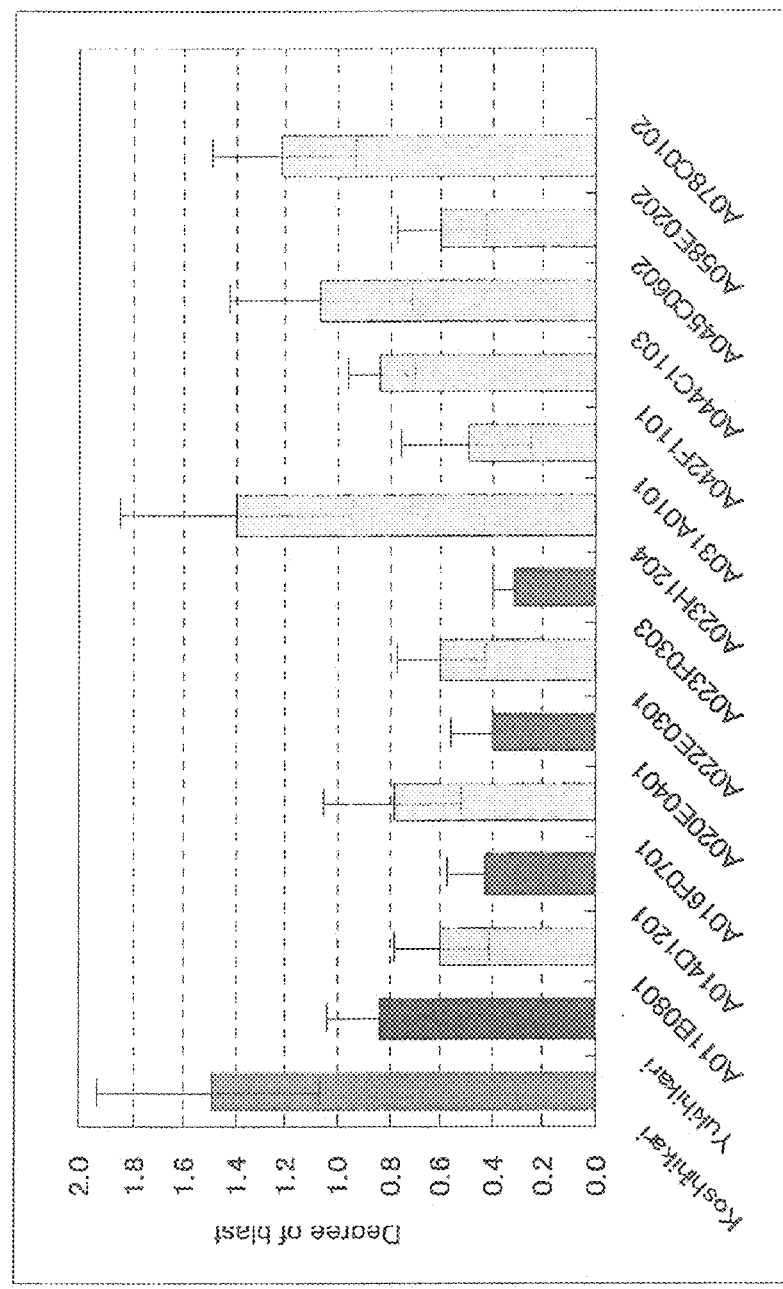
FIG. 4 is a graph showing the results of a blast resistance test of transgenic rice specimens selected after introducing genomic DNA fragments of *Oryza rufipogon*.

In Example 4, check for the presence or absence of an introduced fragment was made on the basis of the hygromycin sensitivity of laminas sampled from each individual. Individuals having no hygromycin resistance, or individuals having no introduced fragment, were removed as segregated individuals and comparison was made for the average degree of the disease on the transgenic individuals. Many of the transgenic lines showed a comparable degree of the disease to the untransformed control "Yukihikari". Data is shown below for 13 transgenic lines. A014D1201, A020E0401, A023F0303 and A078C0102 showed significantly lower degrees of the disease than the control "Yukihikari" (FIG. 4). In particular, the degree of the disease on A078C0102 was zero on average, showing the possibility that the introduction of *Oryza rufipogon* genomic fragments had conferred a high level of blast resistance.

Example 5

Screening of Transgenic Plants on the Basis of Evaluation of Drought Resistance

Of the T1 generation plants of transgenic lines that were created in Example 2, 4872 lines were evaluated for the resistance to drying stress in comparison with two control plants, untransformed Yukihikari and Sue won 287 which had been reported as an drought resistant variety (and obtained from the National Institute of Agrobiological Sciences), and plants that were found to have a phenotypic variation in a trait related to the resistance towards drying stress were selected. Each line was sowed on seedling raising boxes in a closed-system greenhouse and, after 10 days, hygromycin resistance testing was done by leaf detachment to check for the presence or absence of an introduced fragment in each individual. Individuals that showed hygromycin resistance, namely, those individuals which were estimated to contain introduced fragments were planted on pots 12 cm in diameter and 10 cm high (POLYPOT of Tokai Kasei Co., Ltd.). For ridging, a paddy rice seedling raising soil (INGS) was used and a total of 8 individuals were planted per pot, 6 of them were transformants and 2 were control plants. The number of individuals tested was between 12 and 18 (on 2-3 pots) per variety or line. Two weeks after planting (4 weeks after sowing), the supply of water was stopped to start the application of drying stress.

After one week, the transgenic plants were evaluated for their resistance to drought. Evaluation was made visually on each individual by 5 scores [ranging from 0 (died) to 5 (complete recovery)]. In order to correct any scattering in data between pots, the score of each individual under test was adjusted by subtracting the score of Yukihikari on the same pot. On the basis of the thus obtained results of evaluation, the top 10% of the transformants were selected as plants containing genomic fragments highly likely to confer drought resistance to crops.

Figure 5:
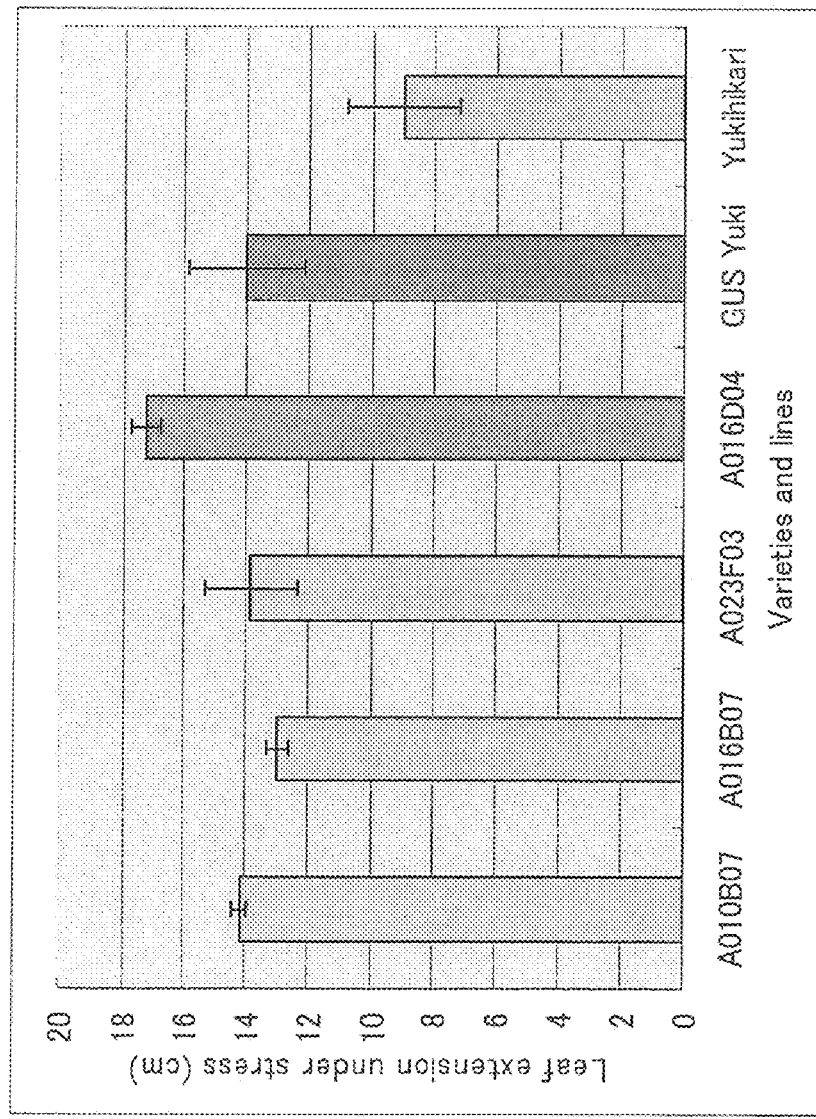
FIG. 5 is a graph showing the growth of leaves in transgenic rice specimens selected after introducing genomic DNA fragments of *Oryza rufipogon* extended under stress.

Of the above-described transgenic plants, four potentially promising lines were measured for the length of the topmost leaf on each individual immediately before the drying treatment and one week after the treatment. The leaf length measured one week after the treatment minus the value measured immediately before the treatment was used as the amount of leaf extension of each individual under drying stress. After the leaf length measurement, water supply was resumed and after four days, the degree of recovery was investigated to evaluate the amount of leaf extension under drying stress. Evaluation was made in the same manner as described above, except that Yukihikari (T2) having only GUS gene transferred to it was added as a control plant. To check to see if the distribution of scores on each line would differ from the distribution of scores on Yukihikari, the Kolmogorov-Smirnov test was applied in analysis. On the basis of the results thus obtained, one of the four lines of transformants under test was selected as a line that showed a significantly greater leaf extension than the control plants under drying stress (FIG. 5).

Example 6

Evaluation of Maize Transformed with the Genomic DNA Fragments Contained in *Oryza rufipogon* Derived Genomic DNA Library and Selection of Plants Having Phenotypic Variation Transformation of maize was performed using *Agrobacterium* containing the *Oryza rufipogon* derived genomic fragments that were created in Example 1. Transformation procedures were in accordance with Ishida et al (2003, Plant Biotechnol. 20:57-66). The recipient variety was inbred A188 (available from the National Institute of Agrobiological Sciences). As in Example 1, a genomic DNA library was constructed using pSB25UNpHm as a vector; also created was *Agrobacterium* containing the *Oryza rufipogon* derived genomic DNA fragments. Using the library and *Agrobacterium*, transformation of maize was performed in the same manner as described above. As a result, transgenic plants were obtained into which a total of 108 genomic DNA fragments contained in the *Oryza rufipogon* derived genomic DNA library had been individually introduced. The vector pSB25UNpHm was the same as the pSB25 described in Ishida et al. Nature Biotech 14:745-750, 1996, except that the promoter of bar gene was replaced by a maize derived ubiquitin promoter and that three additional cleavage sites of Nsp(7524)V, I-SceI and I-CeuI were conferred. The vector pSB25UNpHm has a comparable cloning ability to pSB200 and can be used for gene transfer into maize and various other plants with the bar gene used as a selection marker.

Transgenic plants of the current generation (T0 plants) were cultivated in a greenhouse as in the case of rice and the effectiveness of the introduced genomic DNA fragments was assessed by investigating the plant length at days 28 and 35 after transplantation, relative growth rate (((plant length at day 35 after transplantation minus plant length at day 28 after transplantation)/7)/plant length at day 28 after transplantation), lamina length at ear bearing nodes, largest ear's weight, number of grains in largest ear, total grain weight in largest ear, and single grain weight (total grain weight in largest ear divided by the number of grains in largest ear). In order to correct the seasonal unevenness in growth, the average was calculated for all individuals that were potted on the same day and analysis was made after normalizing the data by the formula (value of each individual−average)/average. A maize variety (A188) transformed with GUS gene was used as a control plant. Among the traits of the T0 plants, the total grain weight in largest ear and the single grain weight had significantly greater variances than those of the control plant. This showed that the population of the plants into which the genomic DNA fragments had been introduced had a greater spread in distribution of measured values.

In the following cases (Tables 10-13), the distribution of measured values for the control plant was fit to a normal distribution. In accordance with the normal distribution and on the hypothesis that the introduced fragments were not effective, the probability that a line showing the values of measurement for the selected transgenic plant lines would appear was calculated. In each case, the probability of appearance among the screened lines was extremely small and the expected value for the appearance of those selected lines was by far smaller than 1.0. Of the 108 lines that were investigated for the total grain weight in the largest ear, 5 lines had expected values smaller than 1.0. Therefore, the hypothesis for the non-effectiveness of the introduced fragments was rejected and it was statistically demonstrated that the selected lines showed a significant phenotypic variation.

The obtained transgenic maize was cultivated in a greenhouse, pollinated with the pollen of the maize variety A188 grown in a separate greenhouse, and seeds were obtained. For the purpose of the present invention, the generation derived from those seeds is designated T1 generation. For this generation T1, 5 to 8 individuals of each line were cultivated in a greenhouse and investigated for their traits. In the T1 generation, the individuals containing the introduced genomic DNA fragments were anticipated to segregate from the individuals containing no such fragments according to Mendel's first law, so investigation was made to check for the presence or absence of an introduced fragment by polymerase chain reaction (PCR). Using PCR, one can check for the presence or absence of an introduced fragment (for details, see Example 16). As the result of comparing the presence or absence of an improved fragment with the values of the traits investigated, the inventors could identify lines in each of which the averages of plant length and relative growth rate for the individuals containing the introduced genomic fragments were higher than those for all individuals in that line (Table 14).

On the basis of the results thus obtained, the transgenic plants that were found to have a phenotypic variation in one or more traits and their progeny plants were selected. In addition, the genomic DNA fragments introduced into those plants were selected as genomic DNA fragments capable of providing maize with a potentially agriculturally advantageous phenotypic variation.

TABLE 10

Transgenic plant (maize) specimens selected on the basis of relative growth rate (generation: T0, number of screened lines: 108, data normalized due to data integration over more than two potting days)

| | Genomic DNA fragment introduced | Number of individuals investigated | Average of measured values (as normalized) | Probability* |
|---|---|---|---|---|
| Selected transgenic plant | A030E08 | 2 | 0.227 | 0.00249 |

*Probability for the occurrence of the line of interest on the hypothesis for non-effectiveness of introduced fragments

TABLE 11

Transgenic plant (maize) specimens selected on the basis of largest ear's weight (generation: T0, number of screened lines: 108, data normalized due to data integration over more than two potting days)

|  | Genomic DNA fragment introduced | Number of individuals investigated | Average of measured values (as normalized) | Probability* |
|---|---|---|---|---|
| Selected transgenic plant | A011B09 | 4 | 0.480 | 4.2383E−11 |
| Selected transgenic plant | A015E08 | 7 | 0.482 | 0.00011 |
| Selected transgenic plant | A027D06 | 2 | 0.207 | 0.00659 |
| Selected transgenic plant | A033A09 | 3 | 0.133 | 0.00843 |

*Probability for the occurrence of the line of interest on the hypothesis for non-effectiveness of introduced fragments

TABLE 12

Transgenic plant (maize) specimens selected on the basis of total grain weight in largest ear (generation: T0, number of screened lines: 108, data normalized due to data integration over more than two potting days)

|  | Genomic DNA fragment introduced | Number of individuals investigated | Average of measured values (as normalized) | Probability* |
|---|---|---|---|---|
| Selected transgenic plant | A015E08 | 7 | 0.501 | 1.3063E−06 |
| Selected transgenic plant | A011B09 | 2 | 0.247 | 0.00127 |

TABLE 12-continued

Transgenic plant (maize) specimens selected on the basis of total grain weight in largest ear (generation: T0, number of screened lines: 108, data normalized due to data integration over more than two potting days)

|  | Genomic DNA fragment introduced | Number of individuals investigated | Average of measured values (as normalized) | Probability* |
|---|---|---|---|---|
| Selected transgenic plant | A033A09 | 3 | 0.093 | 0.00162 |
| Selected transgenic plant | A012H12 | 2 | 0.279 | 0.00910 |

*Probability for the occurrence of the line of interest on the hypothesis for non-effectiveness of introduced fragments

TABLE 13

Transgenic plant (maize) specimens selected on the basis of the number of grains in largest ear (generation: T0, number of screened lines: 108, data normalized due to data integration over more than two potting days)

|  | Genomic DNA fragment introduced | Number of individuals investigated | Average of measured values (as normalized) | Probability* |
|---|---|---|---|---|
| Selected transgenic plant | A011B09 | 4 | 0.519 | 1.2832E−08 |
| Selected transgenic plant | A033A09 | 3 | 0.129 | 0.00113 |
| Selected transgenic plant | A015E08 | 7 | 0.460 | 0.00186 |

*Probability for the occurrence of the line of interest on the hypothesis for non-effectiveness of introduced fragments

TABLE 14

Relation between the presence or absence of genomic DNA fragments and traits as assessed with reference to the marker created from selected genomic DNA fragments

| | | | | | | | | | | | Average for all individuals | Average for fragment-containing individuals |
|---|---|---|---|---|---|---|---|---|---|---|---|---|---|
| Plant length at week 4 | A019D09 | fragment* | − | + | + | + | + | − | | | | | |
| | | (cm) | 63 | 64 | 64 | 67 | 68 | 47 | | | 62.17 | 65.75 |
| Plant length at week 5 | A010A11 | fragment* | − | − | − | − | + | + | + | − | Average for all individuals | Average for fragment-containing individuals |
| | | (cm) | 89 | 85 | 82 | 97 | 97 | 95 | 94 | 87 | 90.75 | 95.33 |
| Plant length at week 5 | A019D09 | fragment* | − | + | + | + | + | − | | | Average for all individuals | Average for fragment-containing individuals |
| | | (cm) | 88 | 94 | 95 | 94 | 110 | 76 | | | 92.83 | 98.25 |
| Plant length at week 6 | A019D09 | fragment* | − | + | + | + | + | − | | | Average for all individuals | Average for fragment-containing individuals |
| | | (cm) | 105 | 118 | 118 | 116 | 132 | 95 | | | 114 | 121 |
| Relative growth rate at weeks 4-5 | A019A06 | fragment* | + | + | − | − | + | | | | Average for all individuals | Average for fragment-containing individuals |
| | | | 0.06 | 0.08 | 0.05 | 0.05 | 0.08 | | | | 0.066 | 0.074 |

TABLE 14-continued

Relation between the presence or absence of genomic DNA fragments and traits as assessed with reference to the marker created from selected genomic DNA fragments

| Relative growth rate at weeks 5-6 | A014A12 | fragment* | – | – | + | + | – | – | Average for all individuals | Average for fragment-containing individuals |
|---|---|---|---|---|---|---|---|---|---|---|
| | | | 0.02 | 0.03 | 0.04 | 0.04 | 0.02 | 0.04 | 0.032 | 0.04 |

*Presence or absence of genomic DNA fragment

Example 7

Evaluation of Tobacco Transformed with the Genomic DNA Fragments Contained in *Oryza rufipogon* Derived Genomic DNA Library and Selection of Plants Having Phenotypic Variation Transformation of tobacco was performed using *Agrobacterium* containing the *Oryza rufipogon* derived genomic DNA fragments that were created in Example 1. Transformation procedures were in accordance with Komari (Theor Appl Genet. 80:167-171, 1990). The recipient variety was SR1 (Kodama et al. Plant Physiol 105:601-605, 1994).

Figure 6:
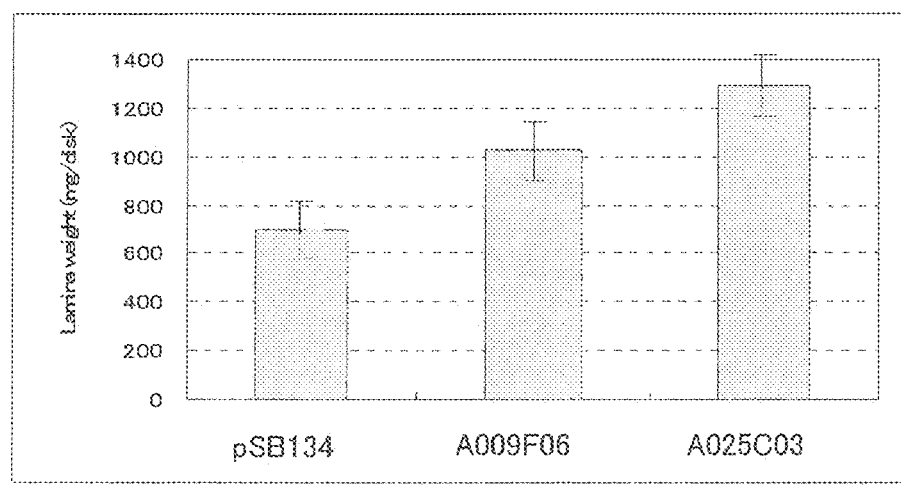
FIG. 6 is a graph showing the effect of the introduction of genomic DNA fragments on the growth of callus in transgenic tobacco specimens selected after introducing genomic DNA fragments of *Oryza rufipogon*.

The weight of calli produced from the transformed tobacco cells was measured to investigate how the growth of calli would be influenced by the *Oryza rufipogon* derived genomic DNA fragments. Tobacco leaves were bored through with a cork borer to prepare lamina disks, which were used in transformation. The control was disks of tobacco lamina that had been transformed with vector pSB134 having only the hygromycin resistance gene and the GUS gene. *Agrobacterium* was inoculated with those genomic DNA fragments, cultivated on a medium for 20 days, and the weight of each lamina disk with callus formation was measured. As FIG. 6 shows, genomic DNA fractions could be selected that showed more active callus growth than the control.

The transgenic plants and their progeny were cultivated in a greenhouse as in the case of rice and maize and the effectiveness of the introduced genomic DNA fragments was assessed by investigating the vigor of the plant taken as a whole, plant length, relative growth rate, number of leaves, leaf length, leaf width, leaf weight, shoot weight, yield, drought resistance, salt tolerance, and disease resistance. The transgenic plants that were found to have a phenotypic variation in one or more of the traits listed above and their progeny were selected. In addition, the genomic DNA fragments introduced into those plants were selected as genomic DNA fragments capable of providing tobacco with a potentially agriculturally advantageous phenotypic variation.

The thus selected 14 lines of transgenic plant were acclimatized and potted on 4-inch pots, then cultivated in a greenhouse as in the case of rice and maize, and investigated for the length of largest leaf (2 and 3 weeks after potting), natural plant height (3 weeks after potting), and culm length. The tobacco variety SR1 transformed with GUS gene was used as a control plant. As it turned out, many of the transgenic individuals were superior to the control plant in the length of largest leaf at week 2 after potting ($\chi^2$ test, P=0.00012).

TABLE 15

Frequency distribution of lamina length of largest transgenic plant (tobacco) leaf at week 2 after potting

| | No. of individuals | |
|---|---|---|
| Range of lamina length of largest leaf | Genomic fragment containing transgenic p:lants | Control |
| 0-17 cm | 218 | 22.673* |
| 18- cm | 14 | 5.23* |

*refers to expected value as determined from the actual segregation ratio

In the following cases (Tables 16-18), the distribution of measured values for the control plant was fit to a normal distribution. In accordance with the normal distribution and on the hypothesis that the introduced fragments were not effective, the probability that an individual showing the values of measurement for the selected transgenic plant individuals would appear was calculated. In each case, the probability of appearance among the individuals to be screened was extremely small and the expected value for the appearance of those selected individuals was by far smaller than 1.0. Therefore, the hypothesis for the non-effectiveness of the introduced fragments was rejected and it was statistically demonstrated that the selected individuals showed a significant phenotypic variation.

TABLE 16

Specimens of transgenic plant (tobacco) selected on the basis of the length of largest leaf at week 2 after transplantation as compared with control plant (generation: T0, No. of individuals to be screened: 172, calculation made on the basis of the upper 70% distribution of control plant) (individuals of low rooting ability would distort the distribution, so the lower 30% was excluded)

| | Genomic DNA fragment introduced | Measured value | Probability* |
|---|---|---|---|
| Selected transgenic plant | A010C09 | 15.7 | 0.02738 |
| Selected transgenic plant | A011C02 | 16.5 | 0.00964 |
| Selected transgenic plant | A009E11 | 17 | 0.00463 |
| Control plant (upper 70%) | | Average 12.03 | SD: 1.91 |

*Probability for the occurrence of the line of interest on the hypothesis for non-effectiveness of introduced fragments

TABLE 17

Specimens of transgenic plant (tobacco) selected on the basis of the length of largest leaf at week 3 after transplantation as compared with control plant (generation: T0, No. of individuals to be screened: 172, calculation made on the basis of the upper 70% distribution of control plant) (individuals of low rooting ability would distort the distribution, so the lower 30% was excluded)

|  | Genomic DNA fragment introduced | Measured value | Probability* |
|---|---|---|---|
| Selected transgenic plant | A011C02 | 24.3 | 0.00321 |
| Selected transgenic plant | A009E11 | 23.9 | 0.00590 |
| Control plant (upper 70%) |  | Average 19.05 | SD: 1.93 |

*Probability for the occurrence of the line of interest on the hypothesis for non-effectiveness of introduced fragments

TABLE 18

Specimens of transgenic plant (tobacco) selected on the basis of natural plant height at week 3 after transplantation as compared with control plant (generation: T0, No. of individuals to be screened: 172, calculation made on the basis of the upper 70% distribution of control plant) (individuals of low rooting ability would distort the distribution, so the lower 30% was excluded)

|  | Genomic DNA fragment introduced | Measured value | Probability* |
|---|---|---|---|
| Selected transgenic plant | A011C02 | 40 | 0.00480 |
| Control plant (upper 70%) |  | Average 20.74 | SD: 7.44 |

*Probability for the occurrence of the line of interest on the hypothesis for non-effectiveness of introduced fragments

Example 8

Evaluation of Rice Transformed with the Genomic DNA Fragments Contained in *Arabidopsis* Derived Genomic DNA Library and Selection of Plants Having Phenotypic Variation As in the case of *Oryza rufipogon*, genomic DNA was isolated from *Arabidopsis* (*Arabidopsis thaliana*), a genomic DNA library was constructed, and the genomic clones constituting the library were individually introduced into rice (Yukihikari) by transformation. As a result, transgenic plants were obtained into which a total of 1477 genomic DNA fragments in the genomic DNA library had been introduced individually. The ecotype of the *Arabidopsis* used in Example 8 was Columbia and its seeds are available from an international *Arabidopsis* gene resource bank (say, RIKEN Bioresource Center). The transgenic plants and their progeny were cultivated in a greenhouse as in the case of the *Oryza rufipogon* derived genomic DNA library and the effectiveness of the introduced genomic DNA fragments was assessed by investigating the vigor of the plant taken as a whole, plant length, relative growth rate, number of panicles, shoot weight, panicle weight, panicle length, number of fertile grains, yield, number of leaves, leaf length, leaf width, leaf weight, drought resistance, salt tolerance, and disease resistance. The rice variety Yukihikari transformed with GUS gene was used as a control plant. The transgenic plants that were found to have a phenotypic variation in one or more of the traits listed above and their progeny were selected. In addition, the genomic DNA fragments introduced into the selected plants were selected as *Arabidopsis* derived genomic DNA fragments capable of providing crops with a potentially agriculturally advantageous phenotypic variation.

In the following case (Table 19), the distribution of measured values for the control plant was fit to a normal distribution. In accordance with the normal distribution and on the hypothesis that the introduced fragments were not effective, the probability that a line showing the values of measurement for the selected transgenic plant lines would appear was calculated. In each case, the probability of appearance among the screened lines was extremely small and the expected value for the appearance of those selected lines was by far smaller than 1.0. Of the 1477 lines that were investigated for the total panicle weight, 13 lines had expected values smaller than 1.0. Therefore, the hypothesis for the non-effectiveness of the introduced fragments was rejected and it was statistically demonstrated that the selected lines showed a significant phenotypic variation.

TABLE 19

Transgenic plant (rice) specimens selected on the basis of total panicle weight as compared with control plant (generation: T0, number of screened lines: 1477)

|  | Genomic DNA fragment introduced | No. of Individuals | Average of measured values | Probability* |
|---|---|---|---|---|
| Selected transgenic plant | G009G04 | 2 | 4.75 | 3.65973E−06 |
| Selected transgenic plant | H008C01 | 2 | 4.71 | 6.25678E−06 |
| Selected transgenic plant | H003E08 | 2 | 4.54 | 2.27417E−05 |
| Selected transgenic plant | G001B04 | 2 | 4.33 | 3.47921E−05 |
| Control plant |  | 99 | 1.73 | SD: 1.10 |

*Probability for the occurrence of the line of interest on the hypothesis for non-effectiveness of introduced fragments

Example 9

Evaluation of Rice Transformed with the Genomic DNA Fragments Contained in Rhodes Grass Derived Genomic DNA Library and Selection of Plants Having Phenotypic Variation As in the case of *Oryza rufipogon*, genomic DNA was isolated from Rhodes grass (*Chloris gayana*), a genomic- DNA library was constructed, and the genomic clones constituting the library were individually introduced into rice (Yukihikari) by transformation. As a result, transgenic plants were obtained into which a total of 1450 genomic DNA fragments in the genomic DNA library had been introduced individually. The variety of Rhodes grass used in Example 9 is commercially available in the name of Callide. The transgenic plants and their progeny were cultivated in a greenhouse as in the case of the *Oryza rufipogon* derived genomic DNA library and the effectiveness of the introduced genomic DNA fragments was assessed by investigating the vigor of the plant taken as a whole, plant length, relative growth rate, number of panicles, shoot weight, panicle weight, panicle length, number of fertile grains, yield, number of leaves, leaf length, leaf width, leaf weight, drought resistance, salt tolerance, and disease resistance. The rice variety Yukihikari transformed with GUS gene was used as a control plant. The transgenic plants that were found to have a phenotypic variation in one or more of the traits listed above and their progeny were selected. In addition, the genomic DNA fragments introduced into the selected plants were selected as Rhodes grass derived genomic DNA fragments capable of providing crops with a potentially agriculturally advantageous phenotypic variation.

In the following case (Table 20), the distribution of measured values for the control plant was fit to a normal distribution. In accordance with the normal distribution and on the hypothesis that the introduced fragments were not effective, the probability that a line showing the values of measurement for the selected transgenic plant lines would appear was calculated. In each case, the probability of appearance among the screened lines was extremely small and the expected value for the appearance of those selected lines was by far smaller than 1.0. Of the 905 lines that were investigated for the total panicle weight, 23 lines had expected values smaller than 1.0. Therefore, the hypothesis for the non-effectiveness of the introduced fragments was rejected and it was statistically demonstrated that the selected lines showed a significant phenotypic variation.

Example 10

Evaluation of Rice and Maize Transformed with the Genomic DNA Fragments Contained in *Sorghum* Derived Genomic DNA Library and Selection of Plants Having Phenotypic Variation As in the case of *Oryza rufipogon*, genomic DNA was isolated from sorghum (*Sorghum bicolor*), a genomic DNA library was constructed, and the genomic clones constituting the library were individually introduced into rice (Yukihikari) and maize (A188) by transformation. As a result, transgenic plants were obtained in two groups, into which 2560 and 200 genomic DNA fragments in the genomic DNA library had been respectively introduced individually. The variety of sorghum used in Example 10 is commercially available in the name of gold sorgho. The transgenic plants and their progeny were cultivated in a greenhouse as in the case of the *Oryza rufipogon* derived genomic DNA library and the effectiveness of the introduced genomic DNA fragments was assessed by investigating the vigor of the plant taken as a whole, plant length, relative growth rate, number of ears, shoot weight, ear weight, ear length, number of fertile grains, yield, number of leaves, leaf length, leaf width, leaf weight, drought resistance, salt tolerance, and disease resistance. The transgenic plants that were found to have a phenotypic variation in one or more of the traits listed above and their progeny were selected. In addition, the genomic DNA fragments introduced into the selected plants were selected as sorghum derived genomic DNA fragments capable of providing crops with a potentially agriculturally advantageous phenotypic variation.

Shown below is a case for the total panicle weight of rice (Table 21). In the following case, the distribution of measured values for the control plant was fit to a normal distribution. The rice variety Yukihikari transformed with GUS gene was used as a control plant. In accordance with the normal distribution and on the hypothesis that the introduced fragments were not effective, the probability that a line showing the values of measurement for the selected transgenic plant lines would appear was calculated. In each case, the probability of appearance among the lines to be selected was extremely small and the expected value for the appearance of those selected lines was by far smaller than 1.0. Of the 2504 lines that were investigated for the total panicle weight, 43 lines had expected values smaller than 1.0. Therefore, the hypothesis for the non-effectiveness of the introduced fragments was rejected and it was statistically demonstrated that the selected lines showed a significant phenotypic variation.

TABLE 20

Transgenic plant (rice) specimens selected on the basis of total panicle weight as compared with control plant (generation: T0, number of screened lines: 905)

|  | Genomic DNA fragment introduced | No. of Individuals investigated | Average of measured values | Probability* |
| --- | --- | --- | --- | --- |
| Selected transgenic plant | C045H09 | 4 | 3.545 | 2.26464E−09 |
| Selected transgenic plant | C043D11 | 3 | 3.443 | 1.0617E−07 |
| Selected transgenic plant | C042B08 | 5 | 2.714 | 4.29802E−07 |
| Selected transgenic plant | C040G05 | 4 | 2.985 | 5.42953E−07 |
| Selected transgenic plant | C047A12 | 5 | 2.836 | 2.76644E−06 |
| Control plant |  | 109 | 1.588 | SD: 0.95196 |

*Probability for the occurrence of the line of interest on the hypothesis for non-effectiveness of introduced fragments

TABLE 21

Transgenic plant (rice) specimens selected on the basis of total panicle weight as compared with control plant (generation: T0, number of screened lines: 2504)

|  | Genomic DNA fragment introduced | No. of individuals investigated | Average of measured values | Probability* |
|---|---|---|---|---|
| Selected transgenic plant | E003G10 | 5 | 3.308 | 1.7166E−15 |
| Selected transgenic plant | E004G09 | 5 | 2.486 | 1.23902E−09 |
| Selected transgenic plant | E005C07 | 5 | 2.376 | 5.1179E−09 |
| Selected transgenic plant | E005B11 | 5 | 2.9 | 1.53413E−08 |
| Selected transgenic plant | E048H09 | 2 | 4.235 | 5.0472E−08 |
| Control plant |  | 157 | 1.48255 | SD: 0.84700 |

*Probability for the occurrence of the line of interest on the hypothesis for non-effectiveness of introduced fragments After introducing sorghum fractions, transgenic maize plants of the current generation were subjected to analysis of variance on the following traits: the plant length at days 28 and 35 after transplantation, relative growth rate (((plant length at day 35 after transplantation minus plant length at day 28 after transplantation)/7)/plant length at day 28 after transplantation), lamina length at ear bearing nodes, largest-ear's weight, number of grains in largest ear, total grain weight in largest ear, and single grain weight (total grain weight in largest ear divided by the number of grains in largest ear). The relative growth rate, number of grains in largest ear and single grain weight had significantly greater variances than those of the control plant. In order to correct the seasonal unevenness in growth, the average was calculated for all individuals that were potted on the same day and analysis was made after normalizing the data by the formula (value of each individual−average)/average.

In the following cases (Tables 22-27), the distribution of measured values for the control plant was fit to a normal distribution. A maize variety (A188) transformed with GUS gene was used as a control plant. In accordance with the normal distribution and on the hypothesis that the introduced fragments were not effective, the probability that a line showing the values of measurement for the selected transgenic plant lines would appear was calculated. In each case, the probability of appearance among the screened lines was extremely small and the expected value for the appearance of those selected lines was by far smaller than 1.0. Of the 150 lines investigated, 7 lines had expected values smaller than 1.0 for relative growth rate and 8 lines did so for the number of grains in the largest ear. Therefore, the hypothesis for the non-effectiveness of the introduced fragments was rejected and it was statistically demonstrated that the selected lines showed a significant phenotypic variation.

On the basis of those results, the genomic DNA fragments derived from sorghum were selected as genomic DNA fragments capable of providing maize with a potentially agriculturally advantageous phenotypic variation.

TABLE 22

Transgenic plant (maize) specimens selected on the basis of plant length at day 28 after transplantation (generation: T0, number of screened lines: 150, data normalized due to data integration over more than two potting days)

|  | Genomic DNA fragment introduced | No. of individuals investigated | Average of measured values (normalized) | Probability* |
|---|---|---|---|---|
| Selected transgenic plant | F001D10 | 2 | 0.085 | 0.00335 |

*Probability for the occurrence of the line of interest on the hypothesis for non-effectiveness of introduced fragments

TABLE 23

Transgenic plant (maize) specimens selected on the basis of relative growth rate (generation: T0, number of screened lines: 150, data normalized due to data integration over more than two potting days)

|  | Genomic DNA fragment introduced | No. of individuals investigated | Average of measured values (normalized) | Probability* |
|---|---|---|---|---|
| Selected transgenic plant | F004D08 | 3 | 0.088 | 0.00000 |
| Selected transgenic plant | F006B11 | 1 | 0.001 | 0.00082 |
| Selected transgenic plant | F004B08 | 2 | 0.412 | 0.00099 |

TABLE 23-continued

Transgenic plant (maize) specimens selected on the basis of relative growth rate (generation: T0, number of screened lines: 150, data normalized due to data integration over more than two potting days)

|  | Genomic DNA fragment introduced | No. of individuals investigated | Average of measured values (normalized) | Probability* |
|---|---|---|---|---|
| Selected transgenic plant | F007A05 | 2 | 0.045 | 0.00114 |
| Selected transgenic plant | F007B03 | 3 | 0.388 | 0.00173 |

*Probability for the occurrence of the line of interest on the hypothesis for non-effectiveness of introduced fragments

TABLE 24

Transgenic plant (maize) specimens selected on the basis of largest ear's weight (generation: T0, number of screened lines: 150, data normalized due to data integration over more than two potting days)

|  | Genomic DNA fragment introduced | No. of individuals investigated | Average of measured values (normalized) | Probability* |
|---|---|---|---|---|
| Selected transgenic plant | F002D10 | 2 | 0.026 | 0.00028 |
| Selected transgenic plant | F004A01 | 2 | 0.059 | 0.00051 |
| Selected transgenic plant | F002B04 | 3 | 0.458 | 0.00060 |
| Selected transgenic plant | F001D09 | 3 | 0.446 | 0.00071 |

*Probability for the occurrence of the line of interest on the hypothesis for non-effectiveness of introduced fragments

TABLE 25

Transgenic plant (maize) specimens selected on the basis of total grain weight in largest ear (generation: T0, number of screened lines: 150, data normalized due to data integration over more than two potting days)

|  | Genomic DNA fragment introduced | No. of individuals investigated | Average of measured values (normalized) | Probability* |
|---|---|---|---|---|
| Selected transgenic plant | F003B03 | 1 | 0.000 | 0.00002 |
| Selected transgenic plant | F004A01 | 2 | 0.062 | 0.00020 |
| Selected transgenic plant | F002D10 | 2 | 0.037 | 0.00071 |

*Probability for the occurrence of the line of interest on the hypothesis for non-effectiveness of introduced fragments

TABLE 26

Transgenic plant (maize) specimens selected on the basis of the number of grains in largest ear (generation: T0, number of screened lines: 150, data normalized due to data integration over more than two potting days)

|  | Genomic DNA fragment introduced | No. of individuals investigated | Average of measured values (normalized) | Probability* |
|---|---|---|---|---|
| Selected transgenic plant | F003B03 | 1 | 0.000 | 0.00003 |
| Selected transgenic plant | F003C02 | 3 | 0.325 | 0.00079 |
| Selected transgenic plant | F005D11 | 3 | 0.334 | 0.00092 |
| Selected transgenic plant | F004A01 | 2 | 0.101 | 0.00123 |

*Probability for the occurrence of the line of interest on the hypothesis for non-effectiveness of introduced fragments

TABLE 27

Transgenic plant (maize) specimens selected on the basis of lamina length (generation: T0, number of screened lines: 150, data normalized due to data integration over more than two potting days)

|  | Genomic DNA fragment introduced | No. of individuals investigated | Average of measured values (normalized) | Probability* |
|---|---|---|---|---|
| Selected transgenic plant | F002A05 | 3 | 0.141 | 0.00269 |
| Selected transgenic plant | F007B08 | 1 | 0.015 | 0.01510 |

*Probability for the occurrence of the line of interest on the hypothesis for non-effectiveness of introduced fragments Example 11

Figure 7:
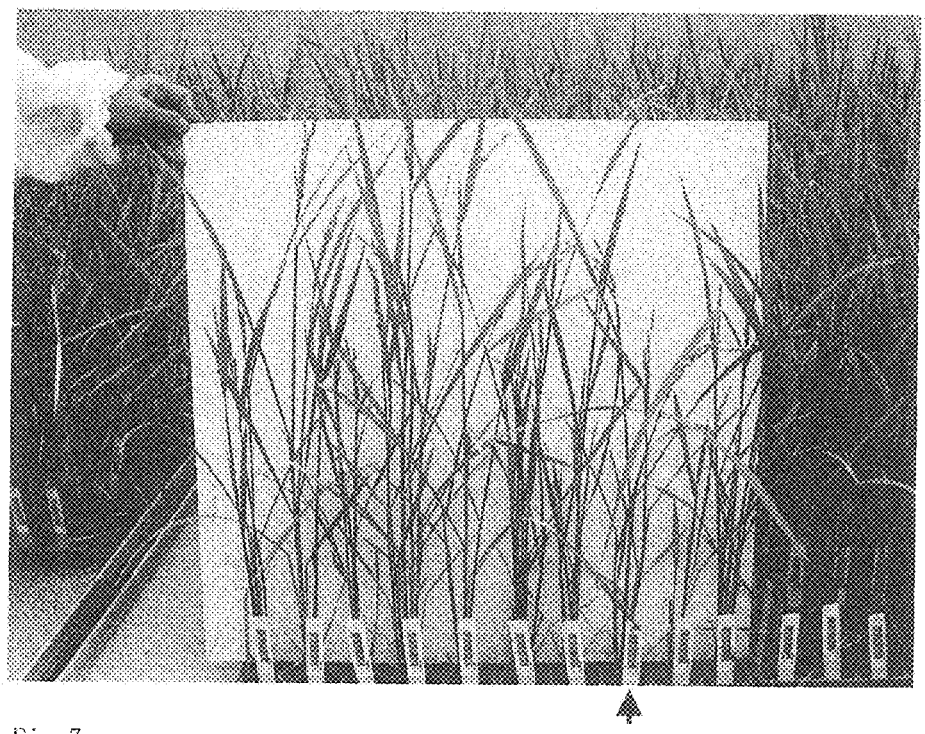
FIG. 7 is a photograph showing transgenic rice specimens selected after introducing genomic DNA fragments of teosinte, as compared with a control plant.

Evaluation of Rice Transformed with the Genomic DNA Fragments Contained in Teosinte Derived Genomic DNA Library and Selection of Plants Having Phenotypic Variation As in the case of *Oryza rufipogon*, genomic DNA was isolated from teosinte (*Zea diploperenis*), a genomic DNA library was constructed, and the genomic clones constituting the library were individually introduced into rice (Yukihikari) by transformation. As a result, transgenic plants were obtained into which a total of 1608 genomic DNA fragments in the genomic DNA library had been introduced individually. The variety of teosinte used in Example 11 is commercially available as teosinte for pasture. The transgenic plants and their progeny were cultivated in a greenhouse as in the case of the *Oryza rufipogon* derived genomic DNA library and the effectiveness of the introduced genomic DNA fragments was assessed by investigating the vigor of the plant taken as a whole, plant length, relative growth rate, number of panicles, shoot weight, panicle weight, panicle length, number of fertile grains, yield, number of leaves, leaf length, leaf width, leaf weight, drought resistance, salt tolerance, and disease resistance. The transgenic plants that were found to have a phenotypic variation in one or more of the traits listed above and their progeny were selected. In addition, the genomic DNA fragments introduced into the selected plants were selected as teosine derived genomic DNA fragments capable of providing crops with a potentially agriculturally advantageous phenotypic variation. The rice variety Yukihikari transformed with GUS gene was used as a control plant. The growth of rice cultivated after treatment with teosinte genomic fragments is shown in FIG. 7.

Example 12

Evaluation of Rice Transformed with the Genomic DNA Fragments Contained in Sudan Grass Derived Genomic DNA Library and Selection of Plants Having Phenotypic Variation As in the case of *Oryza rufipogon*, genomic DNA was isolated from Sudan grass (*Sorghum sudanese*), a genomic DNA library was constructed, and the genomic clones constituting the library were individually introduced into rice (Yukihikari) by transformation. As a result, transgenic plants were obtained into which a total of 2644 genomic DNA fragments in the genomic DNA library had been introduced individually. The variety of Sudan grass used in Example 12 is commercially available for pasture. The transgenic plants and their progeny were cultivated in a greenhouse as in the case of the *Oryza rufipogon* derived genomic DNA library and the effectiveness of the introduced genomic DNA fragments was assessed by investigating the vigor of the plant taken as a whole, plant length, relative growth rate, number of panicles, shoot weight, panicle weight, panicle length, number of fertile grains, yield, number of leaves, leaf length, leaf width, leaf weight, drought resistance, salt tolerance, and disease resistance. The transgenic plants that were found to have a phenotypic variation in one or more of the traits listed above and their progeny were selected. In addition, the genomic DNA fragments introduced into the selected plants were selected as Sudan grass derived genomic DNA fragments capable of providing crops with a potentially agriculturally advantageous phenotypic variation.

In the following case (Table 28), the distribution of measured values for the control plant was fit to a normal distribution. The rice variety Yukihikari transformed with GUS gene was used as a control plant. In accordance with the normal distribution and on the hypothesis that the introduced fragments were not effective, the probability that a line showing the values of measurement for the selected transgenic plant lines would appear was calculated. In each case, the probability of appearance among the screened lines was extremely small and the expected value for the appearance of those selected lines was by far smaller than 1.0. Of the 2644 lines that were investigated for the total panicle weight, 21 lines had expected values smaller than 1.0. Therefore, the hypothesis for the non-effectiveness of the introduced fragments was rejected and it was statistically demonstrated that the selected lines showed a significant phenotypic variation.

TABLE 28

Transgenic plant (rice) specimens selected on the basis of total panicle weight as compared with control plant (generation: T0, number of screened lines: 2644)

|  | Genomic DNA fragment introduced | No. of individuals investigated | Average of measured values | Probability* |
|---|---|---|---|---|
| Selected transgenic plant | J004A03 | 2 | 5.685 | 5.69519E−10 |
| Selected transgenic plant | J022G12 | 1 | 6.850 | 1.08326E−07 |

TABLE 28-continued

Transgenic plant (rice) specimens selected on the basis of total panicle weight as compared with control plant (generation: T0, number of screened lines: 2644)

| | Genomic DNA fragment introduced | No. of individuals investigated | Average of measured values | Probability* |
|---|---|---|---|---|
| Selected transgenic plant | J022B05 | 2 | 4.150 | 9.28268E−06 |
| Selected transgenic plant | J018E04 | 2 | 4.240 | 1.14451E−05 |
| Selected transgenic plant | I022F08 | 2 | 4.210 | 1.99432E−05 |
| Control plant | | 86 | 1.606 | SD: 1.01148 |

*Probability for the occurrence of the line of interest on the hypothesis for non-effectiveness of introduced fragments

Example 13

Evaluation of Rice Transformed with the Genomic DNA Fragments Contained in Millet Derived Genomic DNA Library and Selection of Plants Having Phenotypic Variation As in the case of *Oryza rufipogon*, genomic DNA was isolated from millet (*Seteria italica*), a genomic DNA library was constructed, and the genomic clones constituting the library were individually introduced into rice (Yukihikari) by transformation. As a result, transgenic plants were obtained into which a total of 2952 genomic DNA fragments in the genomic DNA library had been introduced individually. The variety of millet used in Example 13 is extremely early Italian millet R which is commercially available for pasture. The transgenic plants and their progeny were cultivated in a greenhouse as in the case of the *Oryza rufipogon* derived genomic DNA library and the effectiveness of the introduced genomic DNA fragments was assessed by investigating the vigor of the plant taken as a whole, plant length, relative growth rate, number of panicles, shoot weight, panicle weight, panicle length, number of fertile grains, yield, number of leaves, leaf length, leaf width, leaf weight, drought resistance, and disease resistance. The transgenic plants that were found to have a phenotypic variation in one or more of the traits listed above and their progeny were selected. In addition, the genomic DNA fragments introduced into the selected plants were selected as millet derived genomic DNA fragments capable of providing crops with a potentially agriculturally advantageous phenotypic variation.

In the following case (Table 29), the distribution of measured values for the control plant was fit to a normal distribution. The rice variety Yukihikari transformed with GUS gene was used as a control plant. In accordance with the normal distribution and on the hypothesis that the introduced fragments were not effective, the probability that a line showing the values of measurement for the screened transgenic plant lines would appear was calculated. In each case, the probability of appearance of the selected lines was extremely small and the expected value for the appearance of those selected lines was by far smaller than 1.0. Of the 1126 lines that were investigated for the total panicle weight, 15 lines had expected values smaller than 1.0. Therefore, the hypothesis for the non-effectiveness of the introduced fragments was rejected and it was statistically demonstrated that the selected lines showed a significant phenotypic variation.

TABLE 29

Transgenic plant (rice) specimens selected on the basis of total panicle weight as compared with control plant (generation: T0, number of screened lines: 1126)

| | Genomic DNA fragment introduced | No. of individuals investigated | Average of measured values | Probability* |
|---|---|---|---|---|
| Selected transgenic plant | L012C03 | 2 | 5.460 | 1.3433E−06 |
| Selected transgenic plant | L006H01 | 2 | 5.010 | 4.82425E−05 |
| Selected transgenic plant | L004D12 | 2 | 4.855 | 5.00318E−05 |
| Selected transgenic plant | L003H07 | 2 | 4.660 | 0.00016 |
| Selected transgenic plant | L012D02 | 2 | 4.525 | 0.00034 |
| Control plant | | 32 | 1.976 | SD: 1.23387 |

*Probability for the occurrence of the line of interest on the hypothesis for non-effectiveness of introduced fragments

Example 14

Evaluation of Plants Transformed with the Genomic DNA Fragments Contained in Guinea Grass Derived Genomic DNA Library and Selection of Plants Having Phenotypic Variation As in the case of *Oryza rufipogon*, genomic DNA was isolated from Guinea grass (*Panicum maximum*), a genomic DNA library was constructed, and the genomic clones constituting the library were individually introduced into rice, maize and tobacco by transformation. The variety of Guinea grass used in Example 14 is colored Guinea grass commercially available for pasture. The transgenic plants and their progeny were cultivated in a greenhouse as in the case of the

*Oryza rufipogon* derived genomic DNA library and the effectiveness of the introduced genomic DNA fragments was assessed by investigating the vigor of the plant taken as a whole, plant length, relative growth rate, number of panicles, shoot weight, panicle weight, panicle length, number of fertile grains, yield, number of leaves, leaf length, leaf width, leaf weight, drought resistance, salt tolerance, and disease resistance. The transgenic plants that were found to have a phenotypic variation in one or more of the traits listed above and their progeny were selected. In addition, the genomic DNA fragments introduced into the selected plants were selected as Guinea grass derived genomic DNA fragments capable of providing rice, maize or tobacco with a potentially agriculturally advantageous phenotypic variation.

Example 15

Production of Genomic DNA Fragments by PCR Using Selected Genomic DNA Fragments as Templates The selected genomic DNA fragments, AS4(A011D07), AS8(A014E08), AS19(A010B03), AS20(A011C02), AS22 (A014D12), AS27(A012D12), AS28(A015C06) and AS30 (A016D02), were investigated for their terminal nucleotide sequences. Primers were designed for the mapped sequences and vector sequences and, using plasmid DNA isolated from *E. coli* as a template, PCR was conducted to verify the presence of both terminal ends of the T-DNA region (as indicated by PCR1 and in FIG. 8).

The vector region primers used in PCR1 and PCR3 respectively had the following sequences:

```
                                     (SEQ ID NO: 139)
5'-CTGAAGGCGGGAAACGACAATCTG-3';
and (SEQ ID NO: 140)
5'-AACTGCACTTCAAACAAGTGTGAC-3'.
```

The genomic DNA fragment specific primers used in PCR1 had the following sequences:

```
AS4:  5'-GATTCCGACCTCTACACGAACAAC-3'  (SEQ ID NO:
      141)
AS8:  5'-AGAAACCCTAGCCGTCACTTCCCT-3'  (SEQ ID NO:
      142)
AS19: 5'-TCAAGTCATTTCACAAAGTCGGAC-3'  (SEQ ID NO:
      143)
AS20: 5'-GCTTAGAGGTGAAAATGGTAACGG-3'  (SEQ ID NO:
      144)
AS22: 5'-TTCTGTCCTTGTTCGATTTGTCAG-3'  (SEQ ID NO:
      145)
AS27: 5'-CCGGATTCACCGTGGTACGAAAGG-3'  (SEQ ID NO:
      146)
AS28: 5'-TTCCAATTACCAGACACTAAAGCG-3'  (SEQ ID NO:
      147)
AS30: 5'-TGGCACCAGACTTGCCCTCCAATG-3' ( SEQ ID NO:
      148)
```

The genomic DNA fragment specific primers used in PCR3 had the following sequences:

```
AS4:  5'-GTACGGCCTGGGTCACTCACTGTC-3'  (SEQ ID NO:
      149)
AS8:  5'-TCATCATCCTGTTATCTAGACTCC-3'  (SEQ ID NO:
      150)
AS19: 5'-TACTTATTCCGTGAGTCGGAAGCG-3'  (SEQ ID NO:
      151)
AS20: 5'-TCCAGTGTTATGATGTTTGGGCTG-3'  (SEQ ID NO:
      152)
AS22: 5'-AACTCATCTTTAATCCCAGTTTGC-3'  (SEQ ID NO:
      153)
AS27: 5'-TAACGCCATAAACAAGTGTCACTC-3'  (SEQ ID NO:
      154)
AS28: 5'-GAACTGTGAAACTGCGAATGGCTC-3'  (SEQ ID NO:
      155)
AS30: 5'-AAATCCACACGACTCTCGGCAACG-3'  (SEQ ID NO:
      156)
```

The genomic DNA fragments AS4, AS8 and AS22 were also subjected to PCR to verify the presence of central portions of fragment (as indicated by PCR2 in FIG. 8). The primers used in PCR2 had the following sequences:

```
AS4:  5'-TGGGCTCCAGCAGAAACGAACCCT-3'  (SEQ ID NO:
      157)
and
      5'-CTTATATTTAGGAACGGAGTGAGT-3'  (SEQ ID NO:
      158)
AS8:  5'-AAGCGAAGGCACCCCTTCACAT-3' (SEQ ID NO: 159)
and
      5'-ACGAGGAGCCCGACAAGGAGAC-3' (SEQ ID NO: 160)
AS22: 5'-TGAAATACCACTCATGAACTTCCG-3'  (SEQ ID NO:
      161)
and
```

In each case of PCR, Takara ExTaq (TAKARA) or Takara LA Taq (TAKARA) was used and the cycle of thermal denaturation (94° C.×30 sec), annealing (58° C.×30 sec) and extension (72° C.×30 sec) was repeated 30 or 35 times. The PCR products were analyzed by agarose gel electrophoresis.

The results of PCR analysis are shown in FIG. 9. In each of PCR1, PCR2 and PCR3, PCR products of the desired sizes were observed when plasmid DNA for the respective genomic DNA fragments were used as templates. However, no such PCR products were observed when pSB200 was used as a template. These results show that the rufipogon fragments introduced into pSB200 can be produced by PCR (FIG. 9).

Example 16

Use of the Selected Fragments as Markers

The genomic DNA assessed and transferred into rice to cause a phenotypic variation in Example 3 was further transferred into maize for transformation in Example 6. The transgenic maize was cultivated in a greenhouse and pollinated with pollens of the maize variety A188 grown in a separate greenhouse. It is anticipated that the resulting progeny seeds will segregate into two types of individuals, one having *Oryza rufipogon* genomic DNA fragments and the other having not. Hence, using their T-DNA border sequences as a marker, the introduced genomic DNA fragments were amplified by PCR to check for the presence of *Oryza rufipogon* derived genomic DNA fragments. As a result, the plant individuals having the marker were found to be suitable for variety breeding and, hence, applicable in further steps of breeding whereas the plant individuals having no such marker were found to be unsuitable for variety improvement.

Table 30 shows the relation between the presence or absence of introduced genomic DNA fragments and the measured values of traits.

The respective plasmid DNA clones contained the following genomic DNA fragments (A018D06, A047C01, A082B03, A082B06, A083A01, A083A02, A084H04, A084H05, A088A12, A091E11, A049B03, A080C09 and A088C09).

TABLE 30

Relation between the presence or absence of genomic DNA fragments and traits as assessed with reference to the marker created from selected genomic DNA fragments

| Trait | Clone | | | | | | | | | | Average for all individuals | Average for fragment-containing individuals |
|---|---|---|---|---|---|---|---|---|---|---|---|---|
| Plant lengrh at week 4 | A019D09 | Fragment* | − | + | + | + | + | − | | | Average for all individuals | Average for fragment-containing individuals |
| | | (cm) | 63 | 64 | 64 | 67 | 68 | 47 | | | 62.17 | 65.75 |
| Plant lengrh at week 5 | A010A11 | Fragment* | − | − | − | − | + | + | + | − | Average for all individuals | Average for fragment-containing individuals |
| | | (cm) | 89 | 85 | 82 | 97 | 97 | 95 | 94 | 87 | 90.75 | 95.33 |
| Plant lengrh at week 5 | A019D09 | Fragment* | − | + | + | + | + | − | | | Average for all individuals | Average for fragment-containing individuals |
| | | (cm) | 88 | 94 | 95 | 94 | 110 | 76 | | | 92.83 | 98.25 |
| Plant lengrh at week 6 | A019D09 | Fragment* | − | + | + | + | + | − | | | Average for all individuals | Average for fragment-containing individuals |
| | | (cm) | 105 | 118 | 118 | 116 | 132 | 95 | | | 114 | 121 |
| Plant lengrh at weeks 4-5 | A019A06 | Fragment* | + | + | − | − | + | | | | Average for all individuals | Average for fragment-containing individuals |
| | | | 0.06 | 0.08 | 0.05 | 0.05 | 0.08 | | | | 0.066 | 0.074 |
| Plant lengrh at weeks 5-6 | A014A12 | Fragment* | − | − | + | + | − | − | | | Average for all individuals | Average for fragment-containing individuals |
| | | | 0.02 | 0.03 | 0.04 | 0.04 | 0.02 | 0.04 | | | 0.032 | 0.04 |

*Presence or absence of fragment

Example 17

E. coli Based Method of Producing Selected Genomic DNA Fragments

E. coli having a cloning vector (pSB200) containing transformed genomic DNA fragments were individually stored at −80° C. in glycerol stocks. From those stocks, E. coli were picked up and cultured on an LA(Sp50) plate at 28° C. for 3 days until a single colony grew. An LB(Sp50) liquid medium (2 ml) was inoculated with the grown single colony and shaken overnight at 28° C.; thereafter, the liquid culture was transferred into a 1.5-ml microtube and centrifuged at 15000 rpm for 2 minutes to collect cells. The supernatant was discarded and plasmid was isolated from the cell pellet in the usual manner (alkali method); plasmid DNA was dissolved in 40 μl of TE to get the genomic DNA fragments cloned in the cloning vector.

Example 18

Method of Producing DNA Fragments Including the Step of Restrictive Degradation of Prepared Genomic DNA Fragments Using the plasmid DNA prepared in Example 17 (clone designations: AS88, AS90, AS95-AS102, AS104-AS106), reaction solutions were prepared according to the following recipe.

| | |
|---|---|
| Plasmid DNA | 4 μl |
| 10x M buffer (Takara) | 2 μl |
| HindIII | 0.5 μl |
| SacI | 0.5 μl |
| RNaseA | 0.1 μl |
| Sterile water | 12.9 μl |
| Total | 20 μl |

After reaction at 37° C. for 1 hour, the reaction solution was mixed with 4 μl of 6× dye and 6 μl of the mixture was subjected to electrophoresis on 0.7% agarose gel (100 V, 1 hr). After the end of electrophoresis, the gel was stained with Ethidium Bromide to yield restriction enzyme cleaved fragments from the respective genomic clones. An example of this result is shown in FIG. 10.

Example 19

Incorporating E. coli Produced Genomic DNA Fragments into Transformation Vector (pSB200)

Using the plasmid DNA isolated and purified from E. coli (genomic DNA fragment G001A03), BP reaction was performed (25° C. overnight) in accordance with the protocol attached to a GATEWAY Technology (Invitrogen) kit and, after treatment with Proteinase K, ethanol was added to precipitate the plasmid DNA. After centrifugal (15000 rpm)

treatment, the pellet was washed with 70% ethanol and redissolved in 10 μl of TE. A portion (2 μl) of the solution was used to introduce the plasmid into *E. coli* DB3.1 by electroporation and the bacteria was plated on LA (Sp50 Cm30) and cultivated at 28° C. for 3 days. The growing single colony was cultivated on 2 ml of LA(Sp50 Cm30) and the plasmid DNA was isolated in the usual manner (alkali method) and fragment analysis was performed using HindIII and SacI to select the desired plasmid. By BP reaction, the aaB1-HPT-aaB2 fragment is replaced by the aaR1-ccdB-Cm-aaR2 fragment and the vector size changes from 9.8 kb to 10.4 kb; this change was used as a marker for the selection of the recombinant plasmid (G001A03DEST) (lane 2 in FIG. 11).

Using the thus selected plasmid G001A03DEST, LR reaction was performed under the same conditions as the BP reaction and G001A03 bar was selected; G001A03 bar was a clone substituted with a drug selection marker gene. By LR reaction, the aaR1-ccdB-Cm-aaR2 fragment is replaced by the aaB1bar-aaB2 fragment and the vector size changes from 10.4 kb to 9.3 kb; this change was used as a marker for the selection of G001A03 bar (lane 3 in FIG. 11). As a result, the selected fragment of interest could successfully be incorporated into a vector capable of plant transformation.

Example 20

Analysis of the Selected Genomic DNA Clones

The selected genomic DNA fragments were investigated for the nucleotide sequences of 280-500 bases at both terminals. The results are indicated by the sequence numbers associated with the respective genomic DNA fragments shown in Tables 1-9 and in FIG. 3. The sequences of PCR primer pairs that can be used to detect those fragments by PCR are shown in the following Table 31.

TABLE 31

Examples of the selected genomic DNA fragments derived from *Oryza rufipogon's* genome and the PCR primer pairs that can detect them

| Selected genomic DNA fragments | Detecting primer pair 1 | Detecting primer pair 2 |
|---|---|---|
| A029B04 | 5'-TCGAATTTGACCATGAGATACAGA-3' (SEQ ID NO:47) <br> 5'-AAGAAAAAAATGCTTGTGTACTGA-3' (SEQ ID NO:48) | 5'-TCGAGCTAATTAACTAGCCAAGTG-3' (SEQ ID NO:49) <br> 5'-AAGTAACATGAGAAAAAAAACAT-3' (SEQ ID NO:50) |
| A028C04 | 5'-TCGATTAAGACAGCAGGACGGTGG-3' (SEQ ID NO:51) <br> 5'-GCAAGTGCCGTTCACATGGAACCT-3' (SEQ ID NO:52) | 5'-TCGAGGGCGTTGCGCCCCCGATGC-3' (SEQ ID NO:53) <br> 5'-CCGTCTTGAAACACGGACCAAGGA-3' (SEQ ID NO:54) |
| A048F12 | 5'-TCGATGTAGTCCTCCTCGAGGCCG-3' (SEQ ID NO:55) <br> 5'-CAACAACCGAGCAATACAGTTCAA-3' (SEQ ID NO:56) | 5'-TCGAGTGGTCGGCGTCCCCCGGCC-3' (SEQ ID NO:57) <br> 5'-CCGGAGTTCACCATGCCCCGGGGC-3' (SEQ ID NO:58) |
| A049A01 | 5'-TCGAACTAACGCTAACAACGTGCA-3' (SEQ ID NO:59) <br> 5'-ATTTGGCGCATCTGAACACTGAAC-3' (SEQ ID NO:60) | 5'-TCGAGTGCCATCCTCTTCTCAATG-3' (SEQ ID NO:61) <br> 5'-GTTTTTGTTCGTTACAATGAGAAC-3' (SEQ ID NO:62) |
| A046A06 | 5'-TCGAACTACCGAGCTCCCCCTAAT-3' (SEQ ID NO:63) <br> 5'-GTAGCTGAAAGGCGTAACCGTACC-3' (SEQ ID NO:64) | 5'-TCGAACTTGTCTTCCAATTTGCGT-3' (SEQ ID NO:65) <br> 5'-AACCCCGAACTTCAATCAAGTCCC-3' (SEQ ID NO:66) |
| A045B09 | 5'-TCGACGACGACGCGGCGAAGCCGA-3' (SEQ ID NO:67) <br> 5'-CCGCCGCATCCCGCCGTCCCCGCG-3' (SEQ ID NO:68) | 5'-TCGAGGATGCCTGTGGAGTGGTGT-3' (SEQ ID NO:69) <br> 5'-CCGTGGACCGCCGCTTCGTTTCCC-3' (SEQ ID NO:70) |
| A049A07 | 5'-TCGAGCAGTCCGCCGGCAGCCGAC-3' (SEQ ID NO:71) <br> 5'-ATTTCCCGAGCCGGGACGTGGCGG-3' (SEQ ID NO:72) | 5'-TCGAACCATCTAGTAGCTGGTTCC-3' (SEQ ID NO:73) <br> 5'-GCTTCAGCGCCATCCATTTTCGGG-3' (SEQ ID NO:74) |
| A040D06 | 5'-TCGACGGGTTCTGAAACCTGGGAT-3' (SEQ ID NO:75) <br> 5'-GAGCAGCCGCGCCGTCCTACCTAT-3' (SEQ ID NO:76) | 5'-TCGAGCCCCCAACTTTCGTTCTTG-3' (SEQ ID NO:77) <br> 5'-AGCGTATATTTAAGTTGTTGCAGT-3' (SEQ ID NO:78) |
| A036A03 | 5'-TCGAAAATGACCGTCAACAAAACC-3' (SEQ ID NO:79) <br> 5'-ATCAAAAAGGCATCATTTGGTGAG-3' (SEQ ID NO:80) | 5'-TCGATGCATTGAGCAGAAAGGAAT-3' (SEQ ID NO:81) <br> 5'-ATATTCTTCCACCAAAAAGTATCT-3' (SEQ ID NO:82) |
| A051E08 | 5'-TCGATGAAGAACGTAGCGAAATGC-3' (SEQ ID NO:83) <br> 5'-ATATGCTTAAACTCAGCGGGTAGT-3' (SEQ ID NO:84) | 5'-TCGATGCGAGAGCCGAGATATCCG-3' (SEQ ID NO:85) <br> 5'-CCCGTCGCTCCTACCGATTGAATG-3' (SEQ ID NO:86) |

TABLE 31-continued

Examples of the selected genomic DNA fragments derived from *Oryza rufipogon*'s genome and the PCR primer pairs that can detect them

| Selected genomic DNA fragments | Detecting primer pair 1 | Detecting primer pair 2 |
|---|---|---|
| A023D09 | 5'-TCGACGCCATACTGATGAGCAATG-3' (SEQ ID NO:87)<br>5'-GTTGATGCTCTTCTCTGCGTCATC-3' (SEQ ID NO:88) | 5'-TCGAATGCCAGTTAAAGTGATGCC-3' (SEQ ID NO:89)<br>5'-CTACTGCGCCGAGCCCACGCTGAG-3' (SEQ ID NO:90) |
| A030B02 | 5'-TCGAAGCTTCACAGTTGATAACTT-3' (SEQ ID NO:91)<br>5'-GAGGTTTCGAACCCAGGTTGTCTA-3' (SEQ ID NO:92) | 5'-TCGAGGTGAACTATTTTTTTCTT-3' (SEQ ID NO:93)<br>5'-GGCCCTCGGGGCCGAGGCGGGAGT-3' (SEQ ID NO:94) |
| A043F04 | 5'-TCGACCACCTTCTCAGAAGCAAAA-3' (SEQ ID NO:95)<br>5'-AACATCCAACAGATTGAGACACTT-3' (SEQ ID NO:96) | 5'-TCGATAGCACCATTGGGACTATAC-3' (SEQ ID NO:97)<br>5'-TGATTCGAACAAATTTAGGGTATT-3' (SEQ ID NO:98) |
| A049E02 | 5'-TCGATTAAGACAGCAGGACGGTGG-3' (SEQ ID NO:99)<br>5'-CCCGGCTCGGGAAATCTTAACCCG-3' (SEQ ID NO:100) | 5'-TCGACCGAATCGGGTTTTCGGTCG-3' (SEQ ID NO:101)<br>5'-GGATGGCCGGGCTGCCACGCGCAC-3' (SEQ ID NO:102) |
| A010C09 | 5'-TCGACCGAATCGGGTTTTCG-3' (SEQ ID NO:103)<br>5'-ACCGAAAACTGTGTGCGAGC-3' (SEQ ID NO:104) | 5'-TCGATGTCGGCTCTTCCTAT-3' (SEQ ID NO:105)<br>5'-GGGCTGGATCTCAGTGGATC-3' (SEQ ID NO:106) |
| A011C02 | 5'-TCGAGTTAGGGATTTGATTG-3' (SEQ ID NO:107)<br>5'-AATTTGTAATGCTGCGATCT-3' (SEQ ID NO:108) | 5'-TCGAAGGTGGTGTCAAATTA-3' (SEQ ID NO:109)<br>5'-GTTGTCGCTGCCACCTGATC-3' (SEQ ID NO:110) |
| A010B03 | 5'-TCGAACAGCCGACTCAGAAC-3' (SEQ ID NO:111)<br>5'-CCCGGATCGGCCCGAGGGAC-3' (SEQ ID NO:112) | 5'-TCGAAGGATCAAAAAGCAAC-3' (SEQ ID NO:113)<br>5'-GGCTTGGCGAATCAGCGGG-3' (SEQ ID NO:114) |
| A009F06 | 5'-TCGAGTTTGATTCGGATTCG-3' (SEQ ID NO:115)<br>5'-GGCGGCGGCGGCTCGGCGGA-3' (SEQ ID NO:116) | 5'-TCGAATAGCCGTGCCCGCGG-3' (SEQ ID NO:117)<br>5'-TCTAAGCAGCGGAAAATAAA-3' (SEQ ID NO:118) |
| A009E11 | 5'-TCGAGTTGGAGCACGCCTGT-3' (SEQ ID NO:119)<br>5'-GTTGTTACACACTCCTTAGC-3' (SEQ ID NO:120) | 5'-TCGAGGCGGCCGGCCGCGGC-3' (SEQ ID NO:121)<br>5'-CCTATCGATCCTTTAGACCT-3' (SEQ ID NO:122) |
| A008B02 | 5'-TCATATATTAATTCTCTCTCTA-3' (SEQ ID NO:123)<br>5'-TCATGATAGTCAATATGGGCCCTC-3' (SEQ ID NO:124) | 5'-TCGAAGACGCGGAATGGTAGTGAA-3' (SEQ ID NO:125)<br>5'-GGATAGAGATATGGTATAAGAAAT-3' (SEQ ID NO:126) |
| A083G04 | 5'-TCGATGGTAGGATAGGGGCCTACC-3' (SEQ ID NO:127)<br>5'-TTAAGGCCAGGAGCGCATCGCCGG-3' (SEQ ID NO:128) | 5'-TCGAGTTATCATGAATCATCGGAT-3' (SEQ ID NO:129)<br>5'-GACAGCCCGCCCGGCCGCCGCCGT-3' (SEQ ID NO:130) |
| A088E02 | 5'-TCGAGCCTCCACCAGAGTTTCCTC-3' (SEQ ID NO:131)<br>5'-CGGCTGGTCCGCCGATCGGCTCGG-3' (SEQ ID NO:132) | 5'-TCCAGGCGTGGAGCCTGCGGCTTA-3' (SEQ ID NO:133)<br>5'-TGCAATGATCTATCCCCATCACGA-3' (SEQ ID NO:134) |
| A089F12 | 5'-TCGAGCAGTCCGCCGGCAGCCGAC-3' (SEQ ID NO:135)<br>5'-ATTTCCCGAGCCGGGACGTGGCGG-3' (SEQ ID NO:136) | 5'-TCGAACAGCCGACTCAGAACTGGT-3' (SEQ ID NO:137)<br>5'-CTCAAGTCATTTCACAAAGTCGGA-3' (SEQ ID NO:138) |

Example 21

Introducing the Selected Genomic DNA Fragments into Plants

The genomic DNA fragments selected in Examples 3-14 were introduced into rice, maize and tobacco by the method described in Example 2, 6 or 7. The obtained transgenic plants and their progeny were assessed as in Examples 3-14. Further selected were those transgenic plants which got a phenotypic variation in one or more of the traits assessed, and progeny plants thereof. The genomic DNA fragments introduced into the thus selected plants were screened as genomic DNA fragments capable of providing plants with a potentially agriculturally advantageous phenotypic variation.

Selected as the result of secondary screening were the genomic DNA fragments that were verified to be capable of providing the same plants with a potentially agriculturally advantageous phenotypic variation upon retransfer, as well as the genomic DNA fragments that were verified to be capable of providing other plants with an agriculturally advantageous phenotypic variation. This means a successful selection of genomic DNA fragments having higher value than when only primary screening was applied.

Examples of the genomic DNA fragments thus selected are shown in Table 32.

TABLE 32

| Donor plant | Genomic DNA fragment | Plant used in primary screening | Phenotypic variation recognized in primary | Plant used in secondary screening | Phenotypic variation recognized in secondary screening |
| --- | --- | --- | --- | --- | --- |
| Oryza rufipogon | A009E11 (SEQ ID NO: 37 SEQ ID NO: 38) | rice | increased plant length | rice tobacco | Increased plant Increased leaf length |
| Oryza rufipogon | A009F06 (SEQ ID NO: 35 SEQ ID NO: 36) | rice | increased plant length | rice tobacco | Increased plant Increased cullus |
| Oryza rufipogon | A010B03 (SEQ ID NO: 33 SEQ ID NO: 34) | rice | increased plant length | rice maize | Increased plant Increased plant |
| Oryza rufipogon | A010C09 (SEQ ID NO: 29 SEQ ID NO: 30) | rice | increased plant length | rice maize tobacco | Increased plant Increased plant Increased leaf length |
| Oryza rufipogon | A011C02 (SEQ ID NO: 31 SEQ ID NO: 32) | rice | increased plant length | rice maize tobacco | Increased plant Increased plant increased leaf length, increased plant height |

---

The invention claimed is:

1. A method for screening genomic DNA fragments capable of providing plants with an agriculturally advantageous phenotypic variation, comprising the steps of:
   1) preparing genomic DNA from a donor plant that has not been pre-selected for a particular phenotype, which is then cloned into a cloning vector to form a genomic DNA library, with the proviso that the step does not include a preliminary selection step of the genomic DNA fragments;
   2) introducing the genomic fragment from each of the genomic clones constituting the genomic DNA library separately and randomly into a recipient plant that has not been pre-selected for a particular phenotype to produce transgenic plants;
   3) cultivating the transgenic plant or progeny thereof to select a plant exhibiting an agriculturally advantageous phenotypic variation;
   4) selecting the genomic DNA fragment, which was introduced in step (2) into the plant selected in step (3), as a purposed genomic DNA fragment; and
   5) isolating and reintroducing the genomic DNA fragment selected in step (4) or a part thereof into another plant of any species to produce a plant; and
   6) cultivating the plant of step 5) to select a plant exhibiting said agriculturally advantageous phenotypic variation.

2. A method for producing a genomic DNA fragment capable of bringing about an agriculturally advantageous phenotypic variation in plants comprising the steps of:
   culturing E. coli cells containing a cloning vector carrying the purposed genomic DNA fragment selected by the method according to claim 1; and
   amplifying the cloning vector comprising the genomic DNA fragment in the E. coli cells.

3. A method for producing a genomic DNA fragment wherein the purposed genomic DNA fragment selected by the method according to claim 1 is used as a template and the amplification of the fragment is conducted by a biochemical amplification method.

4. A method for producing a DNA fragment wherein the genomic DNA fragment obtained by the method of claim 2 or 3 is digested with restriction enzyme(s).

5. A method for producing a plant having an agriculturally advantageous phenotypic variation comprising the step of introducing a purposed genomic DNA fragment capable of bringing about an agriculturally advantageous phenotypic variation in plants, wherein the genomic DNA fragment is screened by the method according to claim 1; the method further comprising the steps of:
   culturing E. coli cells containing a cloning vector carrying the purposed genomic DNA fragment, and
   amplifying the cloning vector comprising the purposed genomic DNA fragment in the E. coli cells.

6. A method for producing a plant having an agriculturally advantageous phenotypic variation according to claim 5 wherein the step of introducing a purposed genomic DNA fragment capable of bringing about an agriculturally advantageous phenotypic variation in plants comprises the steps of: introducing the genomic fragment into a plant cell or tissue; regenerating a complete plant from the plant cell; and cultivating the regenerated plant.

7. A method for producing a plant according to claim 6 wherein the introduction of the genomic DNA fragment into a plant cell or tissue is conducted by a method selected from the group consisting of biological introduction methods, physical introduction methods and chemical introduction methods.

8. A method for producing a plant according to any one of claims 5 to 7, wherein the genomic DNA fragment capable of bringing about an agriculturally advantageous phenotypic variation is introduced in a plant of the same species as that of the plant from which the genomic DNA fragment was derived.

9. A method for producing a plant according to any one of claims 5 to 7, wherein genomic DNA fragment capable of introducing an agriculturally beneficial phenotypic variation is introduced in a plant of a different species from the plant from which the genomic DNA fragment was derived.

10. A method for analyzing a plant genomic DNA fragment capable of bringing about an agriculturally advantageous phenotypic variation, said method comprising the steps of:
    culturing E. coli cells containing a cloning vector carrying the purposed genomic DNA fragment selected by the method according to claim 1;
    amplifying the cloning vector comprising the purposed genomic DNA fragment in the E. coli cells, and
    reading the nucleotide sequence of the plant genomic DNA fragment in the cloning vector.

11. A method for analyzing a DNA fragment comprising the step of digesting with restriction enzyme(s) the purposed genomic DNA fragment selected by the method according to claim 1.

12. A method for analyzing a DNA fragment wherein the purposed genomic DNA fragment selected by the method according to claim 1 is used as a template and the amplification is conducted by a biochemical amplification method.

13. A method according to claim 11 or 12 wherein the analysis comprises the step of reading the nucleotide sequence of the restriction digest product of the genomic DNA fragment or the biochemically amplified product.

14. The method according to claim 1, wherein the size of the selected genomic DNA fragment is 1 kb or greater provided that the DNA fragment can be introduced into the cloning vector.

15. The method for screening according to claim 1, wherein step (2) comprises the sub-steps of: introducing the genomic fragment into the genome of a cell or tissue of the plant; regenerating a complete plant from the plant cell; and cultivating the regenerated plant.

16. The screening method according to claim 15, wherein the introduction of the genomic DNA fragment into a plant cell or tissue is conducted by a method selected from the group consisting of biological introduction methods, physical introduction methods and chemical introduction methods.

17. The screening method according to claim 1, wherein the agriculturally advantageous phenotypic variation in a plant gives rise to an increase or decrease of the size or the weight of at least a part of the plant or of at least a constituent thereof, an increase of growth rate or an excellent resistance against diseases or pests, under normal cultivation conditions, as compared with a case where the plant does not have the phenotypic variation.

18. The screening method according to claim 1, wherein the agriculturally advantageous phenotypic variation in a plant gives rise to an increase or decrease of the size or the weight of at least a part of the plant or of at least a constituent thereof, an increase of growth rate or an excellent resistance against diseases or pests, under conditions which are more stressful for the plant than normal conditions, as compared with a case where the plant does not have the phenotypic variation.

19. The screening method according to claim 17, wherein the plant transformed in step (2) is of the same species as that of the plant which supplied the genomic DNA in step (1).

20. The screening method according to claim 18, wherein the plant transformed in step (2) is of the same species from that of the plant which supplied the genomic DNA in step (1).

21. The screening method according to claim 17, wherein the plant transformed in step (2) is of a different species from that of the plant which supplied the genomic DNA in step (1).

22. The screening method according to claim 18, wherein the plant transformed in step (2) is of a different species from that of the plant which supplied the genomic DNA in step (1).

23. The screening method according to claim 19, wherein the reintroduction of the genomic DNA fragment in step (5) is made into a plant of the same species as that of the plant which was transformed in step (2).

24. The screening method according to claim 20, wherein the reintroduction of the genomic DNA fragment in step (5) is made into a plant of the same species as that of the plant which was transformed in step (2).

25. The screening method according to claim 21, wherein the reintroduction of the genomic DNA fragment in step (5) is made into a plant of the same species as that of the plant which was transformed in step (2).

26. The screening method according to claim 22, wherein the reintroduction of the genomic DNA fragment in step (5) is made into a plant of the same species as that of the plant which was transformed in step (2).

27. The screening method according to claim 19, wherein the reintroduction of the genomic DNA fragment on step (5) is made into a plant of a different species from that of the plant which was transformed in step (2).

28. The screening method according to claim 20, wherein the reintroduction of the genomic DNA fragment in step (5) is made into a plant of a different species from that of the plant which was transformed in step (2).

29. The screening method according to claim 21, wherein the reintroduction of the genomic DNA fragment in step (5) is made into a plant of a different species from that of the plant which was transformed in step (2).

30. The screening method according to claim 22, wherein the reintroduction of the genomic DNA fragment in step (5) is made into a plant of a different species from that of the plant which was transformed in step (2).

31. A method for screening genomic DNA fragments capable of providing a plant with an agriculturally advantageous phenotypic variation, comprising the steps of:
  1) preparing genomic DNA from a donor plant that has not been pre-selected for a particular phenotype, which is then cloned into a cloning vector to form a genomic DNA library, with the proviso that the step does not include a preliminary selection step of the genomic DNA fragments;
  2) introducing the genomic fragment from each of the genomic clones constituting the genomic DNA library separately and randomly into a recipient plant that has not been pre-selected for a particular phenotype, which is the same species as the donor plant, to produce a transgenic plant;
  3) cultivating the transgenic plants or progeny thereof to select a plant exhibiting an agriculturally advantageous phenotypic variation;
  4) selecting the genomic DNA fragment, which was introduced in step (2) into the plant selected in step (3), as a purposed genomic DNA fragment; and
  5) optionally introducing the genomic DNA fragment selected in step (4), or a part thereof, into another plant to repeat steps (3) and (4), and selecting a genomic DNA fragment which produces a plant exhibiting an agriculturally advantageous phenotypic variation as a purposed genomic DNA fragment in each repetition.

* * * * *

SEQUENCE LISTING

```
<160> NUMBER OF SEQ ID NOS: 162

<210> SEQ ID NO 1
<211> LENGTH: 400
<212> TYPE: DNA
<213> ORGANISM: Oryza rufipogon
<220> FEATURE:
<223> OTHER INFORMATION: A029B04 F: one terminus of DNA fragment
      A029B04.

<400> SEQUENCE: 1
tcgaatttga ccatgagata cagatatgaa tcggtagaat cattataagc atgattactg      60
attcttaaaa agatgttgac aaatccagat tcccaattcc tcgcaggcct aatttaattt    120
tcccccatgg cacagggcca gcgaggtcga tcaatcacta tgggagccat actattgtag    180
aagttctcaa tgagatattt gcaagcaatg tggcagaact ctctgtgcag atagtgaagg    240
tagctctgcc atgtacacag gagtgaggtg atgaaccagc accctgtgtt tttaacaact    300
agataaggtg tttggcttct attgtagagc tgcatggcat atatatattt agtagaagta    360
aacatgcagt acattttcag tacacaagca ttttttttctt                        400

<210> SEQ ID NO 2
<211> LENGTH: 400
<212> TYPE: DNA
<213> ORGANISM: Oryza rufipogon
<220> FEATURE:
<223> OTHER INFORMATION: A029B04 R: the other terminus of DNA fragment
```

-continued

A029B04 to A029B04 F.

<400> SEQUENCE: 2
tcgagctaat taactagcca agtgtagggt tgggagacat ctggatatca cttctgacgt    60
tttcctatgt gtaaactact gagatttggt atggcagttt ctgtggcact tgcacaagga   120
ccagttttat tcctccttga actgtaatta accaccttt tcaccgacct tcctttcgag   180
tagctagaga catttctaca tgctcgaatt aattagttaa tgctaggaac tggatccta   240 tttttgagtt acagaagttg ctagctactc tgttcttagt ttctcacgga gtgcagctag   300
ctagcttcga taaacagctc aaaaaacaga aatttagtcc tggcaaatgt atgtgccaaa   360
cttaatgcat gagaatatgt tttttttct catgttactt                          400

<210> SEQ ID NO 3
<211> LENGTH: 300
<212> TYPE: DNA
<213> ORGANISM: Oryza rufipogon
<220> FEATURE:
<223> OTHER INFORMATION: A028C04 F: one terminus of DNA fragment
      A028C04.

<400> SEQUENCE: 3
tcgattaaga cagcaggacg gtggtcatgg aagtcgaaat ccgctaagga gtgtgtaaca    60
actcacctgc cgaatcaact agccccgaaa atggatggcg ctgaagcgcg cgacccacac   120
caggccatct gggcgagcgc catgccccga tgagtaggag ggcgcggcgg ccgccgcaaa   180
acccggggcg cgagcccggg cggagcggcc gtcggtgcag atcttggtgg tagtagcaaa   240
tattcaaaat agaactttga aggccgaaga ggagaaaggt tccatgtgaa cggcacttgc   300

<210> SEQ ID NO 4
<211> LENGTH: 400
<212> TYPE: DNA
<213> ORGANISM: Oryza rufipogon
<220> FEATURE:
<223> OTHER INFORMATION: A028C04 R: the other terminus of DNA fragment
      A028C04 to A028C04 F.

<400> SEQUENCE: 4
tcgagggcgt tgcgccccg atgcctctaa tcattggctt tacccgatag aactcgtaat    60
gggctccagc tatcctgagg gaaacttcgg agggaaccag ctactagatg gttcgattag   120
tctttcgccc ctatacccaa gtcagacgaa cgatttgcac gtcagtatcg cttcgagcct   180
ccaccagagt ttcctctggc ttcgccccgc tcaggcatag ttcaccatct ttcgggtccc   240
gacaggcgtg ctccaactcg aacccttcac agaagatcag ggtcggccag cggtgcggcc   300
cgtgagggcc tcccgctcgt cagcttcctt gcgcatccca ggtttcagaa cccgtcgact   360
cgcacgcatg tcagactcct tggtccgtgt ttcaagacgg                         400

<210> SEQ ID NO 5
<211> LENGTH: 400
<212> TYPE: DNA
<213> ORGANISM: Oryza rufipogon
<220> FEATURE:
<223> OTHER INFORMATION: A048F12 F: one terminus of DNA fragment
      A048F12.

<400> SEQUENCE: 5
tcgatgtagt cctcctcgag gccgaggctg acagagatgg cgccgagaag ccggagcccc    60
agttgccgga cttctcggca gtacgtgctc ataatctctc tgcatgccag gaaaagtgc   120 aacggaaaat taagcgtcca cgccttaatt ttggcgtttt actgaaacta gttgctgtcc   180

```
tggacttcag ctagcttgat tttactccag cacattggat tttggaatta acagacgaag    240
taggagaccg atgaagaatc ggtccccttc tttttgcgag gtcaagggtg cggtttacct    300
tttccacgat ttgtctcgag taaaaatctc gcaagttcat gcatgtctct ggtagggtga    360
ttagtcttct acgtgattga actgtattgc tcggttgttg                          400

<210> SEQ ID NO 6
<211> LENGTH: 400
<212> TYPE: DNA
<213> ORGANISM: Oryza rufipogon
<220> FEATURE:
<223> OTHER INFORMATION: A048F12 R: the other terminus of DNA fragment
      A048F12 to A048F12 F.

<400> SEQUENCE: 6
tcgagtggtc ggcgtccccc ggccgggctc catacggctg ccacgggcg acggcactga     60 gctgcctaac ccgtggaaca tcgaacacct tcgtcgcttc taccctgag ggggggtcg     120 ggtgtcaggt ttcgggctcg ggccaacccc gcacccctc gggcgtgcag ggttggccgg    180
gggctgccac acatgcacat tcttatttct cttatttcag tatttcaata aaagcagttt    240
caatttccta aaggctgtat ctgtgctgtt gtttcttttg aagaatcttg acttgaaata    300
ggtcactcgt gctcaatcct gccctcgggg gctcgggtcg gctaaaatcg ccaaacgggg    360
cccagaaccg agccgtgccc cggggcatgg tgaactccgg                          400

<210> SEQ ID NO 7
<211> LENGTH: 400
<212> TYPE: DNA
<213> ORGANISM: Oryza rufipogon
<220> FEATURE:
<223> OTHER INFORMATION: A049A01 F: one terminus of DNA fragment
      A049A01.

<400> SEQUENCE: 7
tcgaactaac gctaacaacg tgcagaaaat ctccctgcat ctcgtgatgg ttcattggat     60
cgtagtgggc tccaataagt ggggcttcca ggcccatctt gctggggccc aatagtaccg    120
aaaacgaaag tagcaccaag cttccatgca cgacgacaga aacgagcgat gacattgttg    180
tttctttggg aagaaggaca acacaaccga tccgttagct tgtccatttc gaccctaagt    240
ggtgcaaaat gattggagaa ttagtcacca aaataaataa ttgtactagt tctaagttct    300
gataacacaa ctagtgacca accatgacta gttctttaga gatgggtttc agattttcag    360
tacagagccg acgcaagttc agtgttcaga tgcgccaaat                          400

<210> SEQ ID NO 8
<211> LENGTH: 400
<212> TYPE: DNA
<213> ORGANISM: Oryza rufipogon
<220> FEATURE:
<223> OTHER INFORMATION: A049A01 R: the other terminus of DNA fragment
      A049A01 to A049A01 F.

<400> SEQUENCE: 8
tcgagtgcca tcctcttctc aatgagagta accattgaaa ttctaacatc tattccatca     60
taaattcttg tttggagcag ctgttttggt cttgacaatt aaaacgcgtg ttaagaaaaa    120
caccgctctt tctattacaa tatttgctg tgggatttcc ctgattaata ccatatgaac    180
ttttatctta catattgcat tgtcttcatc gccaaaagtg agtgactttc agttttcttt    240
ttctatatat gcagcacaga tgattttgtt ttagaacgat atgatacaga gataacaacc    300
```

| | |
|---|---|
| gaatcaaccc catttgctat tgcacttgca aaacatttgc actctgttgg cgctaagatg | 360 |
| tatggagcat tctggtgttc tcattgtaac gaacaaaaac | 400 |

```
<210> SEQ ID NO 9
<211> LENGTH: 400
<212> TYPE: DNA
<213> ORGANISM: Oryza rufipogon
<220> FEATURE:
<223> OTHER INFORMATION: A046A06 F: one terminus of DNA fragment
      A046A06.

<400> SEQUENCE: 9
```

| | |
|---|---|
| tcgaactacc gagctccccc taatcatttc gtcttccaag aagacgacgt gtctcgtttc | 60 |
| tacaaactt gtataattgt ttggataata gaaacgataa ccttttgatc tttcaggata | 120 |
| gcgaataaaa tggcagctga ctattttggg atccaatttc caaggtttgg gttaaatatt | 180 |
| ttagcctcta caggactccc ccacacatgg aggtgagcta gcgagggtac tcttcccgtc | 240 |
| catagctcat acagtgtttg ggcaccgatt tgcttggaac tctgttgagg atatgaatgg | 300 |
| cggttttaa tgtctctatc cataaaccca atggtagagt ggagtagctc atcatgctgc | 360 |
| gcaccatatc cataagggta cggttacgcc tttcagctac | 400 |

```
<210> SEQ ID NO 10
<211> LENGTH: 400
<212> TYPE: DNA
<213> ORGANISM: Oryza rufipogon
<220> FEATURE:
<223> OTHER INFORMATION: A046A06 R: the other terminus of DNA fragment
      A046A06 to A046A06 F.

<400> SEQUENCE: 10
```

| | |
|---|---|
| tcgaacttgt cttccaattt gcgtacctct tgtcgatatg ccatcatgtt gtcgtcaagg | 60 |
| caggaccact ctttcataac ttggttgaca actagctgtg aatcgcctcg aactattaga | 120 |
| cgctttatcc ctagagaaat tgcgatccgc agtccatgga ggagcgcctc gtactcggcg | 180 |
| acgttgtgag acgccgaaaa atgtatccaa agcacatagc ttaatctttc tccagtcggg | 240 |
| gaaattaaaa ccactcctgc tccagtgccc gaaagtcgct tcgacccgtc gaaatgcata | 300 |
| gtccagtgct caatcttctc cgcggggta tcctcctggc actcggtcca ttcggcgaca | 360 |
| aaatcagcta acgcttggga cttgattgaa gttcggggtt | 400 |

```
<210> SEQ ID NO 11
<211> LENGTH: 400
<212> TYPE: DNA
<213> ORGANISM: Oryza rufipogon
<220> FEATURE:
<223> OTHER INFORMATION: A045B09 F: one terminus of DNA fragment
      A045B09.

<400> SEQUENCE: 11
```

| | |
|---|---|
| tcgacgacga cgcggcgaag ccgaaggagg cggcaccgag aggggaggaa gtccggagcg | 60 |
| acggcggcgg cgaaccggag ctcgtcggcg acgcggaga gagaggaaga cgacgcgagc | 120 |
| gcgattccga cggtgagagc gagcggcgaa cggcggaaac ggaggagaga ggcgcgaggg | 180 |
| acgcttaaat agcgacggga gggggagaga gcggccggag agggagaaat cggccgcgga | 240 |
| aatctcggcc gccattgatt gcgccggcga ggaatgcggg agagaatccg gacgcatccg | 300 |
| agggagagag agaggggga aagcggggga aacgggagag ggaatcgcgg ggaatgattc | 360 |
| cccccttcatt atggcgcgcg gggacggcgg gatgcggcgg | 400 |

```
<210> SEQ ID NO 12
<211> LENGTH: 400
<212> TYPE: DNA
<213> ORGANISM: Oryza rufipogon
<220> FEATURE:
<223> OTHER INFORMATION: A045B09 R: the other terminus of DNA fragment
      A045B09 to A045B09 F.

<400> SEQUENCE: 12
tcgaggatgc ctgtggagtg gtgttcccgc tgcagttcaa gtcaaggctt agctccagtt      60
ttcttttgtt ttccgctgca tttctgtaag acttttatga tgtttgtaag acgtggatct    120
gaatgtcaac atagtcgttt gtgtaccccg gccggtcctg acggggggtt ttaatgcaca    180
ttctgcttgg aatcctattc gggaatttct gggcgtgaca gcggctgaca gccgggcccc    240
acgcggcagc cgctcggtgc gcccgaaggc ggccacggcg gcgcggccgg cgggaggcgg    300
ctcgcccgcg cccctatggt cgccggcggc ggccataggc acgtcggagc agcgcccgag    360
agaggggagg gaaaggggga aacgaagcgg cggtccacgg                          400

<210> SEQ ID NO 13
<211> LENGTH: 400
<212> TYPE: DNA
<213> ORGANISM: Oryza rufipogon
<220> FEATURE:
<223> OTHER INFORMATION: A049A07 F: one terminus of DNA fragment
      A049A07.

<400> SEQUENCE: 13
tcgagcagtc cgccggcagc cgacgggttc ggggccggga ccccgagcc cagccctcag       60 agccaatcct ttcccgaag ttacggatcc gttttgccga cttcccttgc ctacattgtt    120
ccattggcca gaggctgttc accttggaga cctgatgcgg ttatgagtac gaccgggcgt    180
ggacggtact cggtcctccg gattttcaag ggccgccggg ggcgcaccgg acaccgcgcg    240
acgtgcggtg ctcttccggc cgctggaccc tacctccggc tgaaccgttt ccagggttgg    300
cgggccgtta agcagaaaag ataactcttc ccgaggcccc cgccggcgtc tccggacttc    360
ctaacgtcgc cgtcaaccgc cacgtcccgg ctcgggaaat                          400

<210> SEQ ID NO 14
<211> LENGTH: 400
<212> TYPE: DNA
<213> ORGANISM: Oryza rufipogon
<220> FEATURE:
<223> OTHER INFORMATION: A049A07 R: the other terminus of DNA fragment
      A049A07 to A049A07 F.

<400> SEQUENCE: 14
tcgaaccatc tagtagctgg ttccctccga agtttccctc aggatagctg gagcccatta     60
cgagttctat cgggtaaagc caatgattag aggcatcggg ggcgcaacgc cctcgaccta    120
ttctcaaact ttaaataggt aggacggcgc ggctgctccg gtgagccgcg ccacggaatc    180
gggagctcca agtgggccat ttttggtaag cagaactggc gatgcgggat gaaccggaag    240
cctggttacg gtgccgaact gcgcgctaac ctagaaccca caaagggtgt tggtcgatta    300
agacagcagg acgtggtca tggaagtcga atccgctaa ggagtgtgta acaactcacc    360
tgccgaatca actagccccg aaaatggatg gcgctgaagc                          400

<210> SEQ ID NO 15
<211> LENGTH: 400
<212> TYPE: DNA
<213> ORGANISM: Oryza rufipogon
<220> FEATURE:
```

-continued

<223> OTHER INFORMATION: A040D06 F: one terminus of DNA fragment
     A040D06.

<400> SEQUENCE: 15

```
tcgacgggtt ctgaaacctg ggatgcgcaa ggaagctgac gagcgggagg ccctcacggg      60
ccgcaccgct ggccgaccct gatcttctgt gaagggttcg agttggagca cgcctgtcgg     120
gacccgaaag atggtgaact atgcctgagc ggggcgaagc cagaggaaac tctggtggag     180
gctcgaagcg atactgacgt gcaaatcgtt cgtctgactt gggtataggg gcgaaagact     240
aatcgaacca tctagtagct ggttccctcc gaagtttccc tcaggatagc tggagcccat     300
tacgagttct atcgggtaaa gccaatgatt agaggcatcg ggggcgcaac gccctcgacc     360
tattctcaaa ctttaaatag gtaggacggc gcggctgctc                           400
```

<210> SEQ ID NO 16
<211> LENGTH: 400
<212> TYPE: DNA
<213> ORGANISM: Oryza rufipogon
<220> FEATURE:
<223> OTHER INFORMATION: A040D06 R: the other terminus of DNA fragment
     A040D06 to A040D06 F.

<400> SEQUENCE: 16

```
tcgagccccc aactttcgtt cttgattaat gaaaacatcc ttggcaaatg ctttcgcagt      60
tgttcgtctt tcataaatcc aagaatttca cctctgacta tgaaatacga atgccccga     120
ctgtccctat taatcattac tccgatcccg aaggccaaca caataggacc ggaatcctat     180
gatgttatcc catgctaatg tatccagagc gatggcttgc tttgagcact ctaatttctt     240
caaagtaacg gcgccggagg cacgacccgg ccagttaagg ccaggagcgc atcgccggca     300
gaagggtcga gcaggtcggt gctcgccgtg aggcggaccg gccggcccgg cccaaggtcc     360
aactacgagc ttttaactg caacaactta aatatacgct                            400
```

<210> SEQ ID NO 17
<211> LENGTH: 400
<212> TYPE: DNA
<213> ORGANISM: Oryza rufipogon
<220> FEATURE:
<223> OTHER INFORMATION: A036A03 F: one terminus of DNA fragment
     A036A03.

<400> SEQUENCE: 17

```
tcgaaaatga ccgtcaacaa aaccccccaa gcttgaacct ttgctcatcc cgagtgaagg      60
acgaaaggaa acaaagactt ggatgttgat cagaagttgc tactatgctg catatctcaa     120
agatacaggt gcaaggcata tgtactctct cttagattaa ataatctttg gcatggtggc     180
ttatccttac ccctgattct catgagacac tacttctcct tgccttgggc ggttgaaaga     240
cagaacaaca attagagcac caatcacccg atctttattc aattcttatt ctggaagttt     300
ttcaaatgat tttgcaaaga aaaccaagtt cctcaaatga ttcactcagt ctctctaagt     360
gtatcatttc gaattcctca ccaaatgatg ccttttgat                            400
```

<210> SEQ ID NO 18
<211> LENGTH: 400
<212> TYPE: DNA
<213> ORGANISM: Oryza rufipogon
<220> FEATURE:
<223> OTHER INFORMATION: A036A03 R: the other terminus of DNA fragment
     A036A03 to A036A03 F.

<400> SEQUENCE: 18

```
tcgatgcatt gagcagaaag gaatattgta atcaagcaat tatccaagga tgcccacatg    60
aactgcaaaa ggaaatacaa caattaagat tggagtttac agaacccgga cttttggcaa   120
ctctagaggt aaaaccaaca cttctagatc aagtctgtga tgctcagaag gaagatgaag   180
aattagaaga aatttgacac ggagttcaaa aagaattgaa atggattttt acggaaaaca   240
atgatggagc tcttagattt aaaggacgtc tttgcatccc agacaggaaa gaaatcaagg   300
atttaatttt gcaagaagcc catcgctcac tcttttctat ccatcctgga agcaccaaga   360
tgtatcatga cctaaaagat acttttggt ggaagaatat                          400
```

```
<210> SEQ ID NO 19
<211> LENGTH: 400
<212> TYPE: DNA
<213> ORGANISM: Oryza rufipogon
<220> FEATURE:
<223> OTHER INFORMATION: A051E08 F: one terminus of DNA fragment
      A051E08.

<400> SEQUENCE: 19
```

```
tcgatgaaga acgtagcgaa atgcgatacc tggtgtgaat tgcagaatcc cgtgaaccat    60
cgagtctttg aacgcaagtt gcgcccgagg ccatccggcc gagggcacgc ctgcctgggc   120
gtcacgccaa aagacgctcc acgcgccccc cctatccggg agggcgcggg gacgcggtgt   180
ctggcccccc gcgcctcgcg gcgcggtggg ccgaagctcg gctgccggc gaagcgtgcc    240 gggcacagcg catggtggac agctcacgct ggctctaggc cgcagtgcac cccggcgcgc   300
ggccggcgcg atggcccctc aggacccaaa cgcaccgaga gcgaacgcct cggaccgcga   360
ccccaggtca ggcgggacta cccgctgagt ttaagcatat                         400
```

```
<210> SEQ ID NO 20
<211> LENGTH: 400
<212> TYPE: DNA
<213> ORGANISM: Oryza rufipogon
<220> FEATURE:
<223> OTHER INFORMATION: A051E08 R: the other terminus of DNA fragment
      A051E08 to A051E08 F.

<400> SEQUENCE: 20
```

```
tcgatgcgag agccgagata tccgttgccg agagtcgtgt ggatttagct cgtggtatcg    60
cgccgcgccg ccggacggcc agggccgacc gggccggcgc ggggcgtatc gctgtgttcc   120
ttgacgccgt cggcgccgtg ggttctgttg cggcccgggg gcctcggttg cctcgcgcgc   180
gagcgctcgg cgggcagggg tgacgcgttc gcggtctgtt ttggtcaggg tcacgacaat   240
gatccttccg caggttcacc tacggaaacc ttgttacgac ttctccttcc tctaaatgat   300
aaggttcaat ggacttctcg cgacgtcggg ggcggcgaac cgccccgtc gccgcgatcc     360 gaacacttca ccggaccatt caatcggtag gagcgacggg                         400
```

```
<210> SEQ ID NO 21
<211> LENGTH: 300
<212> TYPE: DNA
<213> ORGANISM: Oryza rufipogon
<220> FEATURE:
<223> OTHER INFORMATION: A023D09 F: one terminus of DNA fragment
      A023D09.

<400> SEQUENCE: 21
```

```
tcgacgccat actgatgagc aatgattcgt aatactacta attaatctag cagcatgata    60
cggagcatca acgttaagta agatgagcag catccatcaa gaagaaggaa gcgtctcctc   120
cactgccgag tgacaccacg ctcttgtcct gtaccactat cgctacttaa tgcctaatcc   180
```

```
tcctcctgtc gtacaagtac cacgaaacag aatataaaca ataaagacaa gtttttttaa    240
aaaaaaattg tctgaagatt aattaagagt tagtgagatg acgcagagaa gagcatcaac    300
```

<210> SEQ ID NO 22
<211> LENGTH: 360
<212> TYPE: DNA
<213> ORGANISM: Oryza rufipogon
<220> FEATURE:
<223> OTHER INFORMATION: A023D09 R: the other terminus of DNA fragment
      A023D09 to A023D09 F.

<400> SEQUENCE: 22

```
tcgaatgcca gttaaagtga tgccattcca gcgaatcaac tcttgcgatg gtagatgtgc    60
aattttctca ccagatttgg ctgatagcca ttagtctgct gtactattaa acctgctctg    120
atctagggtt ccagcccccc accacggccg cacagccatg gatgagcatc aagcagcca    180 cgcgcgagcg tgtgtggagg cggcccagac tgaagcaaat cagaaatctg gtgatggtaa    240
tggtgaaggc gagcacacca aaccaaaaac caaatcaaaa gctcaactga acaaacgta    300 cgaatcatcc atccatcgcg cggtggtggc tcagatctca gcgtgggctc ggcgcagtag    360
```

<210> SEQ ID NO 23
<211> LENGTH: 300
<212> TYPE: DNA
<213> ORGANISM: Oryza rufipogon
<220> FEATURE:
<223> OTHER INFORMATION: A030B02 F: one terminus of DNA fragment
      A030B02.

<400> SEQUENCE: 23

```
tcgaagcttc acagttgata acttgacatg gtcatcagca ctatacatgt catgttggga    60
gttagcagcc ttcaactagt accttattag gtgcctgaat aatcgaggtg gtataattca    120
ttcagacatg tgcccgttaa aacttctagg gaaacttaaa ttatggcctt tacattaaaa    180
aaactaaaat tattttctta aaaaaactta aattatggtt cagactctac aagaaacgcc    240
cataagtctt tcgactagct tcacaaggtg gtgggctaga caacctgggt tcgaacctc    300
```

<210> SEQ ID NO 24
<211> LENGTH: 280
<212> TYPE: DNA
<213> ORGANISM: Oryza rufipogon
<220> FEATURE:
<223> OTHER INFORMATION: A030B02 R: the other terminus of DNA fragment
      A030B02 to A030B02 F.

<400> SEQUENCE: 24

```
tcgaggtgaa ctatttttt tctttttta agttcgttat tcttttcttt actacggtaa    60
atttcagtaa atacaaggag tacatcaatt tttccgaaaa tttctatccc aattgtcggt    120
gacatgggac cggagtatc atgactagag gcttgaggca gacacaatcg cccacgtggc    180
ctggcaccct cggggacgt cgggcccgag ggtgatgtgt tcgccctcct cttagtctcc    240 ccgaggggt cggaccactc ccgcctcggc cccgagggcc                           280
```

<210> SEQ ID NO 25
<211> LENGTH: 400
<212> TYPE: DNA
<213> ORGANISM: Oryza rufipogon
<220> FEATURE:
<223> OTHER INFORMATION: A043F04 F: one terminus of DNA fragment
      A043F04.

<400> SEQUENCE: 25

```
tcgaccacct tctcagaagc aaaatgtaca aacagagggt gctgaagaag attcgagttt    60
ccattggcac aattcagatg gcagtccaca tgctgagctt aagatagac atggatacag    120 acacaagagg gcatgctgca cgcgtattgc tggagctcgc gcctgacctc caggtggaga    180
gctttcctgg tatcctgcct gcaatctcct cactgctcag cacaaacaag ggggccacaa    240
acagtgaaag ctccagcaac ccaatcactg cagtggcgga cgcaactta aaatatagat    300 gggacggaga acggagatgt tcactcgata agagcaatcg aacacaacac atatcgtatt    360
aatagtttat tcgtataagt gtctcaatct gttggatgtt                          400
```

<210> SEQ ID NO 26
<211> LENGTH: 400
<212> TYPE: DNA
<213> ORGANISM: Oryza rufipogon
<220> FEATURE:
<223> OTHER INFORMATION: A043F04 R: the other terminus of DNA fragment
      A043F04 to A043F04 F.

<400> SEQUENCE: 26

```
tcgatagcac cattgggact atactggaca taccaactaa gaccaaggat aggctgaaat    60
cacgtaagga cctcgtggat atgcaaataa ggaaagagta ccttccgcct gcttgctaca    120
ccttgacaag agaggacaaa attgcattgt gcaaatccct acatggggtg agagtgccta    180
ctgccttctc ctcaaacatt aagcgactag tgtcgatgaa ggatctgtcg ctttcaggct    240
acaattctca taactgtcat gtaatgctca cagtattcct tgccattgca actagagcag    300
tcgaacccac gtctgcagaa attagcacca tatacaatcc ttacattat tcgaaatgca    360 gaataacata acatacaata ccctaaattt gttcgaatca                          400
```

<210> SEQ ID NO 27
<211> LENGTH: 400
<212> TYPE: DNA
<213> ORGANISM: Oryza rufipogon
<220> FEATURE:
<223> OTHER INFORMATION: A049E02 F: one terminus of DNA fragment
      A049E02.

<400> SEQUENCE: 27

```
tcgattaaga cagcaggacg gtggtcatgg aagtcgaaat ccgctaagga gtgtgtaaca    60
actcacctgc cgaatcaact agccccgaaa atggatggcg ctgaagcgcg cgacccacac    120
caggccatct gggcgagcgc catgcccga tgagtaggag ggcgcggcgg ccgccgcaaa    180
acccggggcg cgagcccggg cggagcggcc gtcggtgcag atcttggtgg tagtagcaaa    240
tattcaaatg agaactttga aggccgaaga ggagaaaggt tccatgtgaa cggcacttgc    300
acatgggtaa gccgatccta agggacgggg taaccccggc agagagcgcg accacgcgcg    360
tgccccgaaa gggaatcggg ttaagatttc ccgagccggg                          400
```

<210> SEQ ID NO 28
<211> LENGTH: 400
<212> TYPE: DNA
<213> ORGANISM: Oryza rufipogon
<220> FEATURE:
<223> OTHER INFORMATION: A049E02 R: the other terminus of DNA fragment
      A049E02 to A049E02 F.

<400> SEQUENCE: 28

```
tcgaccgaat cgggttttcg gtcggtcggc cggtgggtgg ctgcacgagc cagcccttcc    60
caactcgcgc acggttgccg gtcggtcggc ccggcgcccg aacgtggacc gaaccgggtg    120
```

```
ccgtgcgcgt ggcagcccgg ccatcccttc cccctacta tagtcgtggg ccatagccag     180
ccccacgcac ccctagcgtc cagcccttca cagctcgcac acagttttcg gccggtcgcc     240
cggcggaccg aacgtcgacc gaatcgggtt tcggtcggt cggccggtgg gtggctgcac      300
gagccagccc ttcccaactc gcgcacggtt gccggtcggt cggcccggcg cccgaacgtg     360
gaccgaaccg ggtgccgtgc gcgtggcagc ccggccatcc                           400
```

<210> SEQ ID NO 29
<211> LENGTH: 500
<212> TYPE: DNA
<213> ORGANISM: Oryza rufipogon
<220> FEATURE:
<223> OTHER INFORMATION: A010C09 F: one terminus of DNA fragment
    A010C09.
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (484)..(484)
<223> OTHER INFORMATION: n is a, c, g, or t
<220> FEATURE:
<221> NAME/KEY: misc_feature
<222> LOCATION: (488)..(488)
<223> OTHER INFORMATION: n is a, c, g, or t

<400> SEQUENCE: 29

```
tcgaccgaat cgggttttcg gtcggtcggc caggngggtg gctgcacgag ccagcccttc     60
ccaactcgcg cacggttgcc ggtcggtcgg cccggcgccc gaacgtggac cgaaccgggt    120
gccgtgcgcg tggcagcccg ccatcccttt cccccctact atagtctggg ccatagcca    180 gcccaacgca ccctagcgt ccagcccttc acagctcgca cacagtttc ggccggtcgt     240 ccggcggacc gaacgtcgac cgaatcgggt tttcggccgg tcggtggctg cacgagccag    300 ccccttcccaa ctcgcgcacg gttgccgtc ggtcggcccg cgaccgaac gtggaccgaa    360 ccgggtgccg tgcgcgtggc agcccggcca tcccttcccc cctactatag tcgtggggcc    420
atagccagcc caacgcaccc ctagcgtgca gcccttcaca gctcgcacac agttttcggt    480
cggncgancg gcggaccgaa                                                500
```

<210> SEQ ID NO 30
<211> LENGTH: 500
<212> TYPE: DNA
<213> ORGANISM: Oryza rufipogon
<220> FEATURE:
<223> OTHER INFORMATION: A010C09 R: the other terminus of DNA fragment
    A010C09 to A010C09 F.

<400> SEQUENCE: 30

```
tcgatgtcgg ctcttcctat cattgtgaag cagaattcac caagtgttgg attgttcacc     60
caccaatagg gaacgtgagc tgggtttaga ccgtcgtgag acaggttagt tttaccctac    120
tgatgaccgt gccgcgatag taattcaacc tagtacgaga ggaaccgttg attcacacaa    180
ttggtcatcg cgcttggttg aaaagccagt ggcgcgaagc taccgtgtgc cggattatga    240
ctgaacgcct ctaagtcaga atccaagcta gcaagcggcg cctgcgcccg ccgccgccc    300 cgacccacgt taggggcgca agcccccaag ggcccgtgcc accggccaag ccggcccggc    360
cgacgcgccg cggccggccg cctcgaagct cccttcccaa cgggcggcgg gctgaatcct    420
ttgcagacga cttaaatacg cgacggggca ttgtaagtgg cagagtggcc ttgctgccac    480
gatccactga gatccagccc                                                500
```

```
<210> SEQ ID NO 31
<211> LENGTH: 500
<212> TYPE: DNA
<213> ORGANISM: Oryza rufipogon
<220> FEATURE:
<223> OTHER INFORMATION: A011C02 F: one terminus of DNA fragment
      A011C02.

<400> SEQUENCE: 31
tcgagttagg gatttgattg aagagtcaat catttagcca tgcactcaag tttcaagtta      60
gagatttgat tgaagagtca atcaatctct aacctgtggg ttaagtagat acatgccta     120 taaatatcga tatatttaga aatacggtaa ttaccatatt ataagaaacg gtaatttcca    180
caagaatacg gtaaatacga aaatgatcgg tacaacagca aaaccatttc cgtttctgtt    240
tccatatttt ttaccatttc catatttttt ggtcgattat catttccata tagctcggcc    300
ggttaaaagt aaaaaacgaa cgccagtcgg ccgggaatta ccgttaccat tttcacctct    360
aagccaaacg atggtggcct tagcatccac agttcaactt ccatctcaaa gaaaaaagaa    420
aaaggattga agcttcatgc cgagtgaaac catgggatgc tgtagtaaca cagacgctaa    480
agatcgcagc attacaaatt                                                500

<210> SEQ ID NO 32
<211> LENGTH: 500
<212> TYPE: DNA
<213> ORGANISM: Oryza rufipogon
<220> FEATURE:
<223> OTHER INFORMATION: A011C02 R: the other terminus of DNA fragment
      A011C02 to A011C02 F.

<400> SEQUENCE: 32
tcgaaggtgg tgtcaaatta tagccagcca atacatgaac aagttagaaa actgtcaaaa     60
cccaattcat caatagttga gatttgatgg tggtatatt ttttccttt tttctgatta     120 tgaccttta gggttgtaat cttgtaattt ttttctctgg aactttgcac ggttgttaaa    180
aaaaaacagt tgggacttt caagaaaaaa aaacggccg gagcactgtc aaacgaactc     240
actaataggc ctcgcaatct tattgggctt ttcacgaaca aaggcccata aaatgtagcc    300
catttaggcc caaactgtac atcacccgtg attaacggc ccagcccaaa catcataaca    360
ctggataggg tgcagacaag ggtcccaccc gtcagatccc gacacgtcat cattgccgat    420
ccgcttccag aagcagcggc aagtttccat ctccttcttc cccttggctt tttatcgctc    480
gatcaggtgg cagcgacaac                                                500

<210> SEQ ID NO 33
<211> LENGTH: 500
<212> TYPE: DNA
<213> ORGANISM: Oryza rufipogon
<220> FEATURE:
<223> OTHER INFORMATION: A010B03 F: one terminus of DNA fragment
      A010B03.

<400> SEQUENCE: 33
tcgaacagcc gactcagaac tggtacggac aaggggaatc cgactgttta attaaaacaa     60
agcattgcga tggtcctcgc ggatgctgac gcaatgtgat ttctgcccag tgctctgaat    120
gtcaaagtga agaaattcaa ccaagcgcgg gtaaacggcg ggagtaacta tgactctctt    180
aaggtagcca aatgcctcgt catctaatta gtgacgcgca tgaatggatt aacgagattc    240
ccactgtccc tgtctactat ccagcgaaac cacagccaag gaacgggct tggcggaatc    300 agcggggaaa gaagaccctg ttgagcttga ctctagtccg actttgtgaa atgacttgag    360
```

```
aggtgtagga taagtgggag ccctcgggcg caagtgaaat accactactt ttaacgttat    420
tttacttatt ccgtgagtcg gaagcgggc ctggcccctc cttttggctc taaggcccga    480
gtccctcggg ccgatccggg                                                500
```

<210> SEQ ID NO 34
<211> LENGTH: 500
<212> TYPE: DNA
<213> ORGANISM: Oryza rufipogon
<220> FEATURE:
<223> OTHER INFORMATION: A010B03 R: the other terminus of DNA fragment
      A010B03 to A010B03 F.

<400> SEQUENCE: 34

```
tcgaaggatc aaaaagcaac gtcgctatga acgcttggct gccacaagcc agttatccct    60
gtggtaactt ttctgacacc tctagcttca aactccgaag gtctaaagga tcgataggcc   120
acgctttcac ggttcgtatt cgtactggaa atcagaatca aacgagcttt tacccttttg   180
ttccacacga gatttctgtt ctcgttgagc tcatcttagg acacctgcgt tatcttttaa   240
cagatgtgcc gccccagcca aactcccac ctgacaatgt cttccgcccg gatcggcccg    300
agggactcgg gccttagagc caaaaggagg ggccaggccc cgcttccgac tcacggaata   360
agtaaaataa cgttaaaagt agtggtattt cacttgcgcc cgagggctcc cacttatcct   420
acacctctca agtcatttca caaagtcgga ctagagtcaa gctcaacagg gtcttctttc   480
cccgctgatt ccgccaagcc                                                500
```

<210> SEQ ID NO 35
<211> LENGTH: 500
<212> TYPE: DNA
<213> ORGANISM: Oryza rufipogon
<220> FEATURE:
<223> OTHER INFORMATION: A009F06 F: one terminus of DNA fragment
      A009F06.

<400> SEQUENCE: 35

```
tcgagtttga ttcggattcg ttttccccg aagtttcctt ctcgccgccg gtcgccgtgg    60
gcctccgtcg ccgcttgcta gccccttat aaggatcccc ggtgtctcct ctacccgccg   120
ccaccctcgc cttcgcctct cgccgccgcc agagccctag cgccgtgcaa ccttgcgccg   180
ccgtcgccgc cgtcgctcca atcgtgcgcc gccgtcgctc cagccgtcgc cgtcgctcgg   240
gaagaccgtc atcgtggtcg ccgtcgcgtc gccgtcctcg tccgccccctt cgccgtcgcc   300 ggagatcgcc ggagcgtcat cgccgccgtc gacccgaaga gcttcgccgt tcctcctcg    360 tcgccgtcac cgtccgttgc ctctccgccg tcgctttggt cgtcggtgag ttcgccgtgc   420
cgtccgctac ccgttggtgc cttccgtttg cgtcctcgcg ccgccgcccg agccgtccgc    480
tccgccgagc cgccgccgcc                                                500
```

<210> SEQ ID NO 36
<211> LENGTH: 500
<212> TYPE: DNA
<213> ORGANISM: Oryza rufipogon
<220> FEATURE:
<223> OTHER INFORMATION: A009F06 R: the other terminus of DNA fragment
      A009F06 to A009F06 F.

<400> SEQUENCE: 36

```
tcgaatagcc gtgccgcgg ttatgggcgg gtctaacaat gtctttcgtg attagtctca    60
cccttctcac catagtaaat gatgctataa ttggtaataa tttgattagc tcctggtttg   120
```

```
gaatggaata ttcctggttt ggagatagaa ctgtgcagcc gggatggttg ttcagattgg      180
ttgggcctat acaacagggg atgttgtata gcgttggatt aatactgctt aattaatatt      240
taactgtttt aaattctcaa atgtttgcta aatgctgctt ttgcaaatgg agccctatta      300
tgccatcctt tgttatcctg tgcacttgca tatttgctgc gtggcttgct gagtatgtca      360
tatactcacc ttgcaatcat tcattcagag gaagagttct tcagtgaagc tgatggtgtg      420
gaggattagg tgtagccttg gtcaagctgc ctgtggagtg gagccgtcta cgctgtttat      480
tttattttcc gctgcttaga                                                  500

<210> SEQ ID NO 37
<211> LENGTH: 500
<212> TYPE: DNA
<213> ORGANISM: Oryza rufipogon
<220> FEATURE:
<223> OTHER INFORMATION: A009E11 F: one terminus of DNA fragment
      A009E11.

<400> SEQUENCE: 37
tcgagttgga gcacgcctgt cgggacccga aagatggtga actatgcctg agcggggcga       60
agccagagga aactctggtg gaggctcgaa gcgatactga cgtgcaaatc gttcgtctga      120
cttgggtata ggggcgaaag actaatcgaa ccatctagta gctggttccc tccgaagttt      180
ccctcaggat agctggagcc cattacgagt tctatcgggt aaagccaatg attagaggca      240 tcggggcgc aacgccctcg acctattctc aaactttaaa taggtaggac ggcgcggctg       300
ctccggtgag ccgcgccacg gaatcgggag ctccaagtgg gccattttg gtaagcagaa       360 ctggcgatgc gggatgaacc ggaagcctgg ttacggtgcc gaactgcgcg ctaacctaga      420
acccacaaag ggtgttggtc gattaagaca gcaggacggt ggtcatggaa gtcgaaatcc      480
gctaaggagt gtgtaacaac                                                  500

<210> SEQ ID NO 38
<211> LENGTH: 500
<212> TYPE: DNA
<213> ORGANISM: Oryza rufipogon
<220> FEATURE:
<223> OTHER INFORMATION: A009E11 R: the other terminus of DNA fragment
      A009E11 to A009E11 F.

<400> SEQUENCE: 38
tcgaggcggc cggccgcggc gcgtcggccg ggccggcttg gccggtggca cgggcccttg       60
ggggcttgcg ccctaacgt gggtcgggc gggcggcggg cgcaggcgcc gcttgctagc       120
ttggattctg acttagaggc gttcagtcat aatccggcac acggtagctt cgcgccactg      180
gcttttcaac caagcgcgat gaccaattgt gtgaatcaac ggttcctctc gtactaggtt      240
gaattactat cgcggcacgg tcatcagtag ggtaaaacta acctgtctca cgacggtcta      300
aacccagctc acgttcccta ttggtgggtg aacaatccaa cacttggtga attctgcttc      360
acaatgatag gaagagccga catcgaagga tcaaaaagca acgtcgctat gaacgcttgg      420
ctgccacaag ccagttatcc ctgtggtaac ttttctgaca cctctagctt caaactccga      480
aggtctaaag gatcgatagg                                                  500

<210> SEQ ID NO 39
<211> LENGTH: 400
<212> TYPE: DNA
<213> ORGANISM: Oryza rufipogon
<220> FEATURE:
<223> OTHER INFORMATION: A008B02 F: one terminus of DNA fragment
      A008B02.
```

<400> SEQUENCE: 39

```
tcatatatta attctctctc tctaaaaata taaaaaaaag gagtctgcgc accgagatct    60
gccataaaag gtccaagcca taacaagtga gaagctatac ggctcaattc taacataatt   120
accctaatat agctggctct ttggggtatt tgaatattct ccaagaattc tggtgcattt   180
accgttattg cttctgtaaa catagtagct aaataatccc aacgtgttac ataaggtaag   240
tattgtataa tagttcggtt ttccgcgatt ttttccattc ctctgtgtaa atagcctaat   300
atgggttcac aatcaataac atcttcacca tcgagagtaa cgatcagtcg aagaacacca   360
tgcattgatg ggtgctgagg gcccatattg actatcatga                         400
```

<210> SEQ ID NO 40
<211> LENGTH: 400
<212> TYPE: DNA
<213> ORGANISM: Oryza rufipogon
<220> FEATURE:
<223> OTHER INFORMATION: A008B02 R: the other terminus of DNA fragment
      A008B02 to A008B02 F.

<400> SEQUENCE: 40

```
tcgaagacgc ggaatggtag tgaatagaga gaaagattct tctggttttc ttgttcctga    60
aaatattcta tctatctcct agacgccgta gagaattgag aattttcatg tctttcaatt   120
ctcgtactcg taattggaaa gttacggaag gagatccatc attttgcaat gaaaactaca   180
taaaaactc tggacaattt cgaaatcagg ccaagcgtct taatacatat gcaaaaaaat   240
tcattattgg cccaccattg attagaagat ttaacttgta tgaatcgcta ttggtttgat   300
acgaataatg gcagttgttt cagtatgtta aggatacaga tgtatccaca attcatttag   360
agttacttaa tagcctattt cttataccat atctctatcc                         400
```

<210> SEQ ID NO 41
<211> LENGTH: 400
<212> TYPE: DNA
<213> ORGANISM: Oryza rufipogon
<220> FEATURE:
<223> OTHER INFORMATION: A083G04 F: one terminus of DNA fragment
      A083G04.

<400> SEQUENCE: 41

```
tcgatggtag gatagggcc taccatggtg gtgacgggtg acggagaatt agggttcgat     60
tccggagagg gagcctgaga aacggctacc acatccaagg aaggcagcag gcgcgcaaat   120
tacccaatcc tgacacgggg aggtagtgac aataaataac aataccgggc gctttagtgt   180
ctggtaattg gaatgagtac aatctaaatc ccttaacgag gatccattgg agggcaagtc   240
tggtgccagc agccgcggta attccagctc caatagcgta tatttaagtt gttgcagtta   300
aaaagctcgt agttggacct tgggccgggc cggccggtcc gcctcacggc gagcaccgac   360
ctgctcgacc cttctgccgg cgatgcgctc ctggccttaa                         400
```

<210> SEQ ID NO 42
<211> LENGTH: 360
<212> TYPE: DNA
<213> ORGANISM: Oryza rufipogon
<220> FEATURE:
<223> OTHER INFORMATION: A083G04 R: the other terminus of DNA fragment
      A083G04 to A083G04 F.

<400> SEQUENCE: 42

```
tcgagttatc atgaatcatc ggatcagcgg gcggagcccg cgtcagcctt ttatctaata    60
```

```
aatgcgcccc tcccggaagt cggggtttgt tgcacgtatt agctctagaa ttactacggt    120
tatccgagta gcacgtacca tcaaacaaac tataactgat ttaatgagcc attcgcagtt    180
tcacagttcg aattagttca tacttgcaca tgcatggctt aatctttgag acaagcatat    240
gactactggc aggatcaacc aggtagcacg tcctccgcga cgagcccgcg ccgtccgacg    300
cgcgtcgccg ccgccccgg gtcgggagcg gcggacacgg cggcggccgg gcgggctgtc     360
```

<210> SEQ ID NO 43
<211> LENGTH: 400
<212> TYPE: DNA
<213> ORGANISM: Oryza rufipogon
<220> FEATURE:
<223> OTHER INFORMATION: A088E02 F: one terminus of DNA fragment
      A088E02.

<400> SEQUENCE: 43

```
tcgagcctcc accagagttt cctctggctt cgccccgctc aggcatagtt caccatcttt     60
cgggtcccga caggcgtgct ccaactcgaa cccttcacag aagatcaggg tcggccagcg    120
gtgcggcccg tgagggcctc ccgctcgtca gcttccttgc gcatcccagg tttcagaacc    180
cgtcgactcg cacgcatgtc agactccttg gtccgtgttt caagacgggt cggatgggga    240
gcccgcaggc cgttgcagcg cagcgccccg aggggcgcgc cagaggcgcg cggtgaccgg    300
ctgcgccgac gacggctgcc ggggcgcgg agccccggg cttggccgc ggcgcggcc        360 gacaacggtc cacgccccga ccgatcggc ggaccagccg                           400
```

<210> SEQ ID NO 44
<211> LENGTH: 400
<212> TYPE: DNA
<213> ORGANISM: Oryza rufipogon
<220> FEATURE:
<223> OTHER INFORMATION: A088E02 R: the other terminus of DNA fragment
      A088E02 to A088E02 F.

<400> SEQUENCE: 44

```
tccaggcgtg gagcctgcgg cttaatttga ctcaacacgg ggaaacttac caggtccaga     60
catagcaagg attgacagac tgagagctct ttcttgattc tatgggtggt ggtgcatggc    120
cgttcttagt tggtggagcg atttgtctgg ttaattccgt taacgaacga gacctcagcc    180
tactaactag ctatgcggag ccatccctcc gcagctagct tcttagaggg actatggccg    240
tttaggccac ggaagtttga ggcaataaca ggtctgtgat gcccttagat gttctgggcc    300
gcacgcgcgc tacactgatg tattcaacga gtatatagcc ttggccgaca ggcccgggta    360
atcttgggaa atttcatcgt gatggggata gatcattgca                          400
```

<210> SEQ ID NO 45
<211> LENGTH: 400
<212> TYPE: DNA
<213> ORGANISM: Oryza rufipogon
<220> FEATURE:
<223> OTHER INFORMATION: A089F12 F: one terminus of DNA fragment
      A089F12.

<400> SEQUENCE: 45

```
tcgagcagtc cgccggcagc cgacgggttc ggggccggga ccccgagcc cagccctcag      60 agccaatcct tttcccgaag ttacggatcc gttttgccga cttcccttgc ctacattgtt    120
ccattggcca gaggctgttc accttggaga cctgatgcgg ttatgagtac gacccggcgt    180
ggacggtact cggtcctccg gatttttcaag ggccgccggg ggcgcaccgg acaccgcgcg   240
acgtgcggtg ctcttccggc cgctggaccc tacctccggc tgaaccgttt ccagggttgg    300
```

```
cgggccgtta agcagaaaag ataactcttc ccgaggcccc cgccggcgtc tccggacttc    360
ctaacgtcgc cgtcaaccgc cacgtcccgg ctcgggaaat                          400
```

<210> SEQ ID NO 46
<211> LENGTH: 360
<212> TYPE: DNA
<213> ORGANISM: Oryza rufipogon
<220> FEATURE:
<223> OTHER INFORMATION: A089F12 R: the other terminus of DNA fragment
      A089F12 to A089F12 F.

<400> SEQUENCE: 46

```
tcgaacagcc gactcagaac tggtacggac aaggggaatc cgactgttta attaaaacaa    60
agcattgcga tggtcctcgc ggatgctgac gcaatgtgat ttctgcccag tgctctgaat   120
gtcaaagtga agaaattcaa ccaagcgcgg gtaaacggcg ggagtaacta tgactctctt   180
aaggtagcca aatgcctcgt catctaatta gtgacgcgca tgaatggatt aacgagattc   240
ccactgtccc tgtctactat ccagcgaaac cacagccaag ggaacgggct tggcggaatc   300
agcggggaaa gaagaccctg ttgagcttga ctctagtccg actttgtgaa atgacttgag   360
```

<210> SEQ ID NO 47
<211> LENGTH: 24
<212> TYPE: DNA
<213> ORGANISM: artificial sequence
<220> FEATURE:
<223> OTHER INFORMATION: forward primer for amplifying DNA fragment
      A029B04 F.

<400> SEQUENCE: 47

```
tcgaatttga ccatgagata caga                                           24
```

<210> SEQ ID NO 48
<211> LENGTH: 24
<212> TYPE: DNA
<213> ORGANISM: artificial sequence
<220> FEATURE:
<223> OTHER INFORMATION: reverse primer for amplifying DNA fragment
      A029B04 F.

<400> SEQUENCE: 48

```
aagaaaaaaa tgcttgtgta ctga                                           24
```

<210> SEQ ID NO 49
<211> LENGTH: 24
<212> TYPE: DNA
<213> ORGANISM: artificial sequence
<220> FEATURE:
<223> OTHER INFORMATION: forward primer for amplifying DNA fragment
      A029B04 R.

<400> SEQUENCE: 49

```
tcgagctaat taactagcca agtg                                           24
```

<210> SEQ ID NO 50
<211> LENGTH: 24
<212> TYPE: DNA
<213> ORGANISM: artificial sequence
<220> FEATURE:
<223> OTHER INFORMATION: reverse primer for amplifying DNA fragment
      A029B04 R.

<400> SEQUENCE: 50

```
aagtaacatg agaaaaaaaa acat                                           24
```

```
<210> SEQ ID NO 51
<211> LENGTH: 24
<212> TYPE: DNA
<213> ORGANISM: artificial sequence
<220> FEATURE:
<223> OTHER INFORMATION: forward primer for amplifying DNA fragment
      A028C04 F.

<400> SEQUENCE: 51
tcgattaaga cagcaggacg gtgg                                              24

<210> SEQ ID NO 52
<211> LENGTH: 24
<212> TYPE: DNA
<213> ORGANISM: artificial sequence
<220> FEATURE:
<223> OTHER INFORMATION: reverse primer for amplifying DNA fragment
      A028C04 F.

<400> SEQUENCE: 52
gcaagtgccg ttcacatgga acct                                              24

<210> SEQ ID NO 53
<211> LENGTH: 24
<212> TYPE: DNA
<213> ORGANISM: artificial sequence
<220> FEATURE:
<223> OTHER INFORMATION: forward primer for amplifying DNA fragment
      A028C04 R.

<400> SEQUENCE: 53
tcgagggcgt tgcgccccg atgc                                               24

<210> SEQ ID NO 54
<211> LENGTH: 24
<212> TYPE: DNA
<213> ORGANISM: artificial sequence
<220> FEATURE:
<223> OTHER INFORMATION: reverse primer for amplifying DNA fragment
      A028C04 R.

<400> SEQUENCE: 54
ccgtcttgaa acacggacca agga                                              24

<210> SEQ ID NO 55
<211> LENGTH: 24
<212> TYPE: DNA
<213> ORGANISM: artificial sequence
<220> FEATURE:
<223> OTHER INFORMATION: forward primer for amplifying DNA fragment
      A048F12 F.

<400> SEQUENCE: 55
tcgatgtagt cctcctcgag gccg                                              24

<210> SEQ ID NO 56
<211> LENGTH: 24
<212> TYPE: DNA
<213> ORGANISM: artificial sequence
<220> FEATURE:
<223> OTHER INFORMATION: reverse primer for amplifying DNA fragment
      A048F12 F.

<400> SEQUENCE: 56
caacaaccga gcaatacagt tcaa                                              24

<210> SEQ ID NO 57
```

```
<211> LENGTH: 24
<212> TYPE: DNA
<213> ORGANISM: artificial sequence
<220> FEATURE:
<223> OTHER INFORMATION: forward primer for amplifying DNA fragment
      A048F12 R.

<400> SEQUENCE: 57
tcgagtggtc ggcgtccccc ggcc                                          24

<210> SEQ ID NO 58
<211> LENGTH: 24
<212> TYPE: DNA
<213> ORGANISM: artificial sequence
<220> FEATURE:
<223> OTHER INFORMATION: reverse primer for amplifying DNA fragment
      A048F12 R.

<400> SEQUENCE: 58
ccggagttca ccatgccccg gggc                                          24

<210> SEQ ID NO 59
<211> LENGTH: 24
<212> TYPE: DNA
<213> ORGANISM: artificial sequence
<220> FEATURE:
<223> OTHER INFORMATION: forward primer for amplifying DNA fragment
      A049A01 F.

<400> SEQUENCE: 59
tcgaactaac gctaacaacg tgca                                          24

<210> SEQ ID NO 60
<211> LENGTH: 24
<212> TYPE: DNA
<213> ORGANISM: artificial sequence
<220> FEATURE:
<223> OTHER INFORMATION: reverse primer for amplifying DNA fragment
      A049A01 F.

<400> SEQUENCE: 60
atttggcgca tctgaacact gaac                                          24

<210> SEQ ID NO 61
<211> LENGTH: 24
<212> TYPE: DNA
<213> ORGANISM: artificial sequence
<220> FEATURE:
<223> OTHER INFORMATION: forward primer for amplifying DNA fragment
      A049A01 R.

<400> SEQUENCE: 61
tcgagtgcca tcctcttctc aatg                                          24

<210> SEQ ID NO 62
<211> LENGTH: 24
<212> TYPE: DNA
<213> ORGANISM: artificial sequence
<220> FEATURE:
<223> OTHER INFORMATION: reverse primer for amplifying DNA fragment
      A049A01 R.

<400> SEQUENCE: 62
gtttttgttc gttacaatga gaac                                          24

<210> SEQ ID NO 63
<211> LENGTH: 24
<212> TYPE: DNA
```

```
<213> ORGANISM: artificial sequence
<220> FEATURE:
<223> OTHER INFORMATION: forward primer for amplifying DNA fragment
      A046A06 F.

<400> SEQUENCE: 63
tcgaactacc gagctccccc taat                                          24

<210> SEQ ID NO 64
<211> LENGTH: 24
<212> TYPE: DNA
<213> ORGANISM: artificial sequence
<220> FEATURE:
<223> OTHER INFORMATION: reverse primer for amplifying DNA fragment
      A046A06 F.

<400> SEQUENCE: 64
gtagctgaaa ggcgtaaccg tacc                                          24

<210> SEQ ID NO 65
<211> LENGTH: 24
<212> TYPE: DNA
<213> ORGANISM: artificial sequence
<220> FEATURE:
<223> OTHER INFORMATION: forward primer for amplifying DNA fragment
      A046A06 R.

<400> SEQUENCE: 65
tcgaacttgt cttccaattt gcgt                                          24

<210> SEQ ID NO 66
<211> LENGTH: 24
<212> TYPE: DNA
<213> ORGANISM: artificial sequence
<220> FEATURE:
<223> OTHER INFORMATION: reverse primer for amplifying DNA fragment
      A046A06 R.

<400> SEQUENCE: 66
aaccccgaac ttcaatcaag tccc                                          24

<210> SEQ ID NO 67
<211> LENGTH: 24
<212> TYPE: DNA
<213> ORGANISM: artificial sequence
<220> FEATURE:
<223> OTHER INFORMATION: forward primer for amplifying DNA fragment
      A045B09 F.

<400> SEQUENCE: 67
tcgacgacga cgcggcgaag ccga                                          24

<210> SEQ ID NO 68
<211> LENGTH: 24
<212> TYPE: DNA
<213> ORGANISM: artificial sequence
<220> FEATURE:
<223> OTHER INFORMATION: reverse primer for amplifying DNA fragment
      A045B09 F.

<400> SEQUENCE: 68
ccgccgcatc ccgccgtccc cgcg                                          24

<210> SEQ ID NO 69
<211> LENGTH: 24
<212> TYPE: DNA
<213> ORGANISM: artificial sequence
<220> FEATURE:
```

```
<223> OTHER INFORMATION: forward primer for amplifying DNA fragment
      A045B09 R.

<400> SEQUENCE: 69
tcgaggatgc ctgtggagtg gtgt                                          24

<210> SEQ ID NO 70
<211> LENGTH: 24
<212> TYPE: DNA
<213> ORGANISM: artificial sequence
<220> FEATURE:
<223> OTHER INFORMATION: reverse primer for amplifying DNA fragment
      A045B09 R.

<400> SEQUENCE: 70
ccgtggaccg ccgcttcgtt tccc                                          24

<210> SEQ ID NO 71
<211> LENGTH: 24
<212> TYPE: DNA
<213> ORGANISM: artificial sequence
<220> FEATURE:
<223> OTHER INFORMATION: forward primer for amplifying DNA fragment
      A049A07 F.

<400> SEQUENCE: 71
tcgagcagtc cgccggcagc cgac                                          24

<210> SEQ ID NO 72
<211> LENGTH: 24
<212> TYPE: DNA
<213> ORGANISM: artificial sequence
<220> FEATURE:
<223> OTHER INFORMATION: reverse primer for amplifying DNA fragment
      A049A07 F.

<400> SEQUENCE: 72
atttcccgag ccgggacgtg gcgg                                          24

<210> SEQ ID NO 73
<211> LENGTH: 24
<212> TYPE: DNA
<213> ORGANISM: artificial sequence
<220> FEATURE:
<223> OTHER INFORMATION: forward primer for amplifying DNA fragment
      A049A07 R.

<400> SEQUENCE: 73
tcgaaccatc tagtagctgg ttcc                                          24

<210> SEQ ID NO 74
<211> LENGTH: 24
<212> TYPE: DNA
<213> ORGANISM: artificial sequence
<220> FEATURE:
<223> OTHER INFORMATION: reverse primer for amplifying DNA fragment
      A049A07 R.

<400> SEQUENCE: 74
gcttcagcgc catccatttt cggg                                          24

<210> SEQ ID NO 75
<211> LENGTH: 24
<212> TYPE: DNA
<213> ORGANISM: artificial sequence
<220> FEATURE:
<223> OTHER INFORMATION: forward primer for amplifying DNA fragment
      A040D06 F.
```

```
<400> SEQUENCE: 75
tcgacgggtt ctgaaacctg ggat                                              24

<210> SEQ ID NO 76
<211> LENGTH: 24
<212> TYPE: DNA
<213> ORGANISM: artificial sequence
<220> FEATURE:
<223> OTHER INFORMATION: reverse primer for amplifying DNA fragment
      A040D06 F.

<400> SEQUENCE: 76
gagcagccgc gccgtcctac ctat                                              24

<210> SEQ ID NO 77
<211> LENGTH: 24
<212> TYPE: DNA
<213> ORGANISM: artificial sequence
<220> FEATURE:
<223> OTHER INFORMATION: forward primer for amplifying DNA fragment
      A040D06 R.

<400> SEQUENCE: 77
tcgagccccc aactttcgtt cttg                                              24

<210> SEQ ID NO 78
<211> LENGTH: 24
<212> TYPE: DNA
<213> ORGANISM: artificial sequence
<220> FEATURE:
<223> OTHER INFORMATION: reverse primer for amplifying DNA fragment
      A040D06 R.

<400> SEQUENCE: 78
agcgtatatt taagttgttg cagt                                              24

<210> SEQ ID NO 79
<211> LENGTH: 24
<212> TYPE: DNA
<213> ORGANISM: artificial sequence
<220> FEATURE:
<223> OTHER INFORMATION: forward primer for amplifying DNA fragment
      A036A03 F.

<400> SEQUENCE: 79
tcgaaaatga ccgtcaacaa aacc                                              24

<210> SEQ ID NO 80
<211> LENGTH: 24
<212> TYPE: DNA
<213> ORGANISM: artificial sequence
<220> FEATURE:
<223> OTHER INFORMATION: reverse primer for amplifying DNA fragment
      A036A03 F.

<400> SEQUENCE: 80
atcaaaaagg catcatttgg tgag                                              24

<210> SEQ ID NO 81
<211> LENGTH: 24
<212> TYPE: DNA
<213> ORGANISM: artificial sequence
<220> FEATURE:
<223> OTHER INFORMATION: forward primer for amplifying DNA fragment
      A036A03 R.

<400> SEQUENCE: 81
```

```
tcgatgcatt gagcagaaag gaat                                          24
```

<210> SEQ ID NO 82
<211> LENGTH: 24
<212> TYPE: DNA
<213> ORGANISM: artificial sequence
<220> FEATURE:
<223> OTHER INFORMATION: reverse primer for amplifying DNA fragment
      A036A03 R.

<400> SEQUENCE: 82

```
atattcttcc accaaaaagt atct                                          24
```

<210> SEQ ID NO 83
<211> LENGTH: 24
<212> TYPE: DNA
<213> ORGANISM: artificial sequence
<220> FEATURE:
<223> OTHER INFORMATION: forward primer for amplifying DNA fragment
      A051E08 F.

<400> SEQUENCE: 83

```
tcgatgaaga acgtagcgaa atgc                                          24
```

<210> SEQ ID NO 84
<211> LENGTH: 24
<212> TYPE: DNA
<213> ORGANISM: artificial sequence
<220> FEATURE:
<223> OTHER INFORMATION: reverse primer for amplifying DNA fragment
      A051E08 F.

<400> SEQUENCE: 84

```
atatgcttaa actcagcggg tagt                                          24
```

<210> SEQ ID NO 85
<211> LENGTH: 24
<212> TYPE: DNA
<213> ORGANISM: artificial sequence
<220> FEATURE:
<223> OTHER INFORMATION: forward primer for amplifying DNA fragment
      A051E08 R.

<400> SEQUENCE: 85

```
tcgatgcgag agccgagata tccg                                          24
```

<210> SEQ ID NO 86
<211> LENGTH: 24
<212> TYPE: DNA
<213> ORGANISM: artificial sequence
<220> FEATURE:
<223> OTHER INFORMATION: reverse primer for amplifying DNA fragment
      A051E08 R

<400> SEQUENCE: 86

```
cccgtcgctc ctaccgattg aatg                                          24
```

<210> SEQ ID NO 87
<211> LENGTH: 24
<212> TYPE: DNA
<213> ORGANISM: artificial sequence
<220> FEATURE:
<223> OTHER INFORMATION: forward primer for amplifying DNA fragment
      A023D09 F.

<400> SEQUENCE: 87

```
tcgacgccat actgatgagc aatg                                          24
```

<210> SEQ ID NO 88
<211> LENGTH: 24
<212> TYPE: DNA
<213> ORGANISM: artificial sequence
<220> FEATURE:
<223> OTHER INFORMATION: reverse primer for amplifying DNA fragment
      A023D09 F.

<400> SEQUENCE: 88
gttgatgctc ttctctgcgt catc                                             24

<210> SEQ ID NO 89
<211> LENGTH: 24
<212> TYPE: DNA
<213> ORGANISM: artificial sequence
<220> FEATURE:
<223> OTHER INFORMATION: forward primer for amplifying DNA fragment
      A023D09 R.

<400> SEQUENCE: 89
tcgaatgcca gttaaagtga tgcc                                             24

<210> SEQ ID NO 90
<211> LENGTH: 24
<212> TYPE: DNA
<213> ORGANISM: artificial sequence
<220> FEATURE:
<223> OTHER INFORMATION: reverse primer for amplifying DNA fragment
      A023D09 R.

<400> SEQUENCE: 90
ctactgcgcc gagcccacgc tgag                                             24

<210> SEQ ID NO 91
<211> LENGTH: 24
<212> TYPE: DNA
<213> ORGANISM: artificial sequence
<220> FEATURE:
<223> OTHER INFORMATION: forward primer for amplifying DNA fragment
      A030B02 F.

<400> SEQUENCE: 91
tcgaagcttc acagttgata actt                                             24

<210> SEQ ID NO 92
<211> LENGTH: 24
<212> TYPE: DNA
<213> ORGANISM: artificial sequence
<220> FEATURE:
<223> OTHER INFORMATION: reverse primer for amplifying DNA fragment
      A030B02 F.

<400> SEQUENCE: 92
gaggtttcga acccaggttg tcta                                             24

<210> SEQ ID NO 93
<211> LENGTH: 24
<212> TYPE: DNA
<213> ORGANISM: artificial sequence
<220> FEATURE:
<223> OTHER INFORMATION: forward primer for amplifying DNA fragment
      A030B02 R.

<400> SEQUENCE: 93
tcgaggtgaa ctattttttt tctt                                             24

```
<210> SEQ ID NO 94
<211> LENGTH: 24
<212> TYPE: DNA
<213> ORGANISM: artificial sequence
<220> FEATURE:
<223> OTHER INFORMATION: reverse primer for amplifying DNA fragment
      A030B02 R.

<400> SEQUENCE: 94
ggccctcggg gccgaggcgg gagt                                            24

<210> SEQ ID NO 95
<211> LENGTH: 24
<212> TYPE: DNA
<213> ORGANISM: artificial sequence
<220> FEATURE:
<223> OTHER INFORMATION: forward primer for amplifying DNA fragment
      A043F04 F.

<400> SEQUENCE: 95
tcgaccacct tctcagaagc aaaa                                            24

<210> SEQ ID NO 96
<211> LENGTH: 24
<212> TYPE: DNA
<213> ORGANISM: artificial sequence
<220> FEATURE:
<223> OTHER INFORMATION: reverse primer for amplifying DNA fragment
      A043F04 F.

<400> SEQUENCE: 96
aacatccaac agattgagac actt                                            24

<210> SEQ ID NO 97
<211> LENGTH: 24
<212> TYPE: DNA
<213> ORGANISM: artificial sequence
<220> FEATURE:
<223> OTHER INFORMATION: forward primer for amplifying DNA fragment
      A043F04 R.

<400> SEQUENCE: 97
tcgatagcac cattgggact atac                                            24

<210> SEQ ID NO 98
<211> LENGTH: 24
<212> TYPE: DNA
<213> ORGANISM: artificial sequence
<220> FEATURE:
<223> OTHER INFORMATION: reverse primer for amplifying DNA fragment
      A043F04 R.

<400> SEQUENCE: 98
tgattcgaac aaatttaggg tatt                                            24

<210> SEQ ID NO 99
<211> LENGTH: 24
<212> TYPE: DNA
<213> ORGANISM: artificial sequence
<220> FEATURE:
<223> OTHER INFORMATION: forward primer for amplifying DNA fragment
      A049E02 F.

<400> SEQUENCE: 99
tcgattaaga cagcaggacg gtgg                                            24

<210> SEQ ID NO 100
<211> LENGTH: 24
```

```
<212> TYPE: DNA
<213> ORGANISM: artificial sequence
<220> FEATURE:
<223> OTHER INFORMATION: reverse primer for amplifying DNA fragment
      A049E02 F.

<400> SEQUENCE: 100
cccggctcgg gaaatcttaa cccg                                         24

<210> SEQ ID NO 101
<211> LENGTH: 24
<212> TYPE: DNA
<213> ORGANISM: artificial sequence
<220> FEATURE:
<223> OTHER INFORMATION: forward primer for amplifying DNA fragment
      A049E02 R.

<400> SEQUENCE: 101
tcgaccgaat cgggttttcg gtcg                                         24

<210> SEQ ID NO 102
<211> LENGTH: 24
<212> TYPE: DNA
<213> ORGANISM: artificial sequence
<220> FEATURE:
<223> OTHER INFORMATION: reverse primer for amplifying DNA fragment
      A049E02 R.

<400> SEQUENCE: 102
ggatggccgg gctgccacgc gcac                                         24

<210> SEQ ID NO 103
<211> LENGTH: 20
<212> TYPE: DNA
<213> ORGANISM: artificial sequence
<220> FEATURE:
<223> OTHER INFORMATION: forward primer for amplifying DNA fragment
      A010C09 F.

<400> SEQUENCE: 103
tcgaccgaat cgggttttcg                                              20

<210> SEQ ID NO 104
<211> LENGTH: 20
<212> TYPE: DNA
<213> ORGANISM: artificial sequence
<220> FEATURE:
<223> OTHER INFORMATION: reverse primer for amplifying DNA fragment
      A010C09 F.

<400> SEQUENCE: 104
accgaaaact gtgtgcgagc                                              20

<210> SEQ ID NO 105
<211> LENGTH: 20
<212> TYPE: DNA
<213> ORGANISM: artificial sequence
<220> FEATURE:
<223> OTHER INFORMATION: forward primer for amplifying DNA fragment
      A010C09 R.

<400> SEQUENCE: 105
tcgatgtcgg ctcttcctat                                              20

<210> SEQ ID NO 106
<211> LENGTH: 20
<212> TYPE: DNA
<213> ORGANISM: artificial sequence
```

```
<220> FEATURE:
<223> OTHER INFORMATION: reverse primer for amplifying DNA fragment
      A010C09 R.

<400> SEQUENCE: 106
gggctggatc tcagtggatc                                              20

<210> SEQ ID NO 107
<211> LENGTH: 20
<212> TYPE: DNA
<213> ORGANISM: artificial sequence
<220> FEATURE:
<223> OTHER INFORMATION: forward primer for amplifying DNA fragment
      A011C02 F.

<400> SEQUENCE: 107
tcgagttagg gatttgattg                                              20

<210> SEQ ID NO 108
<211> LENGTH: 20
<212> TYPE: DNA
<213> ORGANISM: artificial sequence
<220> FEATURE:
<223> OTHER INFORMATION: reverse primer for amplifying DNA fragment
      A011C02 F.

<400> SEQUENCE: 108
aatttgtaat gctgcgatct                                              20

<210> SEQ ID NO 109
<211> LENGTH: 20
<212> TYPE: DNA
<213> ORGANISM: artificial sequence
<220> FEATURE:
<223> OTHER INFORMATION: forward primer for amplifying DNA fragment
      A011C02 R.

<400> SEQUENCE: 109
tcgaaggtgg tgtcaaatta                                              20

<210> SEQ ID NO 110
<211> LENGTH: 20
<212> TYPE: DNA
<213> ORGANISM: artificial sequence
<220> FEATURE:
<223> OTHER INFORMATION: reverse primer for amplifying DNA fragment
      A011C02 R.

<400> SEQUENCE: 110
gttgtcgctg ccacctgatc                                              20

<210> SEQ ID NO 111
<211> LENGTH: 20
<212> TYPE: DNA
<213> ORGANISM: artificial sequence
<220> FEATURE:
<223> OTHER INFORMATION: forward primer for amplifying DNA fragment
      A010B03 F.

<400> SEQUENCE: 111
tcgaacagcc gactcagaac                                              20

<210> SEQ ID NO 112
<211> LENGTH: 20
<212> TYPE: DNA
<213> ORGANISM: artificial sequence
<220> FEATURE:
<223> OTHER INFORMATION: reverse primer for amplifying DNA fragment
```

A010B03 F.

<400> SEQUENCE: 112
cccggatcgg cccgagggac                                        20

<210> SEQ ID NO 113
<211> LENGTH: 20
<212> TYPE: DNA
<213> ORGANISM: artificial sequence
<220> FEATURE:
<223> OTHER INFORMATION: forward primer for amplifying DNA fragment
      A010B03 R.

<400> SEQUENCE: 113
tcgaaggatc aaaaagcaac                                        20

<210> SEQ ID NO 114
<211> LENGTH: 20
<212> TYPE: DNA
<213> ORGANISM: artificial sequence
<220> FEATURE:
<223> OTHER INFORMATION: reverse primer for amplifying DNA fragment
      A010B03 R.

<400> SEQUENCE: 114
ggcttggcgg aatcagcggg                                        20

<210> SEQ ID NO 115
<211> LENGTH: 20
<212> TYPE: DNA
<213> ORGANISM: artificial sequence
<220> FEATURE:
<223> OTHER INFORMATION: forward primer for amplifying DNA fragment
      A009F06 F.

<400> SEQUENCE: 115
tcgagtttga ttcggattcg                                        20

<210> SEQ ID NO 116
<211> LENGTH: 20
<212> TYPE: DNA
<213> ORGANISM: artificial sequence
<220> FEATURE:
<223> OTHER INFORMATION: reverse primer for amplifying DNA fragment
      A009F06 F.

<400> SEQUENCE: 116
ggcggcggcg gctcggcgga                                        20

<210> SEQ ID NO 117
<211> LENGTH: 20
<212> TYPE: DNA
<213> ORGANISM: artificial sequence
<220> FEATURE:
<223> OTHER INFORMATION: forward primer for amplifying DNA fragment
      A009F06 R.

<400> SEQUENCE: 117
tcgaatagcc gtgcccgcgg                                        20

<210> SEQ ID NO 118
<211> LENGTH: 20
<212> TYPE: DNA
<213> ORGANISM: artificial sequence
<220> FEATURE:
<223> OTHER INFORMATION: reverse primer for amplifying DNA fragment
      A009F06 R.

-continued

```
<400> SEQUENCE: 118
tctaagcagc ggaaaataaa                                              20

<210> SEQ ID NO 119
<211> LENGTH: 20
<212> TYPE: DNA
<213> ORGANISM: artificial sequence
<220> FEATURE:
<223> OTHER INFORMATION: forward primer for amplifying DNA fragment
      A009E11 F.

<400> SEQUENCE: 119
tcgagttgga gcacgcctgt                                              20

<210> SEQ ID NO 120
<211> LENGTH: 20
<212> TYPE: DNA
<213> ORGANISM: artificial sequence
<220> FEATURE:
<223> OTHER INFORMATION: reverse primer for amplifying DNA fragment
      A009E11 F.

<400> SEQUENCE: 120
gttgttacac actccttagc                                              20

<210> SEQ ID NO 121
<211> LENGTH: 20
<212> TYPE: DNA
<213> ORGANISM: artificial sequence
<220> FEATURE:
<223> OTHER INFORMATION: forward primer for amplifying DNA fragment
      A009E11 R.

<400> SEQUENCE: 121
tcgaggcggc cggccgcggc                                              20

<210> SEQ ID NO 122
<211> LENGTH: 20
<212> TYPE: DNA
<213> ORGANISM: artificial sequence
<220> FEATURE:
<223> OTHER INFORMATION: reverse primer for amplifying DNA fragment
      A009E11 R.

<400> SEQUENCE: 122
cctatcgatc ctttagacct                                              20

<210> SEQ ID NO 123
<211> LENGTH: 24
<212> TYPE: DNA
<213> ORGANISM: artificial sequence
<220> FEATURE:
<223> OTHER INFORMATION: forward primer for amplifying DNA fragment
      A008B02 F.

<400> SEQUENCE: 123
tcatatatta attctctctc tcta                                         24

<210> SEQ ID NO 124
<211> LENGTH: 24
<212> TYPE: DNA
<213> ORGANISM: artificial sequence
<220> FEATURE:
<223> OTHER INFORMATION: reverse primer for amplifying DNA fragment
      A008B02 F.

<400> SEQUENCE: 124
```
tcatgatagt caatatgggc cctc                                          24

<210> SEQ ID NO 125
<211> LENGTH: 24
<212> TYPE: DNA
<213> ORGANISM: artificial sequence
<220> FEATURE:
<223> OTHER INFORMATION: forward primer for amplifying DNA fragment
      A008B02 R.

<400> SEQUENCE: 125
tcgaagacgc ggaatggtag tgaa                                          24

<210> SEQ ID NO 126
<211> LENGTH: 24
<212> TYPE: DNA
<213> ORGANISM: artificial sequence
<220> FEATURE:
<223> OTHER INFORMATION: reverse primer for amplifying DNA fragment
      A008B02 R.

<400> SEQUENCE: 126
ggatagagat atggtataag aaat                                          24

<210> SEQ ID NO 127
<211> LENGTH: 24
<212> TYPE: DNA
<213> ORGANISM: artificial sequence
<220> FEATURE:
<223> OTHER INFORMATION: forward primer for amplifying DNA fragment
      A083G04 F.

<400> SEQUENCE: 127
tcgatggtag gataggggcc tacc                                          24

<210> SEQ ID NO 128
<211> LENGTH: 24
<212> TYPE: DNA
<213> ORGANISM: artificial sequence
<220> FEATURE:
<223> OTHER INFORMATION: reverse primer for amplifying DNA fragment
      A083G04 F.

<400> SEQUENCE: 128
ttaaggccag gagcgcatcg ccgg                                          24

<210> SEQ ID NO 129
<211> LENGTH: 24
<212> TYPE: DNA
<213> ORGANISM: artificial sequence
<220> FEATURE:
<223> OTHER INFORMATION: forward primer for amplifying DNA fragment
      A083G04 R.

<400> SEQUENCE: 129
tcgagttatc atgaatcatc ggat                                          24

<210> SEQ ID NO 130
<211> LENGTH: 24
<212> TYPE: DNA
<213> ORGANISM: artificial sequence
<220> FEATURE:
<223> OTHER INFORMATION: reverse primer for amplifying DNA fragment
      A083G04 R.

<400> SEQUENCE: 130
gacagcccgc ccggccgccg ccgt                                          24

<210> SEQ ID NO 131
<211> LENGTH: 24
<212> TYPE: DNA
<213> ORGANISM: artificial sequence
<220> FEATURE:
<223> OTHER INFORMATION: forward primer for amplifying DNA fragment
    A088E02 F.

<400> SEQUENCE: 131
tcgagcctcc accagagttt cctc                                         24

<210> SEQ ID NO 132
<211> LENGTH: 24
<212> TYPE: DNA
<213> ORGANISM: artificial sequence
<220> FEATURE:
<223> OTHER INFORMATION: reverse primer for amplifying DNA fragment
    A088E02 F.

<400> SEQUENCE: 132
cggctggtcc gccgatcggc tcgg                                         24

<210> SEQ ID NO 133
<211> LENGTH: 24
<212> TYPE: DNA
<213> ORGANISM: artificial sequence
<220> FEATURE:
<223> OTHER INFORMATION: forward primer for amplifying DNA fragment
    A088E02 R.

<400> SEQUENCE: 133
tccaggcgtg gagcctgcgg ctta                                         24

<210> SEQ ID NO 134
<211> LENGTH: 24
<212> TYPE: DNA
<213> ORGANISM: artificial sequence
<220> FEATURE:
<223> OTHER INFORMATION: reverse primer for amplifying DNA fragment
    A088E02 R.

<400> SEQUENCE: 134
tgcaatgatc tatccccatc acga                                         24

<210> SEQ ID NO 135
<211> LENGTH: 24
<212> TYPE: DNA
<213> ORGANISM: artificial sequence
<220> FEATURE:
<223> OTHER INFORMATION: forward primer for amplifying DNA fragment
    A089F12 F.

<400> SEQUENCE: 135
tcgagcagtc cgccggcagc cgac                                         24

<210> SEQ ID NO 136
<211> LENGTH: 24
<212> TYPE: DNA
<213> ORGANISM: artificial sequence
<220> FEATURE:
<223> OTHER INFORMATION: reverse primer for amplifying DNA fragment
    A089F12 F.

<400> SEQUENCE: 136
atttcccgag ccgggacgtg gcgg                                         24

<210> SEQ ID NO 137

```
<211> LENGTH: 24
<212> TYPE: DNA
<213> ORGANISM: artificial sequence
<220> FEATURE:
<223> OTHER INFORMATION: forward primer for amplifying DNA fragment
      A089F12 R.

<400> SEQUENCE: 137
tcgaacagcc gactcagaac tggt                                           24

<210> SEQ ID NO 138
<211> LENGTH: 24
<212> TYPE: DNA
<213> ORGANISM: artificial sequence
<220> FEATURE:
<223> OTHER INFORMATION: reverse primer for amplifying DNA fragment
      A089F12 R.

<400> SEQUENCE: 138
ctcaagtcat ttcacaaagt cgga                                           24

<210> SEQ ID NO 139
<211> LENGTH: 24
<212> TYPE: DNA
<213> ORGANISM: artificial sequence
<220> FEATURE:
<223> OTHER INFORMATION: vector region primer used in PCR1

<400> SEQUENCE: 139
ctgaaggcgg gaaacgacaa tctg                                           24

<210> SEQ ID NO 140
<211> LENGTH: 24
<212> TYPE: DNA
<213> ORGANISM: artificial sequence
<220> FEATURE:
<223> OTHER INFORMATION: vector region primer used in PCR3

<400> SEQUENCE: 140
aactgcactt caaacaagtg tgac                                           24

<210> SEQ ID NO 141
<211> LENGTH: 24
<212> TYPE: DNA
<213> ORGANISM: artificial sequence
<220> FEATURE:
<223> OTHER INFORMATION: primer specific to the genome DNA fragment AS4
      used in PCR1

<400> SEQUENCE: 141
gattccgacc tctacacgaa caac                                           24

<210> SEQ ID NO 142
<211> LENGTH: 24
<212> TYPE: DNA
<213> ORGANISM: artificial sequence
<220> FEATURE:
<223> OTHER INFORMATION: primer specific to the genome DNA fragment AS8
      used in PCR1

<400> SEQUENCE: 142 agaaaccta gccgtcactt ccct                                            24

<210> SEQ ID NO 143
<211> LENGTH: 24
<212> TYPE: DNA
<213> ORGANISM: artificial sequence
<220> FEATURE:
```

<223> OTHER INFORMATION: primer specific to the genome DNA fragment AS19
    used in PCR1

<400> SEQUENCE: 143
tcaagtcatt tcacaaagtc ggac                                              24

<210> SEQ ID NO 144
<211> LENGTH: 24
<212> TYPE: DNA
<213> ORGANISM: artificial sequence
<220> FEATURE:
<223> OTHER INFORMATION: primer specific to the genome DNA fragment AS20
    used in PCR1

<400> SEQUENCE: 144
gcttagaggt gaaaatggta acgg                                              24

<210> SEQ ID NO 145
<211> LENGTH: 24
<212> TYPE: DNA
<213> ORGANISM: artificial sequence
<220> FEATURE:
<223> OTHER INFORMATION: primer specific to the genome DNA fragment AS22
    used in PCR1

<400> SEQUENCE: 145
ttctgtcctt gttcgatttg tcag                                              24

<210> SEQ ID NO 146
<211> LENGTH: 24
<212> TYPE: DNA
<213> ORGANISM: artificial sequence
<220> FEATURE:
<223> OTHER INFORMATION: primer specific to the genome DNA fragment AS27
    used in PCR1

<400> SEQUENCE: 146
ccggattcac cgtggtacga aagg                                              24

<210> SEQ ID NO 147
<211> LENGTH: 24
<212> TYPE: DNA
<213> ORGANISM: artificial sequence
<220> FEATURE:
<223> OTHER INFORMATION: primer specific to the genome DNA fragment AS28
    used in PCR1

<400> SEQUENCE: 147
ttccaattac cagacactaa agcg                                              24

<210> SEQ ID NO 148
<211> LENGTH: 24
<212> TYPE: DNA
<213> ORGANISM: artificial sequence
<220> FEATURE:
<223> OTHER INFORMATION: primer specific to the genome DNA fragment AS30
    used in PCR1

<400> SEQUENCE: 148
tggcaccaga cttgccctcc aatg                                              24

<210> SEQ ID NO 149
<211> LENGTH: 24
<212> TYPE: DNA
<213> ORGANISM: artificial sequence
<220> FEATURE:
<223> OTHER INFORMATION: primer specific to the genome DNA fragment AS4
    used in PCR3

```
<400> SEQUENCE: 149
gtacggcctg ggtcactcac tgtc                                              24

<210> SEQ ID NO 150
<211> LENGTH: 24
<212> TYPE: DNA
<213> ORGANISM: artificial sequence
<220> FEATURE:
<223> OTHER INFORMATION: primer specific to the genome DNA fragment AS8
      used in PCR3

<400> SEQUENCE: 150
tcatcatcct gttatctaga ctcc                                              24

<210> SEQ ID NO 151
<211> LENGTH: 24
<212> TYPE: DNA
<213> ORGANISM: artificial sequence
<220> FEATURE:
<223> OTHER INFORMATION: P primer specific to the genome DNA fragment
      AS19 used in PCR3

<400> SEQUENCE: 151
tacttattcc gtgagtcgga agcg                                              24

<210> SEQ ID NO 152
<211> LENGTH: 24
<212> TYPE: DNA
<213> ORGANISM: artificial sequence
<220> FEATURE:
<223> OTHER INFORMATION: primer specific to the genome DNA fragment AS20
      used in PCR3

<400> SEQUENCE: 152
tccagtgtta tgatgtttgg gctg                                              24

<210> SEQ ID NO 153
<211> LENGTH: 24
<212> TYPE: DNA
<213> ORGANISM: artificial sequence
<220> FEATURE:
<223> OTHER INFORMATION: primer specific to the genome DNA fragment AS22
      used in PCR3

<400> SEQUENCE: 153
aactcatctt taatcccagt ttgc                                              24

<210> SEQ ID NO 154
<211> LENGTH: 24
<212> TYPE: DNA
<213> ORGANISM: artificial sequence
<220> FEATURE:
<223> OTHER INFORMATION: primer specific to the genome DNA fragment AS27
      used in PCR3

<400> SEQUENCE: 154
taacgccata aacaagtgtc actc                                              24

<210> SEQ ID NO 155
<211> LENGTH: 24
<212> TYPE: DNA
<213> ORGANISM: artificial sequence
<220> FEATURE:
<223> OTHER INFORMATION: primer specific to the genome DNA fragment AS28
      used in PCR3

<400> SEQUENCE: 155
```

```
gaactgtgaa actgcgaatg gctc                                              24
```

<210> SEQ ID NO 156
<211> LENGTH: 24
<212> TYPE: DNA
<213> ORGANISM: artificial sequence
<220> FEATURE:
<223> OTHER INFORMATION: primer specific to the genome DNA fragment AS30
      used in PCR3

<400> SEQUENCE: 156

```
aaatccacac gactctcggc aacg                                              24
```

<210> SEQ ID NO 157
<211> LENGTH: 24
<212> TYPE: DNA
<213> ORGANISM: artificial sequence
<220> FEATURE:
<223> OTHER INFORMATION: primer specific to the central portion of the
      genome DNA fragment AS4 used in PCR2

<400> SEQUENCE: 157

```
tgggctccag cagaaacgaa ccct                                              24
```

<210> SEQ ID NO 158
<211> LENGTH: 24
<212> TYPE: DNA
<213> ORGANISM: artificial sequence
<220> FEATURE:
<223> OTHER INFORMATION: primer specific to the central portion of the
      genome DNA fragment AS4 used in PCR2 (reverse)

<400> SEQUENCE: 158

```
cttatattta ggaacggagt gagt                                              24
```

<210> SEQ ID NO 159
<211> LENGTH: 22
<212> TYPE: DNA
<213> ORGANISM: artificial sequence
<220> FEATURE:
<223> OTHER INFORMATION: primer specific to the central portion of the
      genome DNA fragment AS8 used in PCR2

<400> SEQUENCE: 159

```
aagcgaaggc acccttcac at                                                 22
```

<210> SEQ ID NO 160
<211> LENGTH: 22
<212> TYPE: DNA
<213> ORGANISM: artificial sequence
<220> FEATURE:
<223> OTHER INFORMATION: primer specific to the central portion of the
      genome DNA fragment AS8 used in PCR2 (reverse)

<400> SEQUENCE: 160

```
acgaggagcc cgacaaggag ac                                                22
```

<210> SEQ ID NO 161
<211> LENGTH: 24
<212> TYPE: DNA
<213> ORGANISM: artificial sequence
<220> FEATURE:
<223> OTHER INFORMATION: primer specific to the central portion of the
      genome DNA fragment AS22 used in PCR2

<400> SEQUENCE: 161

```
tgaaatacca ctcatgaact tccg                                              24
```

```
<210> SEQ ID NO 162
<211> LENGTH: 24
<212> TYPE: DNA
<213> ORGANISM: artificial sequence
<220> FEATURE:
<223> OTHER INFORMATION: primer specific to the central portion of the
      genome DNA fragment AS22 used in PCR2 (reverse)

<400> SEQUENCE: 162
attatctgtt gtgtccgaaa tgtg                                              24
```